(12) United States Patent
Fujita et al.

(10) Patent No.: US 9,722,184 B2
(45) Date of Patent: Aug. 1, 2017

(54) THIADIAZOLE, COMPOUND FOR LIGHT-EMITTING ELEMENTS, LIGHT-EMITTING ELEMENT, LIGHT-EMITTING APPARATUS, AUTHENTICATION APPARATUS, AND ELECTRONIC DEVICE

(71) Applicant: SEIKO EPSON CORPORATION, Tokyo (JP)

(72) Inventors: Tetsuji Fujita, Chino (JP); Hidetoshi Yamamoto, Suwa (JP)

(73) Assignee: SEIKO EPSON CORPORATION, Tokyo (JP)

( * ) Notice: Subject to any disclaimer, the term of this patent is extended or adjusted under 35 U.S.C. 154(b) by 662 days.

(21) Appl. No.: 14/055,241

(22) Filed: Oct. 16, 2013

(65) Prior Publication Data

US 2014/0110686 A1   Apr. 24, 2014

(30) Foreign Application Priority Data

Oct. 18, 2012   (JP) .................. 2012-230596
Oct. 18, 2012   (JP) .................. 2012-230598
Oct. 18, 2012   (JP) .................. 2012-230599

(51) Int. Cl.
| | |
|---|---|
| *C07D 513/04* | (2006.01) |
| *H01L 51/00* | (2006.01) |
| *H01L 51/50* | (2006.01) |
| *C07D 249/08* | (2006.01) |
| *C07D 513/14* | (2006.01) |
| *C07D 513/22* | (2006.01) |
| *C09K 11/06* | (2006.01) |
| *H05B 33/14* | (2006.01) |

(52) U.S. Cl.
CPC ........ *H01L 51/0061* (2013.01); *C07D 249/08* (2013.01); *C07D 513/04* (2013.01); *C07D 513/14* (2013.01); *C07D 513/22* (2013.01); *C09K 11/06* (2013.01); *H01L 51/0054* (2013.01); *H01L 51/0058* (2013.01); *H01L 51/0059* (2013.01); *H01L 51/0071* (2013.01); *H01L 51/50* (2013.01); *H05B 33/14* (2013.01); *C09K 2211/1007* (2013.01); *C09K 2211/1014* (2013.01); *C09K 2211/1081* (2013.01); *H01L 51/5012* (2013.01); *H01L 51/5072* (2013.01); *Y10S 428/917* (2013.01)

(58) Field of Classification Search
CPC ............. Y10S 428/917; C07D 249/08; H01L 51/0071; H01L 51/5024; C09K 11/06
See application file for complete search history.

(56) References Cited

U.S. PATENT DOCUMENTS

| | | |
|---|---|---|
| 4,769,292 A | 9/1988 | Tang et al. |
| 5,104,740 A | 4/1992 | Shinkai et al. |
| 5,294,869 A | 3/1994 | Tang et al. |
| 5,449,564 A | 9/1995 | Nishio et al. |
| 5,862,434 A | 1/1999 | Yamakawa |
| 6,004,685 A | 12/1999 | Antoniadis et al. |
| 6,680,131 B1 | 1/2004 | Ishibashi et al. |
| 7,097,917 B1 | 8/2006 | Fujita et al. |
| 7,632,579 B2 | 12/2009 | Ise et al. |
| 7,714,099 B2 | 5/2010 | Morishita et al. |
| 7,902,542 B2 | 3/2011 | Haase et al. |
| 7,919,773 B2 | 4/2011 | Kawakami et al. |
| 7,947,992 B2 | 5/2011 | Yasukawa et al. |
| 7,960,912 B2 | 6/2011 | Yasukawa et al. |
| 8,039,128 B2 | 10/2011 | Watanabe et al. |

(Continued)

FOREIGN PATENT DOCUMENTS

| | | |
|---|---|---|
| CN | 103187532 A | 7/2013 |
| EP | 0 281 381 B1 | 7/1992 |

(Continued)

OTHER PUBLICATIONS

Nov. 17, 2015 Office Action issued in U.S. Appl. No. 13/444,107.
Mar. 3, 2016 Office Action issued in U.S. Appl. No. 13/444,107.
Wang et al., "Syntheses, characterization and fluorescent properties of two series of dehydroabietic acid C-ring derivatives," Spectrochimica Acta Part A: Molecular and Biomolecular Spectroscopy, vol. 76, pp. 328-335, 2010.
May 9, 2016 Office Action issued in U.S. Appl. No. 14/693,484.
U.S. Appl. No. 13/445,523 in the name of Fujita et al., filed Apr. 12, 2012.
U.S. Appl. No. 13/564,384 in the name of Fujita et al., filed Aug. 1, 2012.

(Continued)

*Primary Examiner* — Gregory Listvoyb
(74) *Attorney, Agent, or Firm* — Oliff PLC

(57) ABSTRACT

A thiadiazole contains a basic skeleton represented by any of formulae (1), (2), and (3) in the molecule.

(1)

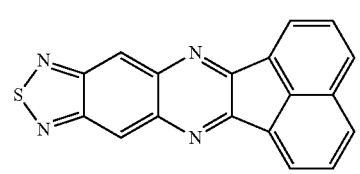

(2)

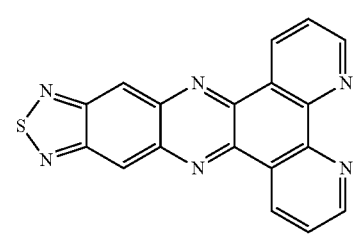

(3)

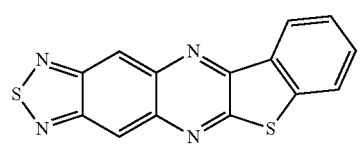

19 Claims, 4 Drawing Sheets

(56) References Cited

U.S. PATENT DOCUMENTS

| | | | |
|---|---|---|---|
| 8,803,138 B2 | 8/2014 | Fujita et al. | |
| 8,809,547 B2* | 8/2014 | Bretschneider | A01N 43/56 504/263 |
| 9,067,952 B2* | 6/2015 | Yamamoto | C07D 487/04 |
| 9,072,150 B2 | 6/2015 | Fujita et al. | |
| 9,159,932 B2* | 10/2015 | Fujita | H01L 51/0059 |
| 9,324,952 B2* | 4/2016 | Yamamoto | C07D 513/04 |
| 2002/0089560 A1 | 7/2002 | Katayama et al. | |
| 2003/0008172 A1 | 1/2003 | Leclerc et al. | |
| 2003/0027016 A1 | 2/2003 | Ara et al. | |
| 2004/0018382 A1 | 1/2004 | Kinlen | |
| 2005/0079381 A1 | 4/2005 | Hamada et al. | |
| 2005/0106415 A1 | 5/2005 | Jarikov et al. | |
| 2006/0063027 A1 | 3/2006 | Vestweber et al. | |
| 2006/0154105 A1 | 7/2006 | Yamamoto et al. | |
| 2007/0077453 A1 | 4/2007 | Sano et al. | |
| 2007/0254432 A1 | 11/2007 | Yamazaki et al. | |
| 2007/0285005 A1 | 12/2007 | Itai | |
| 2008/0061681 A1 | 3/2008 | Thompson et al. | |
| 2008/0067479 A1 | 3/2008 | Kimura et al. | |
| 2008/0125593 A1 | 5/2008 | Kim et al. | |
| 2008/0230123 A1 | 9/2008 | Mitsui et al. | |
| 2009/0079335 A1 | 3/2009 | Mitsuya et al. | |
| 2009/0091250 A1 | 4/2009 | Yasukawa et al. | |
| 2009/0115348 A1 | 5/2009 | Yamazaki et al. | |
| 2009/0243476 A1 | 10/2009 | Nomura et al. | |
| 2009/0261360 A1 | 10/2009 | Yasukawa et al. | |
| 2010/0108992 A1 | 5/2010 | Ikeda et al. | |
| 2010/0133434 A1 | 6/2010 | Meng et al. | |
| 2010/0155694 A1 | 6/2010 | Miller et al. | |
| 2010/0194807 A1 | 8/2010 | Hirasawa et al. | |
| 2010/0237338 A1 | 9/2010 | Yamamoto et al. | |
| 2010/0237990 A1 | 9/2010 | Amano et al. | |
| 2010/0244671 A1 | 9/2010 | Nomura et al. | |
| 2010/0244679 A1 | 9/2010 | Fujita et al. | |
| 2010/0252823 A1 | 10/2010 | Kambe et al. | |
| 2010/0317858 A1 | 12/2010 | Konno | |
| 2011/0058192 A1 | 3/2011 | Hatanaka et al. | |
| 2011/0087034 A1 | 4/2011 | Miyata et al. | |
| 2011/0127505 A1 | 6/2011 | Nakamura et al. | |
| 2011/0253988 A1 | 10/2011 | Molt et al. | |
| 2011/0279020 A1 | 11/2011 | Inoue et al. | |
| 2011/0303901 A1 | 12/2011 | Cheng et al. | |
| 2012/0056213 A1 | 3/2012 | Yamamoto et al. | |
| 2012/0091923 A1 | 4/2012 | Kastner-Jung et al. | |
| 2012/0262057 A1 | 10/2012 | Fujita et al. | |
| 2012/0267615 A1 | 10/2012 | Fujita et al. | |
| 2013/0009909 A1 | 1/2013 | Yamazaki et al. | |
| 2013/0032791 A1 | 2/2013 | Bazan et al. | |
| 2013/0037784 A1 | 2/2013 | Yamamoto et al. | |
| 2013/0037785 A1 | 2/2013 | Fujita et al. | |
| 2013/0099209 A1 | 4/2013 | Hartmann et al. | |
| 2013/0168654 A1 | 7/2013 | Fujita et al. | |
| 2013/0221334 A1 | 8/2013 | Yamamoto et al. | |
| 2014/0332835 A1 | 11/2014 | Fujita et al. | |
| 2015/0236226 A1 | 8/2015 | Fujita et al. | |

FOREIGN PATENT DOCUMENTS

| | | |
|---|---|---|
| JP | A-63-264692 | 11/1988 |
| JP | A-02-255788 | 10/1990 |
| JP | A-03-000791 | 1/1991 |
| JP | A-03-000792 | 1/1991 |
| JP | A-03-162481 | 7/1991 |
| JP | A-03-177486 | 8/1991 |
| JP | A-05-032966 | 2/1993 |
| JP | A-05-214334 | 8/1993 |
| JP | A-05-258859 | 10/1993 |
| JP | A-06-073374 | 3/1994 |
| JP | A-06-093257 | 4/1994 |
| JP | A-06-136359 | 5/1994 |
| JP | A-06-145146 | 5/1994 |
| JP | A-06-240246 | 8/1994 |
| JP | H07-52375 A | 2/1995 |
| JP | H09-236965 A | 9/1997 |
| JP | A-10-330295 | 12/1998 |
| JP | H11-179895 A | 7/1999 |
| JP | 11-217776 A | 8/1999 |
| JP | A-11-233261 | 8/1999 |
| JP | A-2000-091073 | 3/2000 |
| JP | 2001-097949 A | 4/2001 |
| JP | A-2001-110570 | 4/2001 |
| JP | 2001-270585 A | 10/2001 |
| JP | A-2002-97465 | 4/2002 |
| JP | A-2003-55652 | 2/2003 |
| JP | 2003-109760 A | 4/2003 |
| JP | 2004/002297 A | 1/2004 |
| JP | A-2005-63938 | 3/2005 |
| JP | 2005-531552 A | 10/2005 |
| JP | 2006-045398 A | 2/2006 |
| JP | 2006-511939 A | 4/2006 |
| JP | 2007-000769 A | 1/2007 |
| JP | A-2007-115626 | 5/2007 |
| JP | 2008/069100 A | 3/2008 |
| JP | 2008-133277 A | 6/2008 |
| JP | 2008-162921 A | 7/2008 |
| JP | 2008-546185 A | 12/2008 |
| JP | A-2009-16693 | 1/2009 |
| JP | 2009/049094 A | 3/2009 |
| JP | 2009-256343 A | 11/2009 |
| JP | 2009-272144 A | 11/2009 |
| JP | 2010-147179 A | 7/2010 |
| JP | 2010-179544 A | 8/2010 |
| JP | 2010-245211 A | 10/2010 |
| JP | 2010/254674 A | 11/2010 |
| JP | 2011-508368 A | 3/2011 |
| JP | 2011-073432 A | 4/2011 |
| JP | 2011-134810 A | 7/2011 |
| WO | 03-095445 A1 | 11/2003 |
| WO | 2004-058911 A2 | 7/2004 |
| WO | 2006-127315 A2 | 11/2006 |
| WO | WO 2008-69322 A1 | 6/2008 |
| WO | 2008-094187 A2 | 8/2008 |
| WO | 2009075741 A1 | 6/2009 |

OTHER PUBLICATIONS

U.S. Appl. No. 13/773,033 in the name of Yamamoto et al., filed Feb. 21, 2013.
Sep. 5, 2014 Notice of Allowance issued in U.S. Appl. No. 13/445,523.
U.S. Appl. No. 13/444,107 in the name of Fujita et al., filed Apr. 11, 2012.
Pending U.S. Appl. No. 14/319,410, filed Jun. 30, 2014.
Feb. 13, 2015 Notice of Allowance issued in U.S. Appl. No. 14/319,410.
U.S. Appl. No. 14/693,484, filed Apr. 22, 2015 in the name of Yamamoto et al.
U.S. Appl. No. 14/700,751, filed Apr. 30, 2015 in the name of Fujita et al.
Apr. 22, 2015 Office Action issued in U.S. Appl. No. 13/773,033.
Jan. 23, 2015 Notice of Allowance issued in U.S. Appl. No. 13/564,376.
Mar. 24, 2015 Supplemental Notice of Allowability issued in U.S. Appl. No. 13/564,376.
Feb. 20, 2015 Notice of Allowance issued in U.S. Appl. No. 13/445,523.
Pending U.S. Appl. No. 13/564,376, filed Aug. 1, 2012.
Jun. 29, 2015 Office Action issued in U.S. Appl. No. 13/444,107.
Aug. 24, 2015 Office Action issued in U.S. Appl. No. 13/773,033.
Kawbe et al., "Electroluminescence of Green Light Region in Doped Anthracene," Japanese Journal of Applied Physics, vol. 10, 1971, pp. 527-528.
Debad et al., "Dibenzotetraphenylperiflanthene: Synthesis, Photophysical Properties, and Electrogenerated Chemiluminescence," Journal of American Chemical Society, vol. 118, 1996, pp. 2374-2379.
Oct. 7, 2015 Office Action issued in U.S. Appl. No. 14/700,751.

(56) References Cited

OTHER PUBLICATIONS

Du et al; "Efficient Non-doped Near Infrared Organic Light-Emitting Devices Based on Fluorophores with Aggregation-Induced Emission Enhancement;" Chemistry of Materials; May 2012; pp. 2178-2185.
Kajii et al; "Visible to near-infrared organic light-emitting diodes using phosphorescent materials by solution process;" Thin Solid Films; Jul. 2009; pp. 551-554.
Qian, G. et al; "Synthesis and Application of Thiadiazoloquinoxaline-Containing Chromophores as Dopants for Efficient Near-Infrared Organic Light-Emitting Diodes;" J. Phys. Chem. C; Jan. 2009; vol. 113; pp. 1589-1595.
Jan. 10, 2014 Office Action issued in U.S. Appl. No. 13/445,523.
Jun. 18, 2014 Office Action issued in U.S. Appl. No. 13/445,523.
Sep. 5, 2012 Notice of Allowance issued in U.S. Appl. No. 13/445,523.
Aug. 15, 2014 Office Action issued in U.S. Appl. No. 13/564,384.
Aug. 21, 2014 Office Action issued in U.S. Appl. No. 13/564,376.
Oct. 3, 2014 Office Action issued in U.S. Appl. No. 14/319,410.
Mar. 26, 2014 Notice of Allowance issued in U.S. Appl. No. 13/727,339.
Dec. 18, 2015 Office Action issued in U.S. Appl. No. 14/693,484.
Aug. 11, 2016 Office Action issued in U.S. Appl. No. 13/444,107.
Jan. 22, 2015 Office Action issued in U.S. Appl. No. 13/564,384.
Hamada et al., "Red organic light-emitting diodes using an emitting assist dopant," Applied Physics Letters, vol. 75, No. 12, pp. 1682-1684, Sep. 20, 1999.
Feb. 24, 2017 Office Action Issued in U.S. Appl. No. 13/444,107.

* cited by examiner

THIADIAZOLE, COMPOUND FOR LIGHT-EMITTING ELEMENTS, LIGHT-EMITTING ELEMENT, LIGHT-EMITTING APPARATUS, AUTHENTICATION APPARATUS, AND ELECTRONIC DEVICE

BACKGROUND

1. Technical Field

Several aspects of the present invention relate to a thiadiazole, a compound for light-emitting elements, a light-emitting element, a light-emitting apparatus, an authentication apparatus, and an electronic device.

2. Related Art

Organic electroluminescent elements (organic EL elements) are light-emitting elements composed of an anode, a cathode, and at least one organic light-emitting layer interposed between them. Upon the application of an electric field impressed between the anode and the cathode, holes in the anode and electrons in the cathode are injected into the light-emitting layer(s) and recombine with each other in the light-emitting layer(s), generating excitons. These excitons release energy in the form of light while returning to the ground state.

Known examples of such light-emitting elements are ones that emit long-wavelength light having a wavelength longer than 700 nm (e.g., see JP-A-2000-091073 and JP-A-2001-110570).

The light-emitting elements described in these patent publications can emit light with such a long wavelength because the light-emitting layer(s) are doped with a compound that contains both electron-donating and electron-withdrawing functional groups, namely amine and a nitrile group, in the molecule.

However, it has been impossible to provide such near-infrared-emitting elements with high efficiency and long life.

Light-emitting elements that can emit near-infrared light from a surface and that are of high efficiency and long life are in demand for use as, for example, a light source for biometric authentication, by which individuals are verified on the basis of their biological traits, such as vein patterns or fingerprints.

SUMMARY

An advantage of some aspects of the invention is that they provide a high-efficiency and long-life thiadiazole that can emit near-infrared light, a compound for light-emitting elements and a light-emitting element advantageous in the same way, and a light-emitting apparatus, an authentication apparatus, and an electronic device having such a light-emitting element.

The following describes some aspects of the invention.

A thiadiazole according to an aspect of the invention contains a basic skeleton represented by formula (1), (2), or (3) in the molecule.

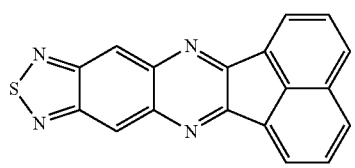

(1)

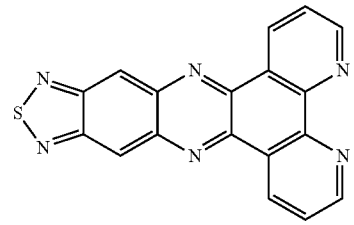

(2)

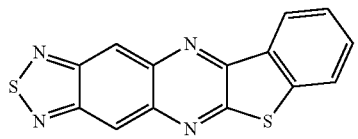

(3)

Such a thiadiazole, when used as a light-emitting material in an organic EL element, for example, allows the EL element to emit near-infrared light.

Preferably, the thiadiazole according to this aspect of the invention is a compound represented by formula (4) when containing the basic skeleton represented by formula (1) in the molecule, a compound represented by formula (5) when containing the basic skeleton represented by formula (2) in the molecule, or a compound represented by formula (6) when containing the basic skeleton represented by formula (3) in the molecule:

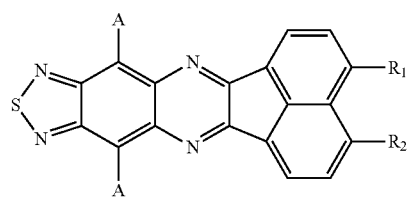

(4)

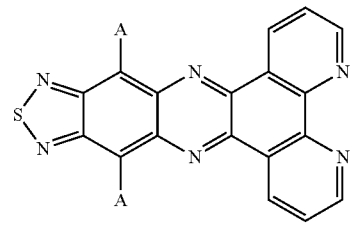

(5)

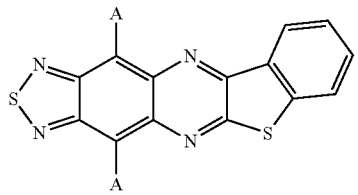

(6)

where each A independently represents a hydrogen atom, an alkyl group, or a substituted or unsubstituted aryl group, aryl amino group, or triarylamine, each of $R_1$ and $R_2$ independently represents a hydrogen atom, an alkyl group, or a substituted or unsubstituted aryl group, and $R_1$ and $R_2$ may be the same or different.

Such a thiadiazole, when used as a light-emitting material in an organic EL element, for example, makes the EL element more efficient and able to operate for a longer period of time in addition to allowing the element to emit near-infrared light.

Furthermore, the thiadiazole according to this aspect of the invention is preferably a compound represented by formula (7), (8), or (9) when it is a compound represented by formula (4). Likewise, the compound represented by formula (5) is preferably a compound represented by formula (10), (11), or (12), and the compound represented by formula (6) is preferably a compound represented by formula (13), (14), or (15):
(7)
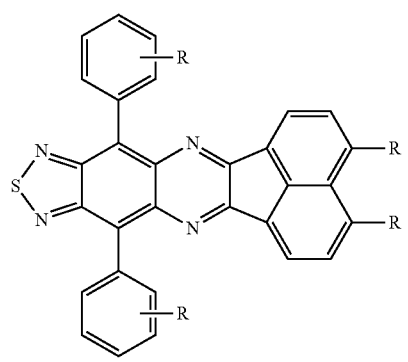
(8)
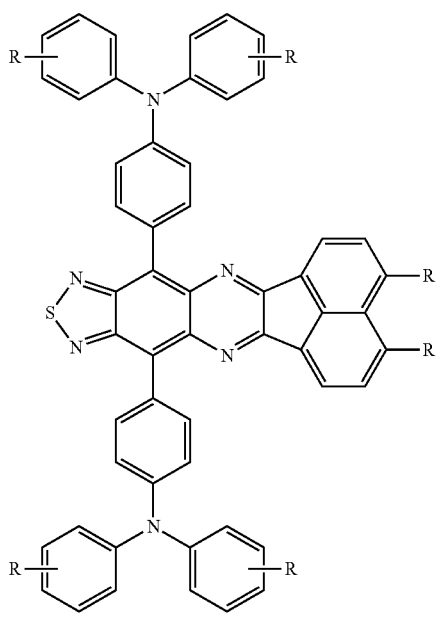
(9)
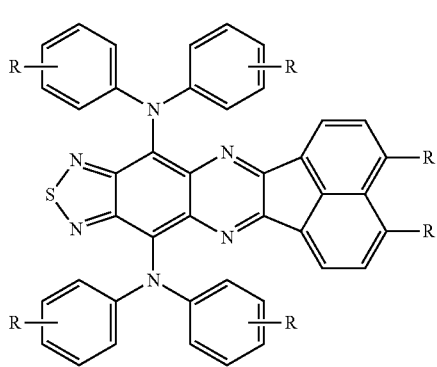
(10)
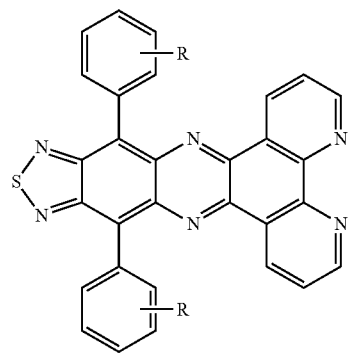
(11)
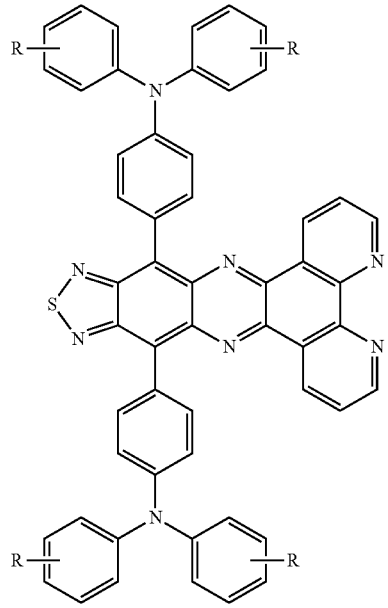
(12)
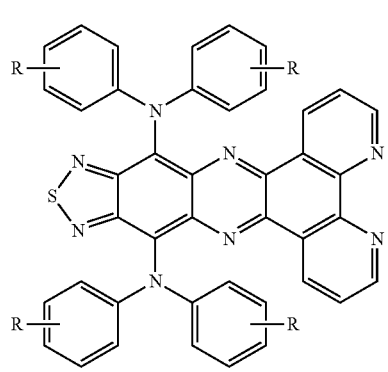

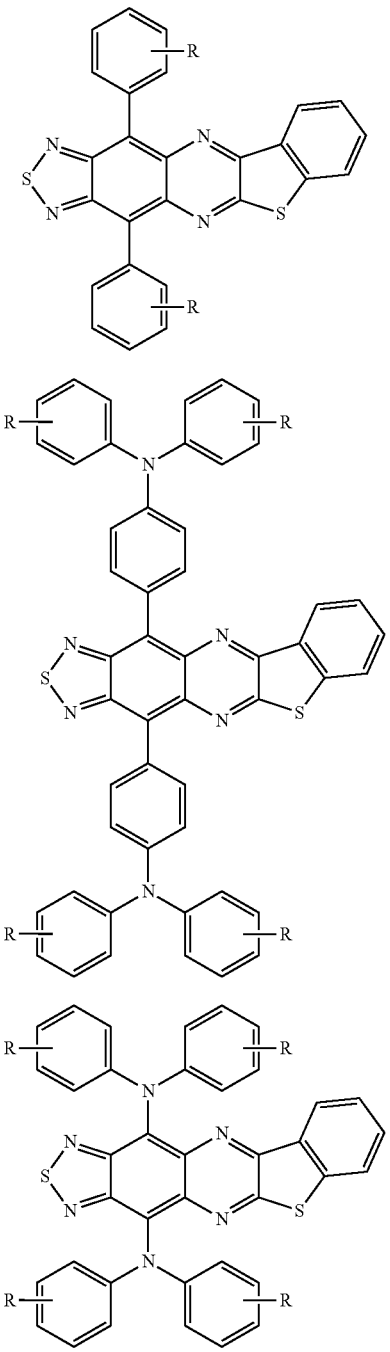

where each R independently represents a hydrogen atom, an alkyl group, or a substituted or unsubstituted aryl group, and there may be a ring formed by a carbon linkage between two adjacent R's.

Such a thiadiazole, when used as a light-emitting material in an organic EL element, for example, also makes the EL element more efficient and able to operate for a longer period of time in addition to allowing the element to emit near-infrared light.

A compound for light-emitting elements according to another aspect of the invention contains a thiadiazole according to one aspect of the invention.

Such a compound, when used as a light-emitting material in a light-emitting element, for example, allows the element to emit near-infrared light.

A light-emitting element according to another aspect of the invention has an anode, a cathode, and a layer between the anode and the cathode. The layer contains a thiadiazole according to one aspect of the invention.

This configuration allows the light-emitting element to emit light having a wavelength of 700 nm or more (near-infrared light) because the light-emitting material is a compound containing a basic skeleton represented by formula (1), (2), or (3) in the molecule.

Preferably, the aforementioned layer of the light-emitting element according to this aspect of the invention contains the thiadiazole as a guest material and also contains a host material for the guest material.

This ensures that the compound containing a basic skeleton represented by formula (1), (2), or (3) in the molecule (the thiadiazole according to one aspect of the invention) is excited efficiently.

The host material used in the light-emitting element according to this aspect of the invention is preferably a compound represented by formula IRH-1:

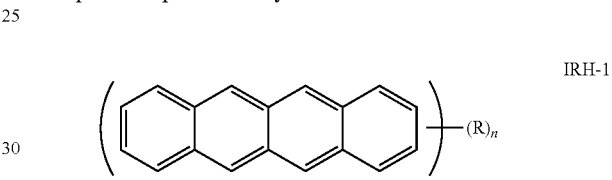

where n represents a natural number of 1 to 12, and each R is independently a hydrogen atom, an alkyl group, or a substituted or unsubstituted aryl or aryl amino group.

This is advantageous in that efficient energy transfer from the tetracene-based host material to the light-emitting material ensures excellent light emission efficiency of the light-emitting element.

Furthermore, tetracene-based materials are inert (highly resistant) to electrons and holes. The use of the tetracene-based host material thus also allows the light-emitting layer, and therefore the entire light-emitting element, to operate for a longer period of time.

It is also preferred that the host material used in the light-emitting element according to this aspect of the invention is a compound represented by formula IRH-2:

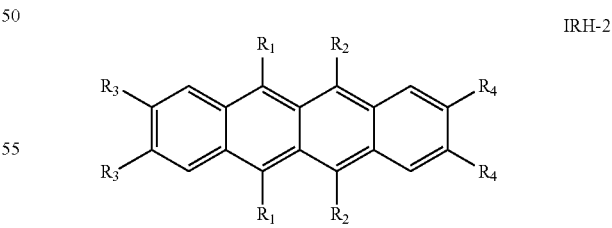

where each of $R_1$ to $R_4$ independently represents a hydrogen atom, an alkyl group, or a substituted or unsubstituted aryl or aryl amino group, with some or all of $R_1$ to $R_4$ the same or all of $R_1$ to $R_4$ different.

This arrangement provides overvoltage protection during continuous operation while enhancing the light emission efficiency of the light-emitting element and extending the life of the light-emitting element.

It is also preferred that the host material used in the light-emitting element according to this aspect of the invention is a compound represented by formula IRH-3:

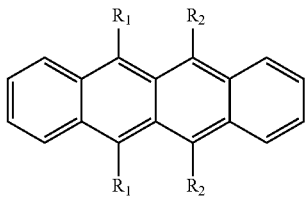

IRH-3 where each of $R_1$ and $R_2$ independently represents a hydrogen atom, an alkyl group, or a substituted or unsubstituted aryl or aryl amino group, and $R_1$ and $R_2$ may be the same or different.

This arrangement also provides overvoltage protection during continuous operation while enhancing the light emission efficiency of the light-emitting element and extending the life of the light-emitting element.

It is also preferred that the host material used in the light-emitting element according to this aspect of the invention is a compound represented by formula IRH-4:

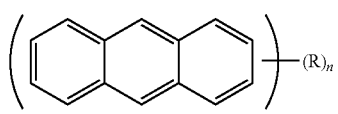

IRH-4 where n represents a natural number of 1 to 10, and each R independently represents a hydrogen atom, an alkyl group, or a substituted or unsubstituted aryl or aryl amino group.

This is advantageous in that efficient energy transfer from the anthracene-based host material to the light-emitting material ensures excellent light emission efficiency of the light-emitting element.

Furthermore, anthracene-based materials are inert (highly resistant) to electrons and holes. The use of the anthracene-based host material thus also allows the light-emitting layer, and therefore the entire light-emitting element, to operate for a longer period of time.

It is also preferred that the host material used in the light-emitting element according to this aspect of the invention is a compound represented by formula IRH-5:

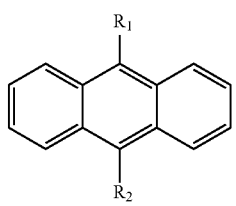

IRH-5 where each of $R_1$ and $R_2$ independently represents a hydrogen atom, an alkyl group, or a substituted or unsubstituted aryl or aryl amino group, and $R_1$ and $R_2$ may be the same or different.

This arrangement provides overvoltage protection during continuous operation while enhancing the light emission efficiency of the light-emitting element and extending the life of the light-emitting element.

It is also preferred that the host material used in the light-emitting element according to this aspect of the invention is a compound represented by formula IRH-6:

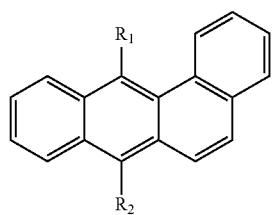

IRH-6 where each of $R_1$ and $R_2$ independently represents a hydrogen atom, an alkyl group, or a substituted or unsubstituted aryl or aryl amino group, and $R_1$ and $R_2$ may be the same or different.

This arrangement also provides overvoltage protection during continuous operation while enhancing the light emission efficiency of the light-emitting element and extending the life of the light-emitting element.

It is also preferred that the host material used in the light-emitting element according to this aspect of the invention is a compound represented by formula IRH-7:

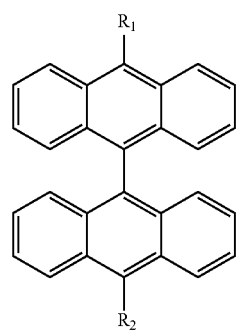

IRH-7 where each of $R_1$ and $R_2$ independently represents a hydrogen atom, an alkyl group, or a substituted or unsubstituted aryl or aryl amino group, and $R_1$ and $R_2$ may be the same or different.

This arrangement also provides overvoltage protection during continuous operation while enhancing the light emission efficiency of the light-emitting element and extending the life of the light-emitting element.

It is also preferred that the host material used in the light-emitting element according to this aspect of the invention is a compound represented by formula IRH-8:

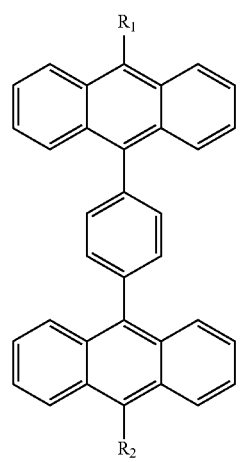

IRH-8 where each of $R_1$ and $R_2$ independently represents a hydrogen atom, an alkyl group, or a substituted or unsubstituted aryl or aryl amino group, and $R_1$ and $R_2$ may be the same or different.

This arrangement also provides overvoltage protection during continuous operation while enhancing the light emission efficiency of the light-emitting element and extending the life of the light-emitting element.

It is also preferred that the host material used in the light-emitting element according to this aspect of the invention is composed of carbon and hydrogen atoms.

This prevents unwanted interactions between the host material and the light-emitting material and thus enhances the light emission efficiency of the light-emitting element. The resistance of the host material to electrons and holes is also increased, extending the life of the light-emitting element.

Preferably, the light-emitting element according to this aspect of the invention contains the thiadiazole as a light-emitting material, and the aforementioned layer of the light-emitting element is a light-emitting layer which emits light when electric current flows between the anode and the cathode.

This ensures that the light-emitting element can emit light having a wavelength of 700 nm or more (near-infrared light).

A light-emitting apparatus according to another aspect of the invention has a light-emitting element according to one aspect of the invention.

Such a light-emitting apparatus can emit near-infrared light, and has excellent reliability because of the high efficiency and long life of the light-emitting element.

An authentication apparatus according to another aspect of the invention has a light-emitting element according to one aspect of the invention.

Such an authentication apparatus allows biometric authentication using near-infrared light, and has excellent reliability because of the high efficiency and long life of the light-emitting element.

An electronic device according to another aspect of the invention has a light-emitting element according to one aspect of the invention.

Such an electronic device has excellent reliability because of the high efficiency and long life of the light-emitting element.

BRIEF DESCRIPTION OF THE DRAWINGS

The invention will be described with reference to the accompanying drawings, wherein like numbers reference like elements.

DESCRIPTION OF EXEMPLARY EMBODIMENTS

The following describes preferred embodiments of the thiadiazole, the compound for light-emitting elements, the light-emitting element, the light-emitting apparatus, the authentication apparatus, and the electronic device according to aspects of the invention with reference to attached drawings.

Figure 1:
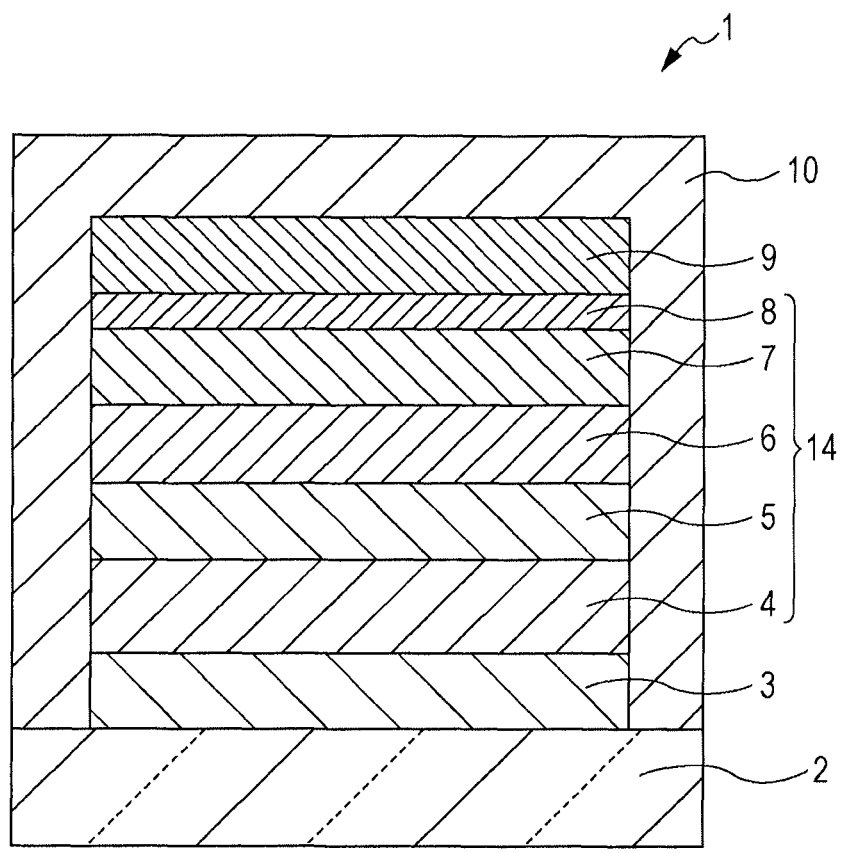
FIG. 1 schematically illustrates a cross-section of a light-emitting element according to an embodiment of the invention.

FIG. 1 schematically illustrates a cross-section of a light-emitting element according to an embodiment of the invention. For the sake of convenience, the top and bottom in FIG. 1 are hereinafter regarded as the top and bottom of the light-emitting element, respectively.

The light-emitting element (electroluminescence element) 1 illustrated in FIG. 1 has an anode 3, a hole injection layer 4, a hole transport layer 5, a light-emitting layer 6, an electron transport layer 7, an electron injection layer 8, and a cathode 9 stacked in this order. In other words, the light-emitting element 1 has a laminate 14 interposed between the anode 3 and the cathode 9, and the laminate 14 contains the hole injection layer 4, the hole transport layer 5, the light-emitting layer 6, the electron transport layer 7, and the electron injection layer 8 stacked in this order from the anode 3 side to the cathode 9 side.

The entire light-emitting element 1 is formed on a substrate 2 and sealed with a sealing member 10.

In such a light-emitting element 1, the light-emitting layer 6 receives electrons supplied (injected) from the cathode 9 side and holes supplied (injected) from the anode 3 side when driving voltage is applied to the anode 3 and the cathode 9. Then in the light-emitting layer 6 the holes and electrons recombine and release recombination energy, and the released energy generates excitons. The excitons release energy (fluorescence or phosphorescence), or in other words emit light, while returning to the ground state. As a result, the light-emitting element 1 emits light.

An important feature of this light-emitting element 1 is that it can emit near-infrared light because, as described later herein, the light-emitting layer 6 contains a thiadiazole (a compound for light-emitting elements) as a light-emitting material. The term near-infrared, as used herein, represents the wavelength range from 700 nm to 1500 nm, both inclusive.

The substrate 2 supports the anode 3. The light-emitting element 1 according to this embodiment emits light through the substrate 2 side (bottom-emission); thus, the substrate 2 and the anode 3 are substantially transparent (colorless and transparent, colored and transparent, or translucent).

Examples of materials that can be used to make the substrate 2 include resin materials such as polyethylene terephthalate, polyethylene naphthalate, polypropylene, cycloolefin polymers, polyamides, polyethersulfone, polymethyl methacrylate, polycarbonates, and polyarylates and glass materials such as quartz glass and soda lime glass. One or a combination of two or more of such materials can be used.

The average thickness of such a substrate 2 is not limited. It is preferably on the order of 0.1 mm to 30 mm, more preferably on the order of 0.1 mm to 10 mm.

When the light-emitting element 1 emits light through the surface opposite to the substrate 2 (top-emission), the substrate 2 may be a transparent substrate or an opaque substrate.

Examples of appropriate opaque substrates include those made of ceramic materials such as alumina, those made of metals such as stainless steel and coated with an oxide film (an insulating film), and those made of resin materials.

The distance between the anode 3 and the cathode 9 (i.e., the average thickness of the laminate 14) in such a light-emitting element 1 is preferably in the range of 100 nm to 500 nm, more preferably 100 nm to 300 nm, and even more preferably 100 nm to 250 nm. This allows easy and consistent control of the driving voltage of the light-emitting element 1 within the practical range.

The following describes the individual components of the light-emitting element 1 in more detail.

Anode

The anode 3 injects holes into the hole transport layer 5 via the hole injection layer 4 described later herein. Preferably, the anode 3 is made of a material having a high work function and excellent conductivity.

Examples of materials that can be used to make the anode 3 include oxides such as ITO (indium tin oxide), IZO (indium zinc oxide), $In_2O_3$, $SnO_2$, Sb-containing $SnO_2$, and Al-containing ZnO, metals such as Au, Pt, Ag, and Cu, and alloys of such metals. One or a combination of two or more of such materials can be used.

Preferably, the anode 3 is made of ITO. ITO has transparency, a high work function, and excellent conductivity. These features of ITO allow efficient injection of holes from the anode 3 into the hole injection layer 4.

It is also preferred that the surface of the anode 3 on the hole injection layer 4 side (the top surface in FIG. 1) is treated with plasma. This improves the chemical and mechanical stability of the interface between the anode 3 and the hole injection layer 4 and thus facilitates hole injection from the anode 3 into the hole injection layer 4. A process of plasma treatment for this purpose is described later herein in the description of a method for producing the light-emitting element 1.

The average thickness of such an anode 3 is not limited. It is preferably on the order of 10 nm to 200 nm, more preferably on the order of 50 nm to 150 nm.

Cathode

The cathode 9 injects electrons into the electron transport layer 7 via the electron injection layer 8 described later herein. Preferably, the cathode 9 is made of a material having a low work function.

Examples of materials that can be used to make the cathode 9 include Li, Mg, Ca, Sr, La, Ce, Er, Eu, Sc, Y, Yb, Ag, Cu, Al, Cs, and Rb and alloys of such metals. One or a combination of two or more of such materials can be used (in the form of a laminate having some layers made of different materials or a hybrid layer containing different materials, for example).

When the cathode 9 is made of an alloy, it is preferred to use an alloy containing a stable metal element such as Ag, Al, or Cu, or more specifically an alloy such as MgAg, AlLi, or CuLi. Such an alloy, when used to make the cathode 9, improves the electron injection efficiency and the stability of the cathode 9.

Preferably, the cathode 9 is made of Al, Ag, or MgAg, more preferably MgAg, because these materials are highly reflective to near-infrared light.

When the cathode 9 is made of MgAg, the ratio of Mg to Ag (Mg:Ag) is preferably in the range of 1:100 to 100:1 as this leads to enhanced reflection of near-infrared light.

The average thickness of such a cathode 9 is not limited. It is preferably on the order of 2 nm to 10000 nm, more preferably on the order of 50 nm to 200 nm.

The light-emitting element 1 according to this embodiment has the bottom-emission structure and its cathode 9 does not have to be transparent to light. When the top-emission structure is used, it is preferred that the average thickness of the cathode 9 is on the order of 1 nm to 50 nm because the outgoing light should be able to pass through the cathode 9 side.

There may be a reflection layer reflective to near-infrared light on the top side with respect to the cathode 9 (the side opposite to the light-emitting layer 6). Such a reflection layer is preferably made of Al, Ag, or Mg and preferably borders the cathode 9.

Hole Injection Layer

The hole injection layer 4 improves the efficiency of the injection of holes from the anode 3 (i.e., this layer has hole injection properties).

Placed between the anode 3 and the hole transport layer 5 (described later herein) in the way described above, the hole injection layer 4 facilitates hole injection from the anode 3 and thus enhances the light emission efficiency of the light-emitting element 1.

The hole injection layer 4 contains a material having hole injection properties (i.e., a hole injection material).

The hole injection layer 4 can contain any kind of hole injection material. Examples of appropriate materials include copper phthalocyanine, 4,4',4"-tris(N,N-phenyl-3-methylphenylamino)triphenylamine (m-MTDATA), and N,N'-bis(4-diphenylaminophenyl)-N,N'-diphenylbiphenyl-4,4'-diamine.

Preferably, the hole injection layer 4 contains an amine-based hole injection material because this kind of material has excellent hole injection and hole transport properties. More preferably, the hole injection material is a diaminobenzene derivative, a benzidine derivative (a material having a benzidine skeleton), or a triamine or tetramine having both diaminobenzene and benzidine units in the molecule.

The average thickness of such a hole injection layer 4 is not limited. It is preferably on the order of 5 nm to 90 nm, more preferably on the order of 10 nm to 70 nm.

The hole injection layer 4 may be omitted, depending on the composition of the anode 3 and the hole transport layer 5.

Hole Transport Layer

The hole transport layer 5 receives the holes injected from the anode 3 via the hole injection layer 4 and transmits them to the light-emitting layer 6 (i.e., this layer has hole transport properties).

The hole transport layer 5 contains a material having hole transport properties (i.e., a hole transport material).

The hole transport material used in the hole transport layer 5 may be one or a combination of p-type polymers and p-type low-molecular-weight compounds. Specific examples of appropriate hole transport materials include tetraarylbenzidine derivatives such as N,N'-di(1-naphthyl)-N,N'-diphenyl-1,1'-diphenyl-4,4'-diamine (NPD) and N,N'-diphenyl-N,N'-bis(3-methylphenyl)-1,1'-diphenyl-4,4'-diamine (TPD) and tetraaryldiaminofluorenes and their derivatives (amines). One or a combination of two or more of such materials can be used.

Preferably, the hole transport layer 5 contains an amine-based hole transport material, more preferably a benzidine derivative (a material having a benzidine skeleton), because this kind of material has excellent hole injection and hole transport properties. Examples of such amine-based materials include compounds HTL-1 to HTL-15.

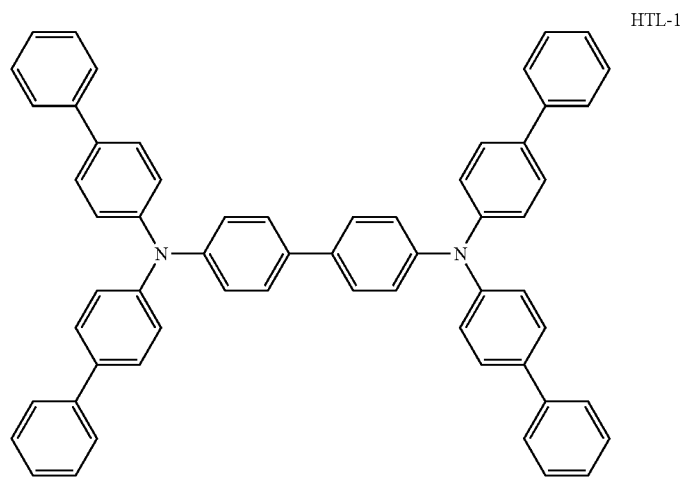
HTL-1
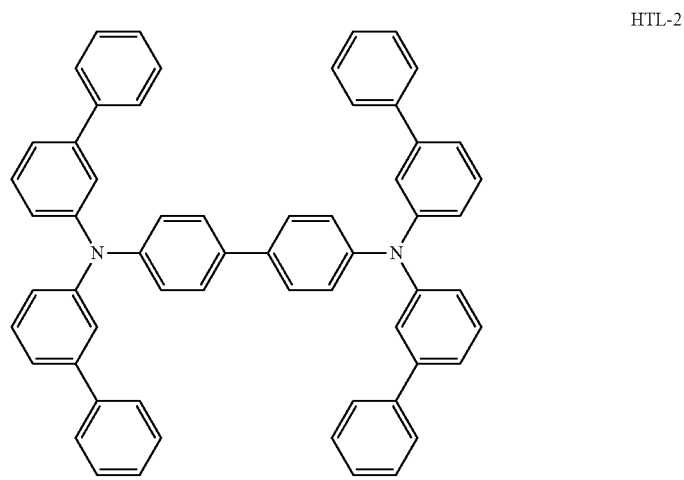
HTL-2
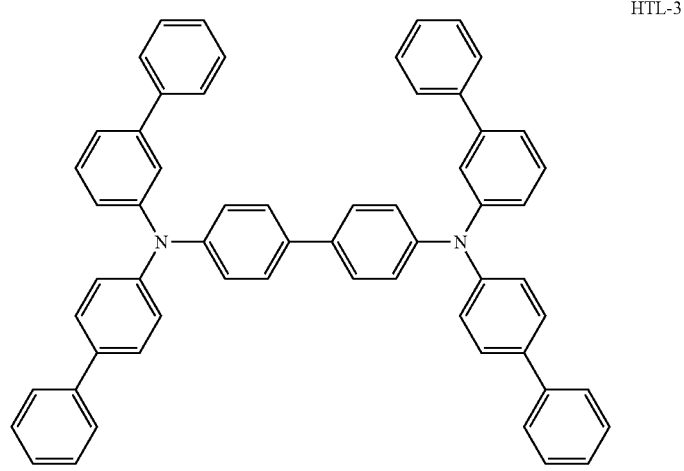
HTL-3

HTL-4
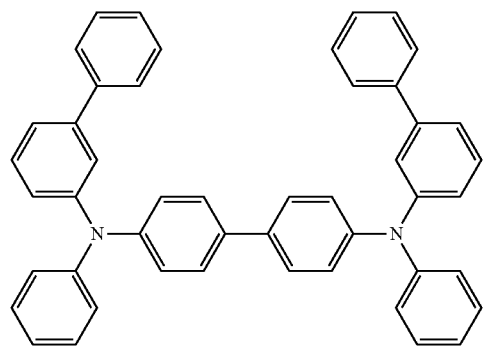
HTL-5
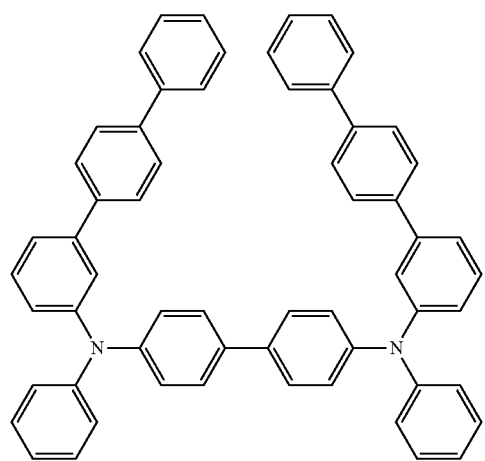
HTL-6
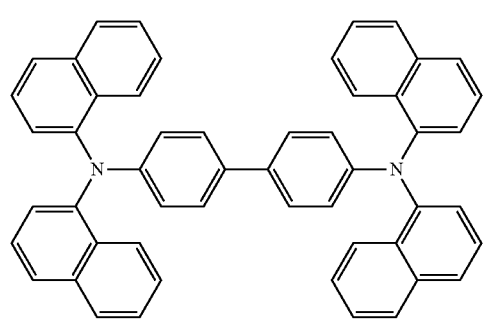
HTL-7
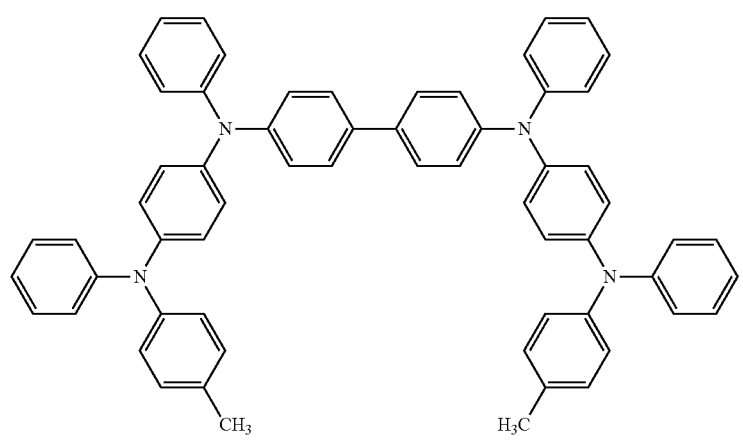

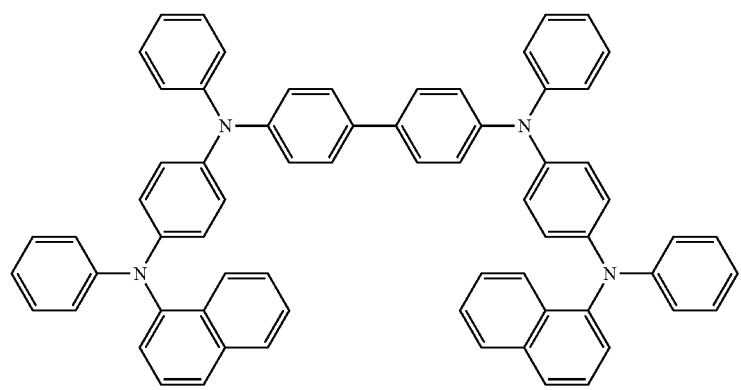
HTL-8
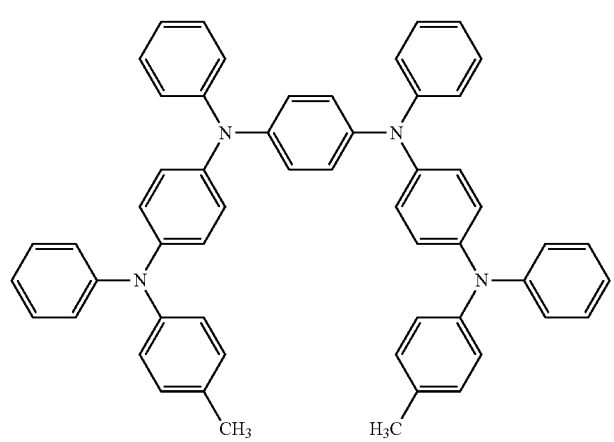
HTL-9
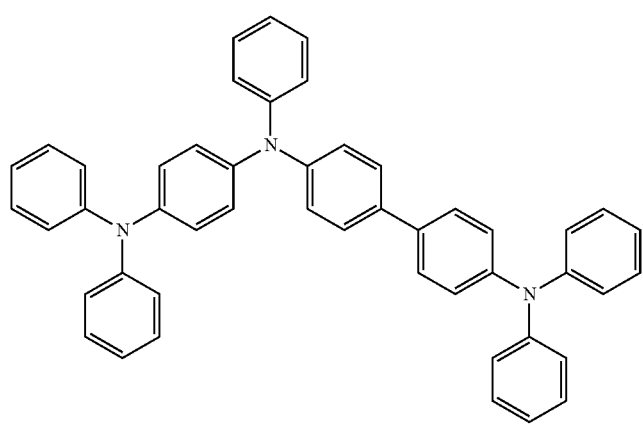
HTL-10

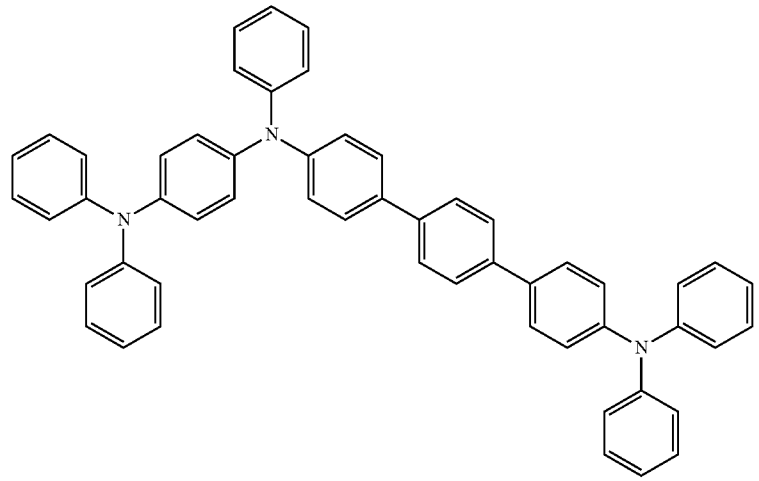
HTL-11
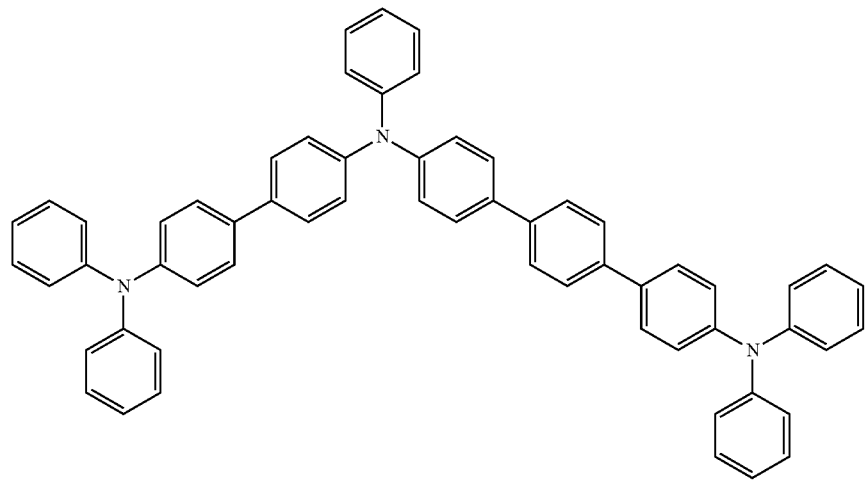
HTL-12
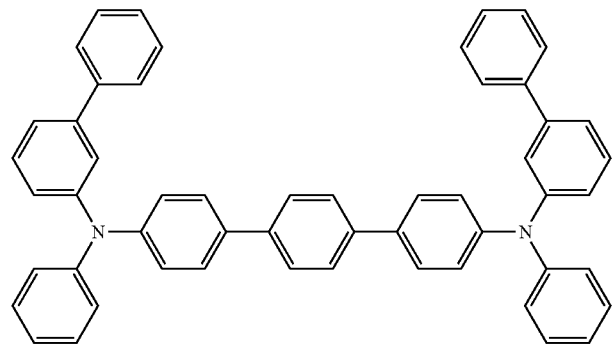
HTL-13

HTL-14

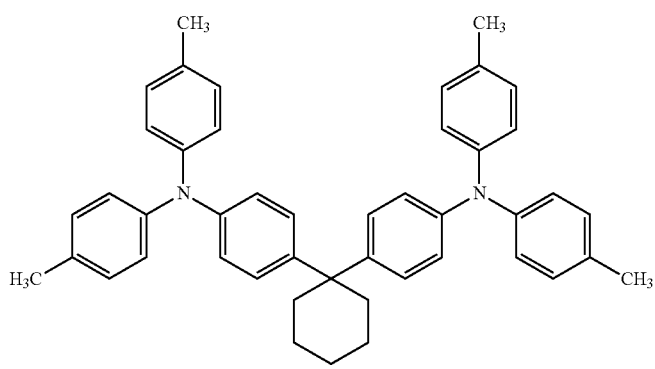

HTL-15

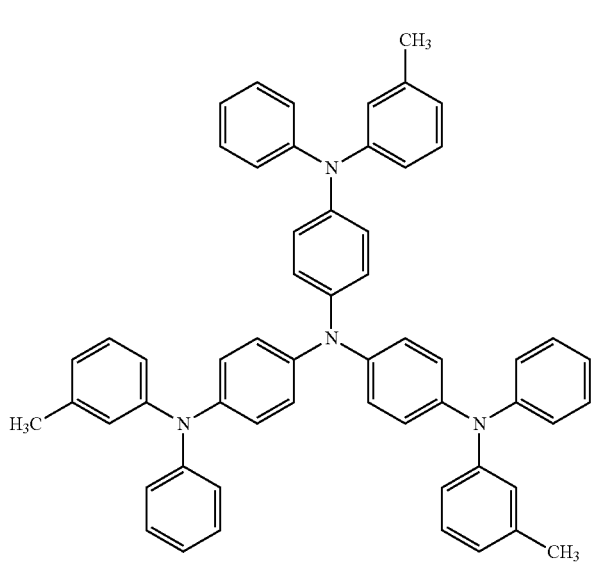

The average thickness of such a hole transport layer 5 is not limited. It is preferably on the order of 5 nm to 90 nm, more preferably on the order of 10 nm to 70 nm.

Light-Emitting Layer

The light-emitting layer 6 emits light when electric current flows between the anode 3 and the cathode 9 both described above.

Such a light-emitting layer 6 contains a light-emitting material.

An important feature of the light-emitting layer 6 is that the light-emitting material it contains is a thiadiazole having basic skeleton (1), (2), or (3) in the molecule (hereinafter also simply referred to as a thiadiazole).

(1)
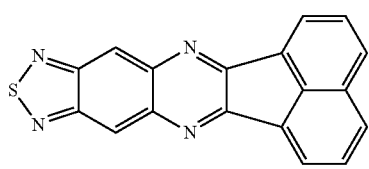

(2)
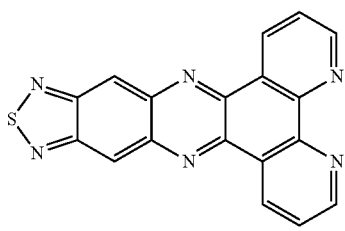

(3)
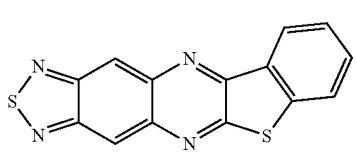

Such a thiadiazole allows the light-emitting layer 6 to emit light having a wavelength of 700 nm or more (near-infrared light).

Preferably, the light-emitting material used in the light-emitting layer 6 is compound (4) when it has basic skeleton (1), compound (5) when it has basic skeleton (2), or compound (6) when it has basic skeleton (3). This leads to more efficient and prolonged light emission. More preferably, the light-emitting material is compound (7), (8), or (9) when compound (4) is chosen. Likewise, the compound (5) is more preferably compound (10), (11), or (12), and compound (6) is more preferably compound (13), (14), or (15). More specific examples of preferred compounds are formulae D1-1 to D1-9, D2-1 to D2-3, and D3-1 to D3-3.

(4)

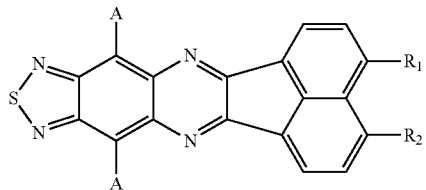

(5)

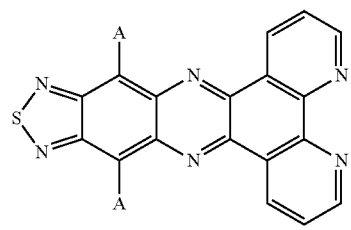

(6)

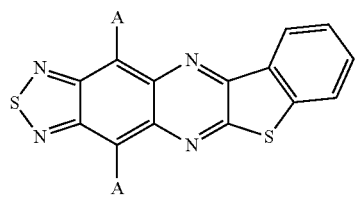

In formulae (4), (5), and (6), each A independently represents a hydrogen atom, an alkyl group, or a substituted or unsubstituted aryl group, aryl amino group, or triarylamine. Each of $R_1$ and $R_2$ independently represents a hydrogen atom, an alkyl group, or a substituted or unsubstituted aryl group, and $R_1$ and $R_2$ may be the same or different.

(7)

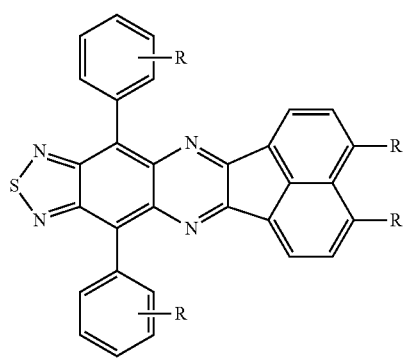

(8)

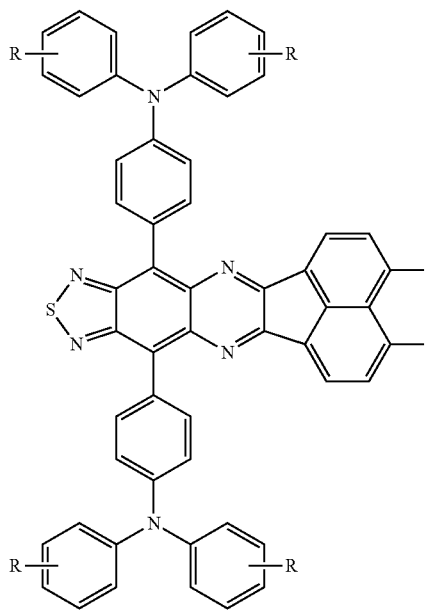

(9)

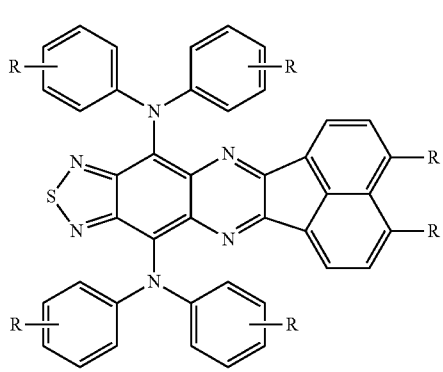

(10)

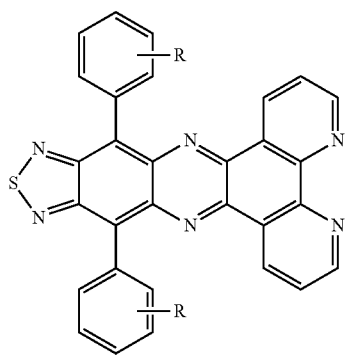

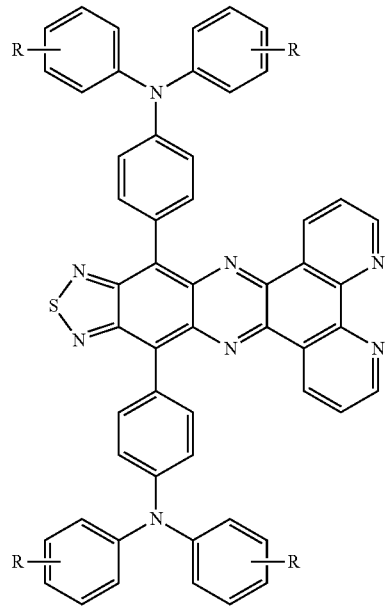
(11)
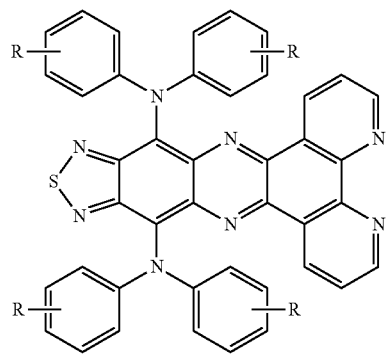
(12)
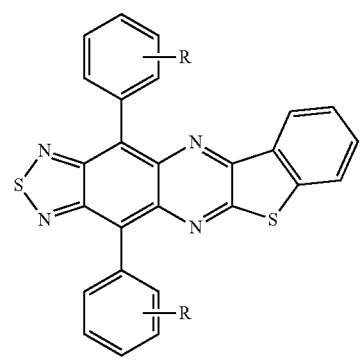
(13)
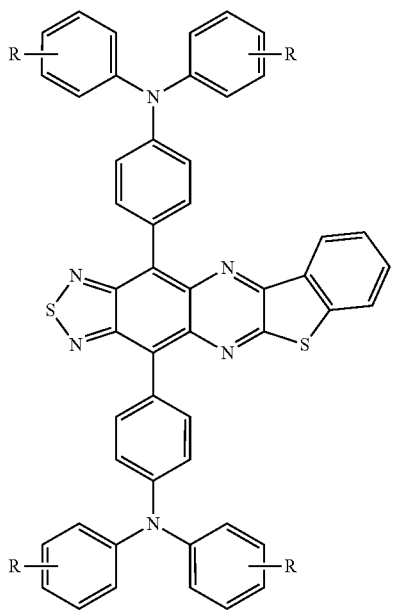
(14)
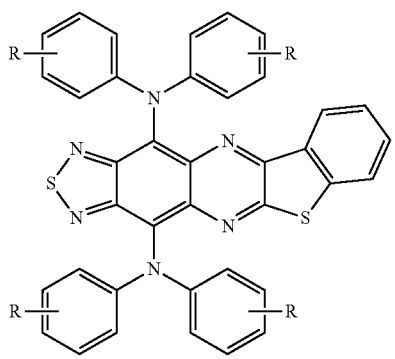
(15)
In formulae (7) to (15), each R independently represents a hydrogen atom, an alkyl group, or a substituted or unsubstituted aryl group. There may be a ring formed by a carbon linkage between two adjacent R's.
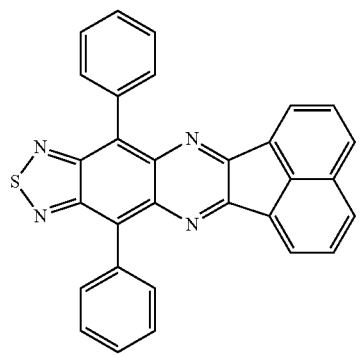
D1-1

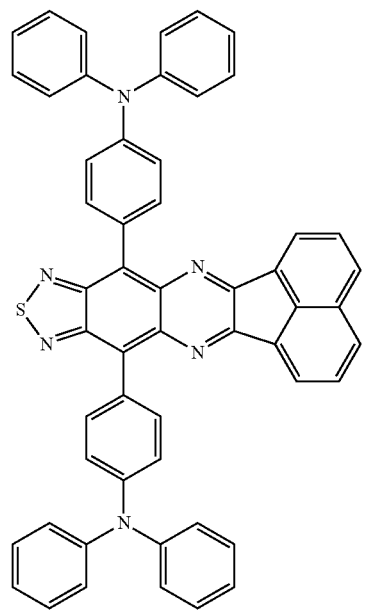
D1-2
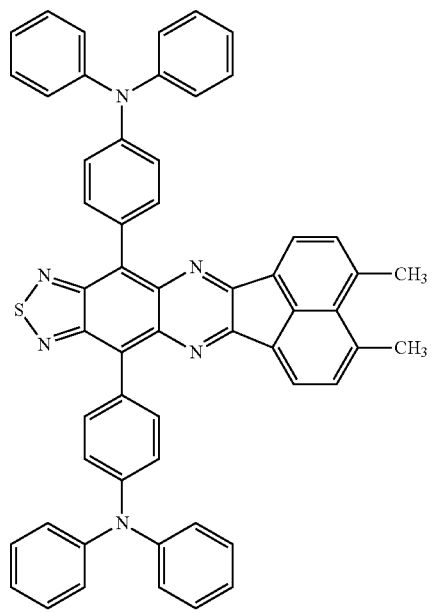
D1-5
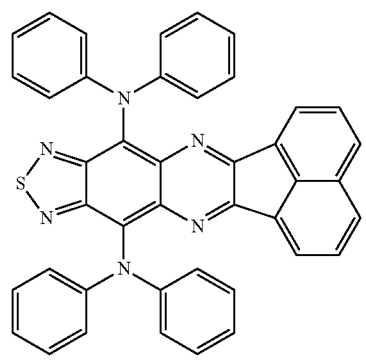
D1-3
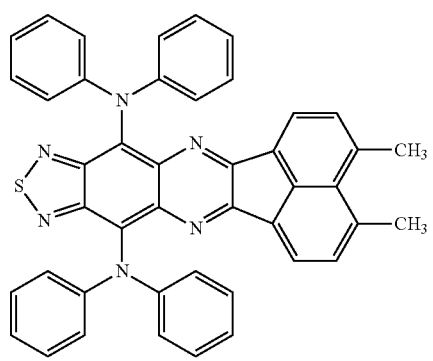
D1-6
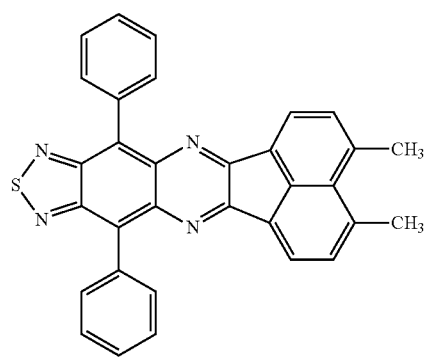
D1-4
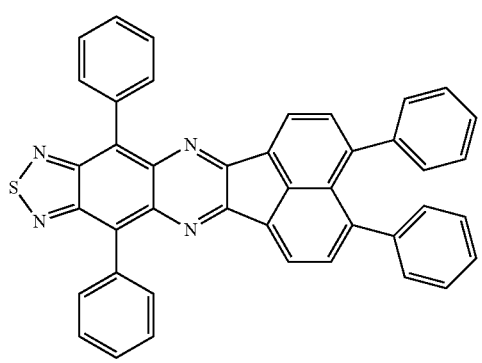
D1-7

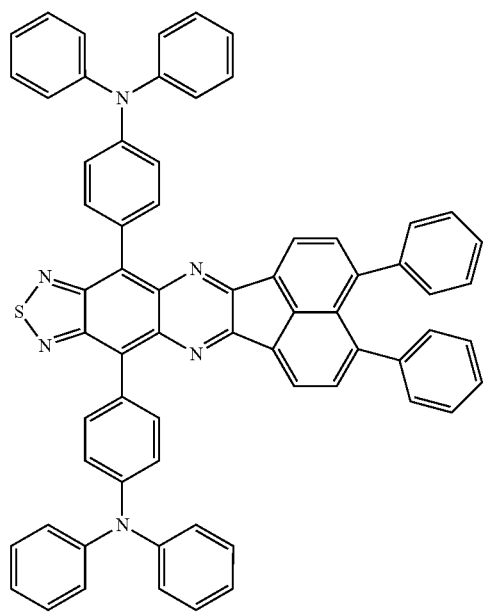
D1-8
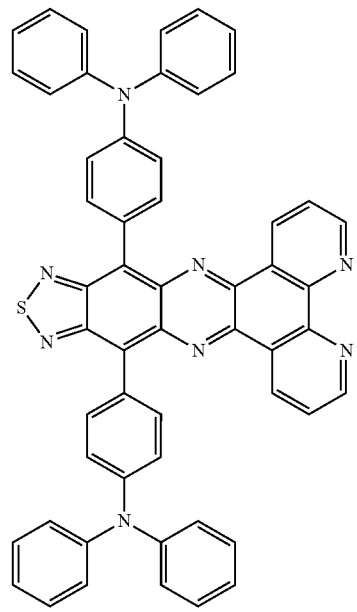
D2-2
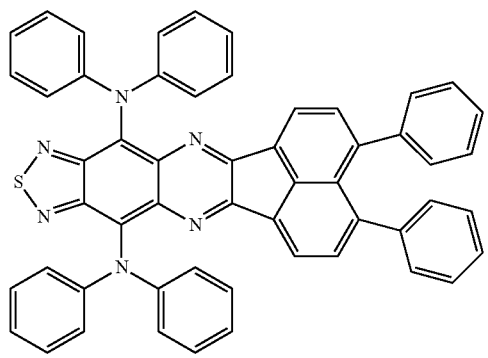
D1-9
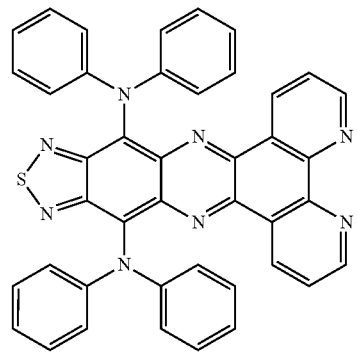
D2-3
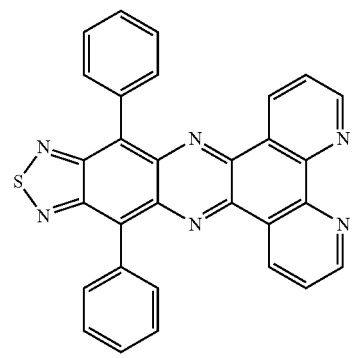
D2-1
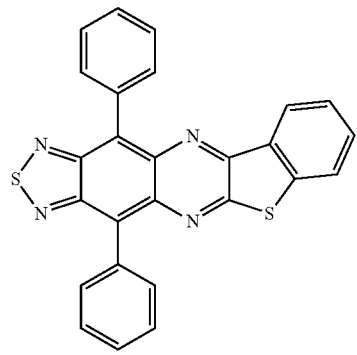
D3-1

-continued

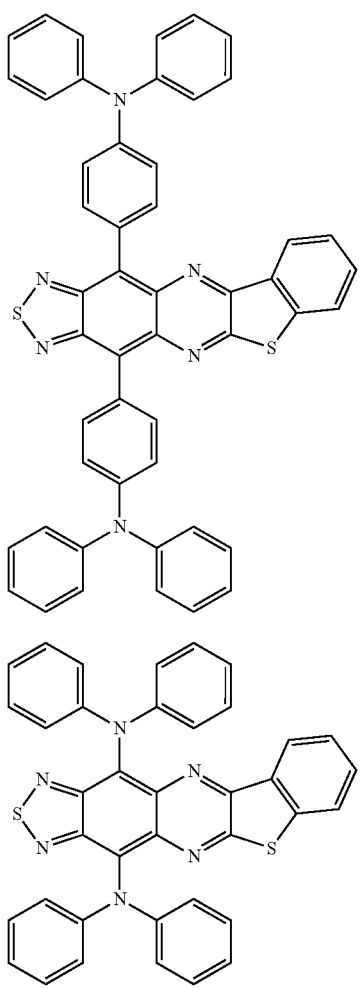

D3-2

D3-3

Other light-emitting materials (e.g., fluorescent or phosphorescent materials) may also be contained in the light-emitting layer 6.

Besides such a light-emitting material (a thiadiazole), the light-emitting layer 6 contains a host material which can be doped with (or can carry) the light-emitting material as a guest material (a dopant). The host material makes holes and electrons recombine and generate excitons, and transfers the energy of the excitons to the light-emitting material (by Förster energy transfer or Dexter energy transfer) to excite the light-emitting material. This ensures that the compound containing basic skeleton (1), (2), or (3) in the molecule is excited efficiently, and the light emission efficiency of the light-emitting element 1 is improved. This type of host material can be used by, for example, doping the host material with its guest material, i.e., the light-emitting material, as a dopant.

Such a host material may be of any kind that has effects such as the above on the light-emitting material. Examples include distyrylarylene derivatives, acene-based materials such as naphthacene derivatives and anthracene derivatives, perylene derivatives, distyrylbenzene derivatives, distyrylamine derivatives, quinolinolato metal complexes such as bis(2-methyl-8-quinolinolato)(p-phenylphenolato) aluminum (BAlq) and tris(8-quinolinolato)aluminum complex (Alq$_3$), triarylamine derivatives such as triphenylamine tetramer, oxadiazole derivatives, rubrene and its derivatives, silole derivatives, dicarbazole derivatives, oligothiophene derivatives, benzopyran derivatives, triazole derivatives, benzoxazole derivatives, benzothiazole derivatives, quinoline derivatives, and carbazole derivatives such as 4,4'-bis (2,2'-diphenylvinyl)biphenyl (DPVBi), 3-phenyl-4-(1'-naphthyl)-5-phenylcarbazole, and 4,4'-N,N'-dicarbazolebiphenyl (CBP). One or a combination of two or more of such materials can be used.

Preferably, the host material is an acene-based material or a quinolinolato metal complex, more preferably an acene-based material.

Acene-based materials are unlikely to undergo the above-described type of unwanted interactions with the light-emitting material. Furthermore, acene-based host materials (in particular, anthracene- or tetracene-based ones) can efficiently transfer energy to the light-emitting material.

This appears to be because: (a) energy transfer from the triplet excited state of the acene-based material induces the singlet excited state of the light-emitting material; (b) the overlap between the π electron cloud of the acene-based material and the electron cloud of the light-emitting material is large; and (c) the overlap between the emission spectrum of the acene-based material and the absorption spectrum of the light-emitting material is large, for example.

For such reasons, the use of an acene-based host material improves the light emission efficiency of the light-emitting element 1.

Acene-based materials are also highly resistant to electrons and holes and have excellent thermal stability, thereby allowing the light-emitting element 1 to operate for a longer period of time. When the light-emitting layer 6 is formed by a gas-phase deposition process, the excellent thermal stability of the acene-based host material protects the host material from decomposition by heat during the film formation process. This ensures the excellent film quality of the light-emitting layer 6, which also contributes to better light emission efficiency and an extended life of the light-emitting element 1.

Furthermore, acene-based materials themselves are unlikely to emit light, and this feature helps prevent the host material from affecting the emission spectrum of the light-emitting element 1.

Such an acene-based material may be of any kind that contains an acene skeleton and has effects such as the above. Examples include naphthalene derivatives, anthracene derivatives, naphthacene derivatives (tetracene derivatives), and pentacene derivatives, and one of a combination of two or more of such materials can be used. Preferably, the acene-based material is anthracene-based one (an anthracene derivative) or tetracene-based one (a tetracene derivative), more preferably tetracene-based one.

When a tetracene-based material is used, the tetracene-based material may be of any kind that has at least one tetracene skeleton in the molecule and can perform the functions of a host material such as those described above. For example, the tetracene-based material is preferably compound IRH-1, more preferably compound IRH-2, and even more preferably compound IRH-3.

IRH-1

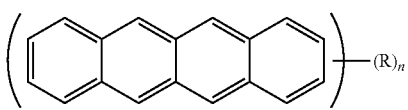

IRH-2

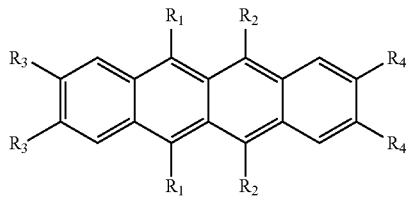

IRH-3

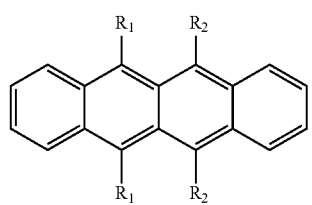

In formula IRH-1, n represents a natural number of 1 to 12, and R represents a substituent or a functional group. Each R is independently a hydrogen atom, an alkyl group, or a substituted or unsubstituted aryl or aryl amino group. In formulae IRH-2 and IRH-3, each of $R_1$ to $R_4$ independently represents a hydrogen atom, an alkyl group, or a substituted or unsubstituted aryl or aryl amino group. Some or all of $R_1$ to $R_4$ may be the same, or they may be all different.

The tetracene-based material used as the host material is preferably composed of carbon and hydrogen atoms. This prevents unwanted interactions between the host material and the light-emitting material and thus enhances the light emission efficiency of the light-emitting element 1. The resistance of the host material to electrons and holes is also increased, extending the life of the light-emitting element 1.

Specific examples of preferred tetracene-based materials include compounds H1-1 to H1-27.

H1-1

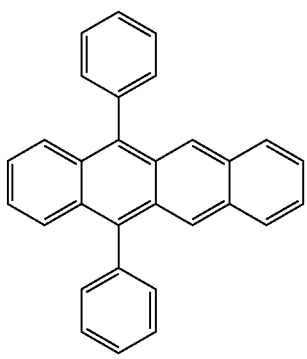

H1-2

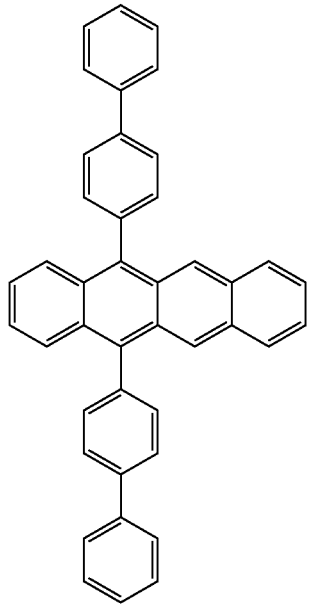

H1-3

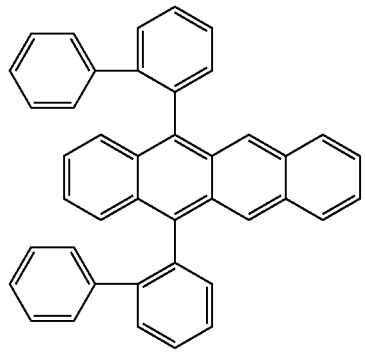

H1-4

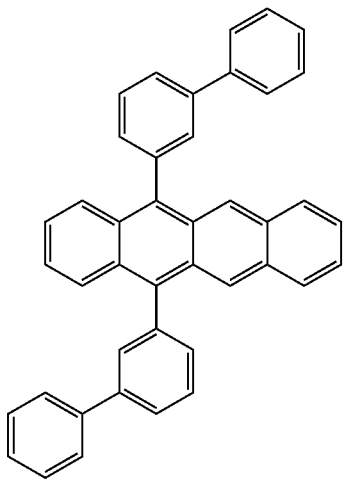

H1-5
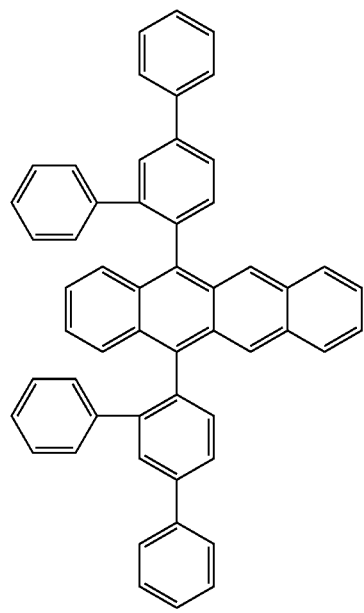
H1-6
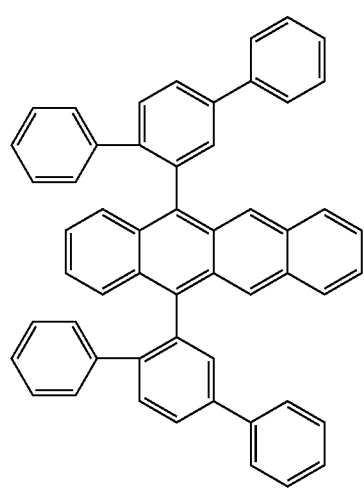
H1-7
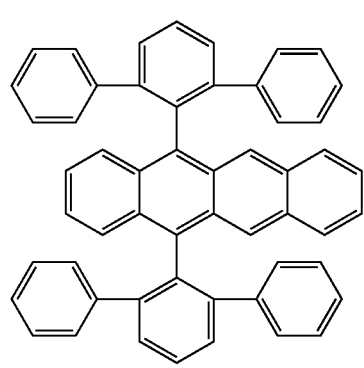
H1-8
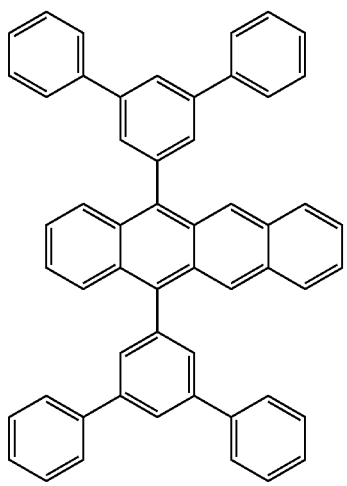
H1-9
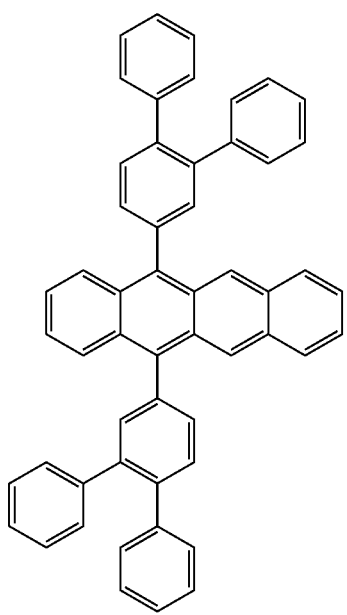

H1-10
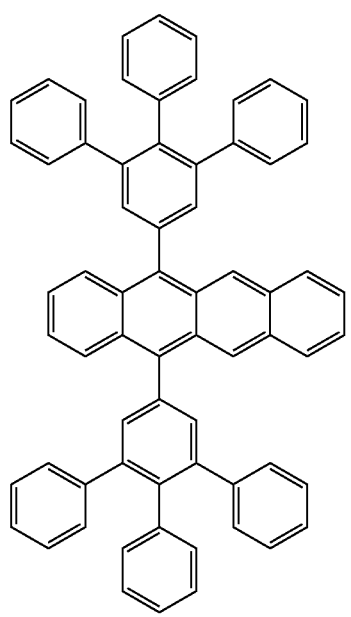
H1-11
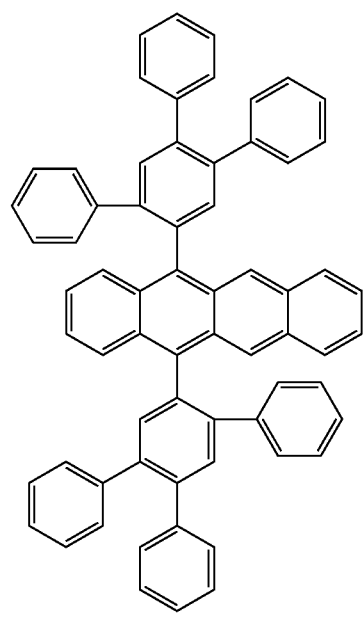
H1-12
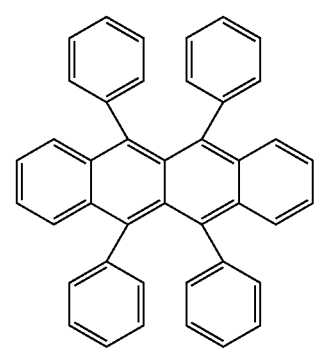
H1-13
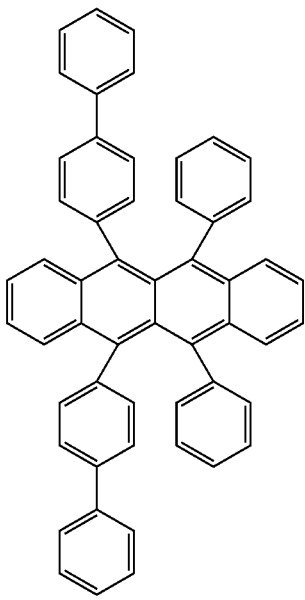
H1-14
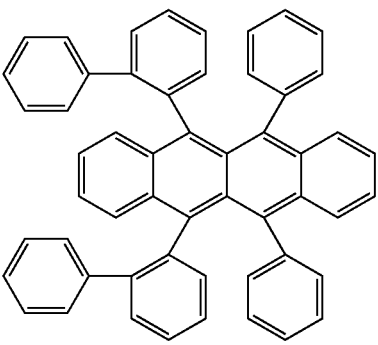
H1-15
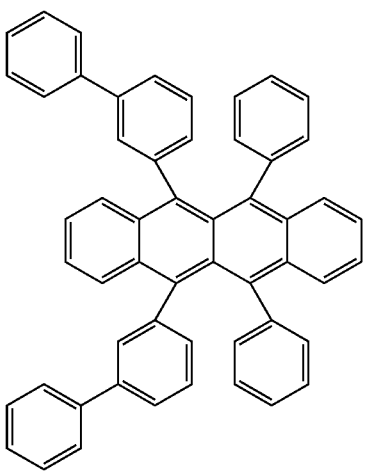

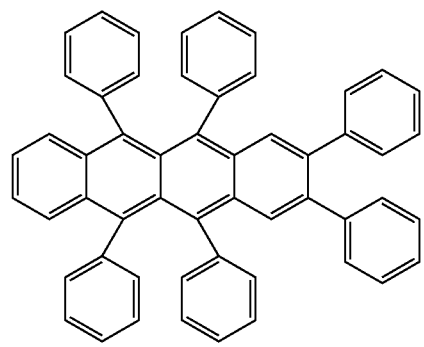
H1-16
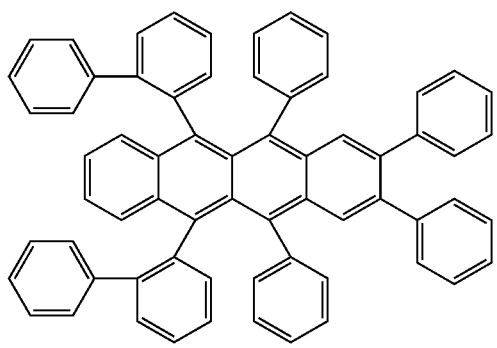
H1-19
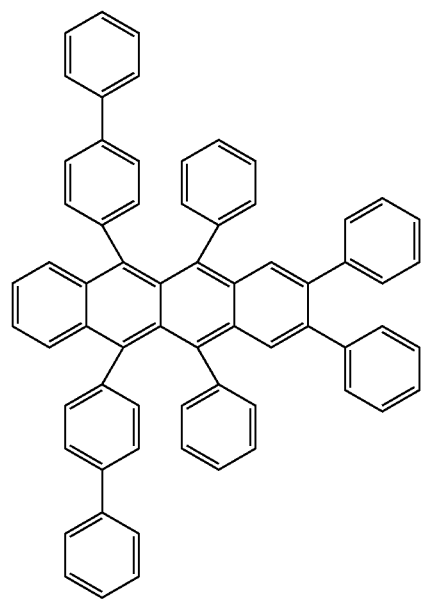
H1-17
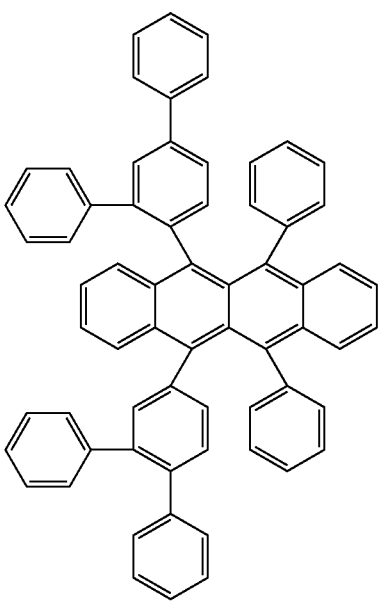
H1-20
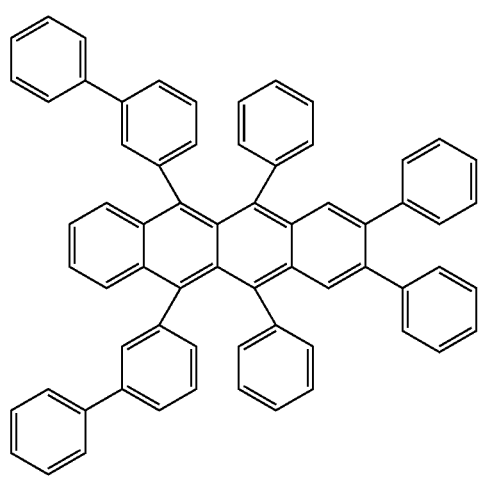
H1-18
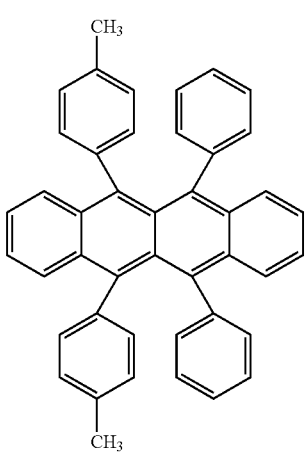
H1-21

-continued

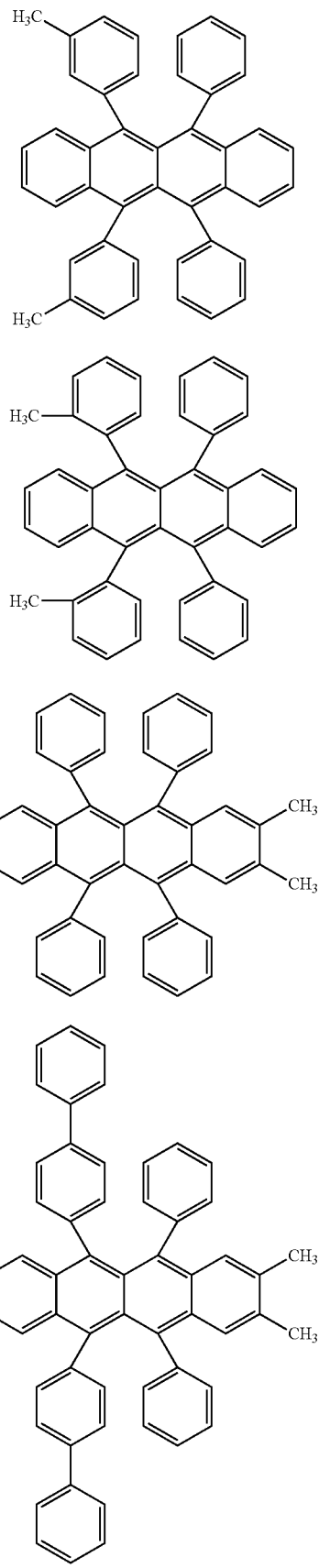

H1-22

H1-23

H1-24

H1-25

-continued

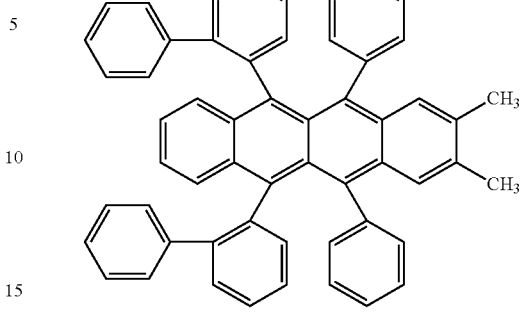

H1-26

H1-27

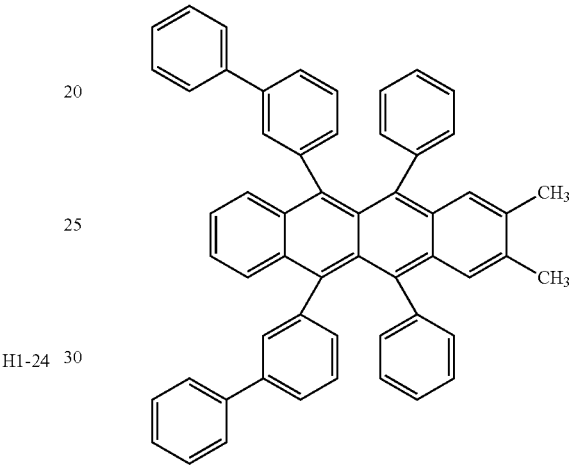

When an anthracene-based material is used, the anthracene-based material may be of any kind that has at least one anthracene skeleton in the molecule and can perform the functions of a host material such as those described above. For example, the anthracene-based material is preferably compound IRH-4, more preferably any of compounds IRH-5 to IRH-8.

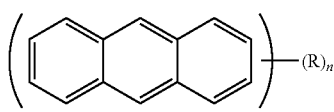

IRH-4

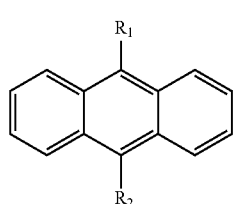

IRH-5

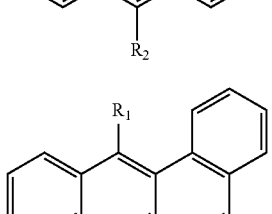

IRH-6

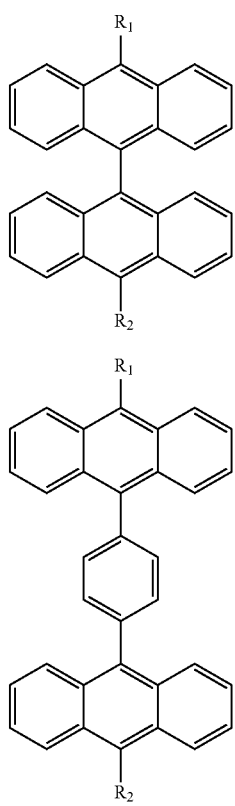

IRH-7

IRH-8

In formula IRH-4, n represents a natural number of 1 to 10, and R represents a substituent or a functional group. Each R is independently a hydrogen atom, an alkyl group, or a substituted or unsubstituted aryl or aryl amino group. In formulae IRH-5 to IRH-8, each of $R_1$ and $R_2$ independently represents a hydrogen atom, an alkyl group, or a substituted or unsubstituted aryl or aryl amino group. $R_1$ and $R_2$ may be the same or different.

The anthracene-based material used as the host material is preferably composed of carbon and hydrogen atoms. This prevents unwanted interactions between the host material and the light-emitting material and thus enhances the light emission efficiency of the light-emitting element 1. The resistance of the host material to electrons and holes is also increased, extending the life of the light-emitting element 1.

Specific examples of preferred anthracene-based materials include compounds H2-1 to H2-56.

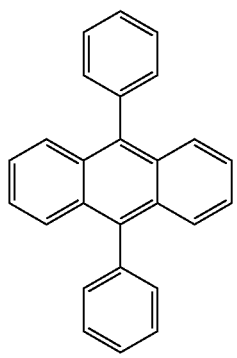

H2-1

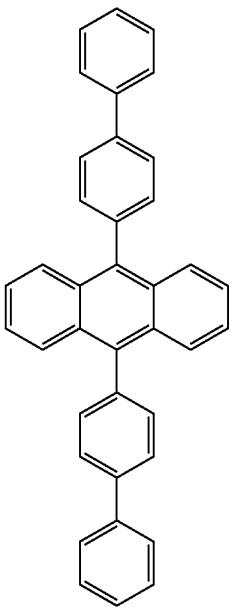

H2-2

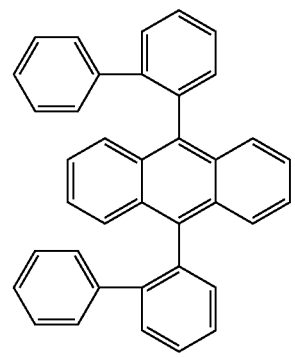

H2-3

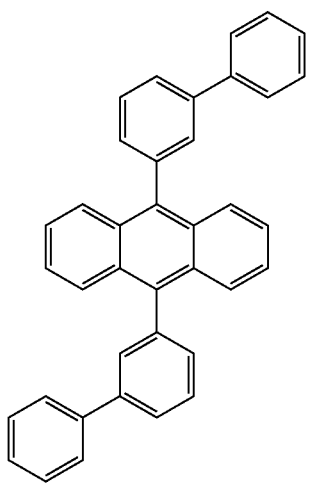

H2-4

-continued
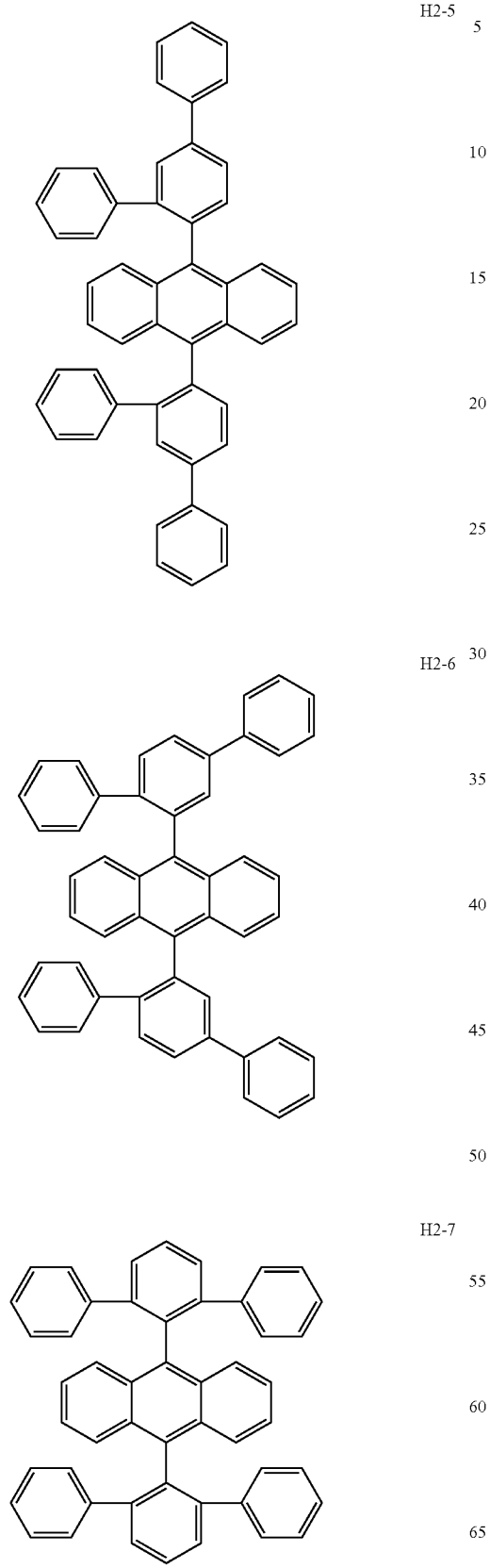
H2-5
H2-6
H2-7
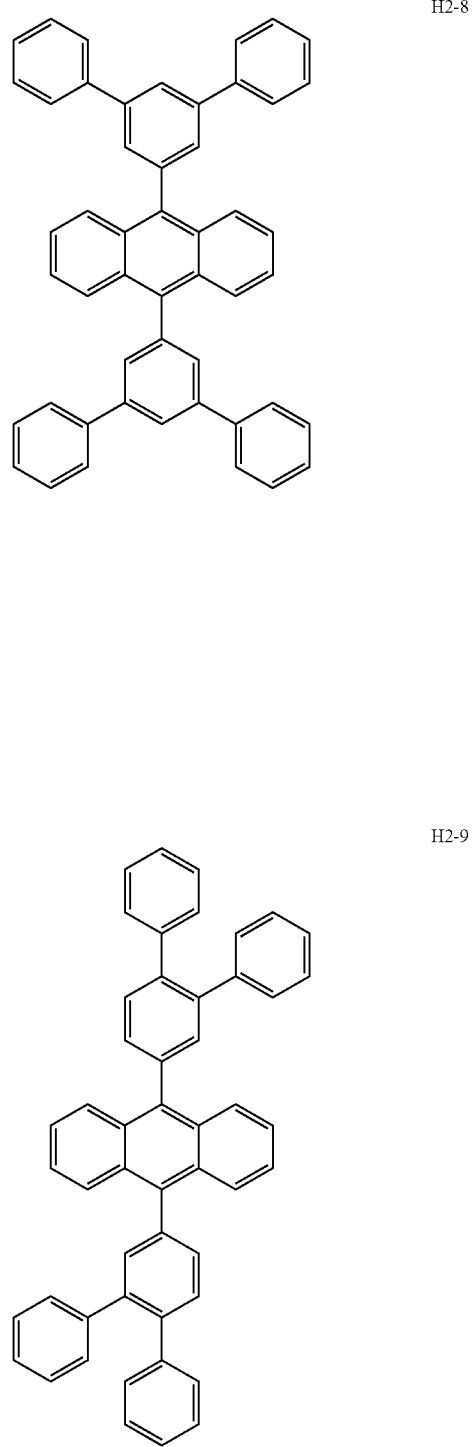
H2-8
H2-9

H2-10
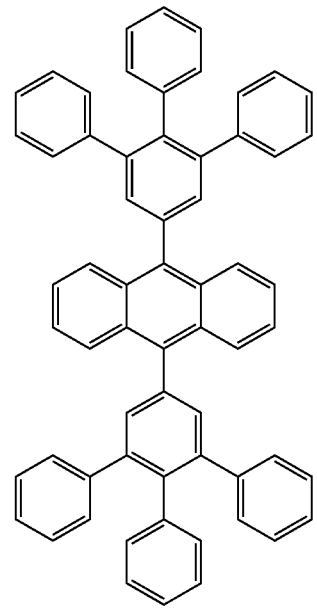
H2-11
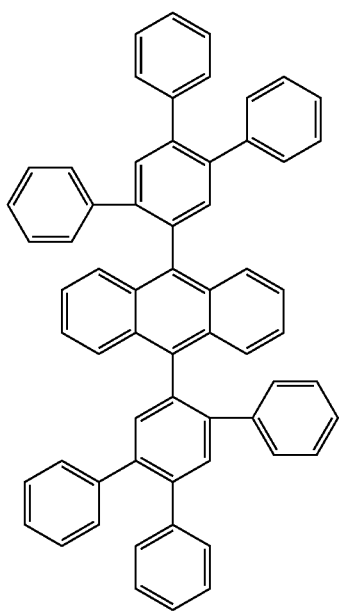
H2-12
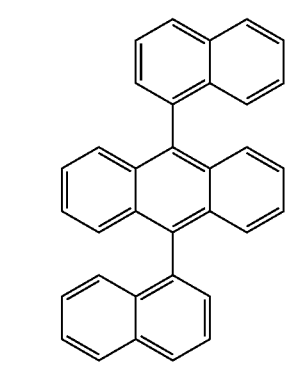
H2-13
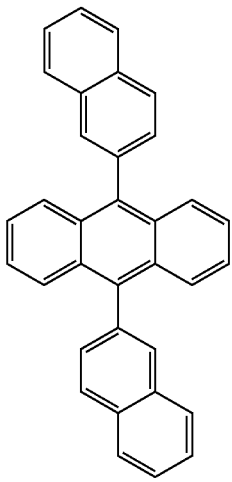
H2-14
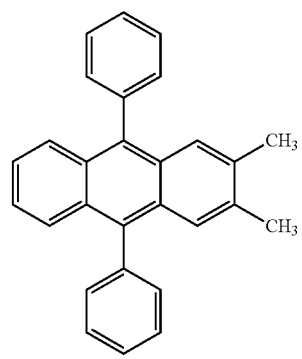
H2-15
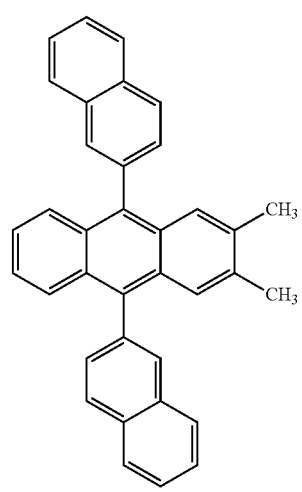

H2-16
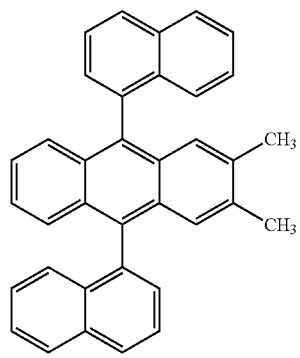
H2-17
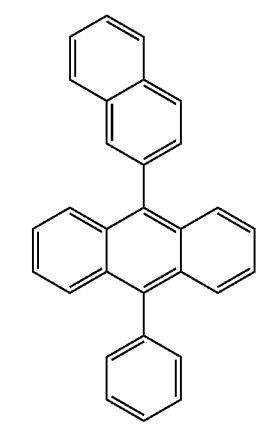
H2-18
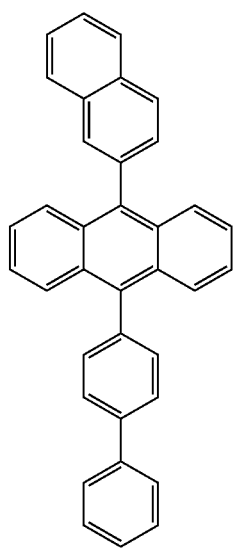
H2-19
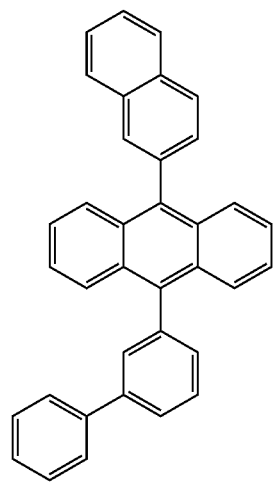
H2-20
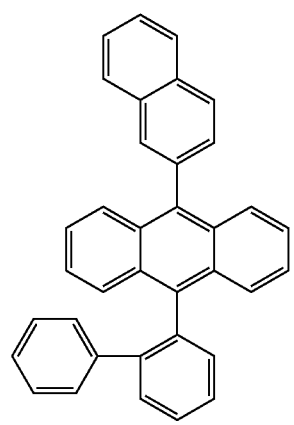
H2-21
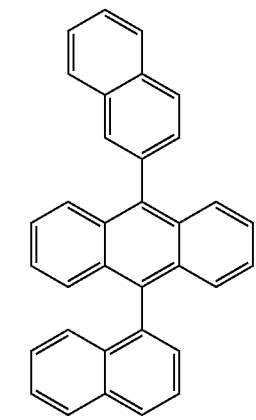

H2-22
H2-23
H2-24
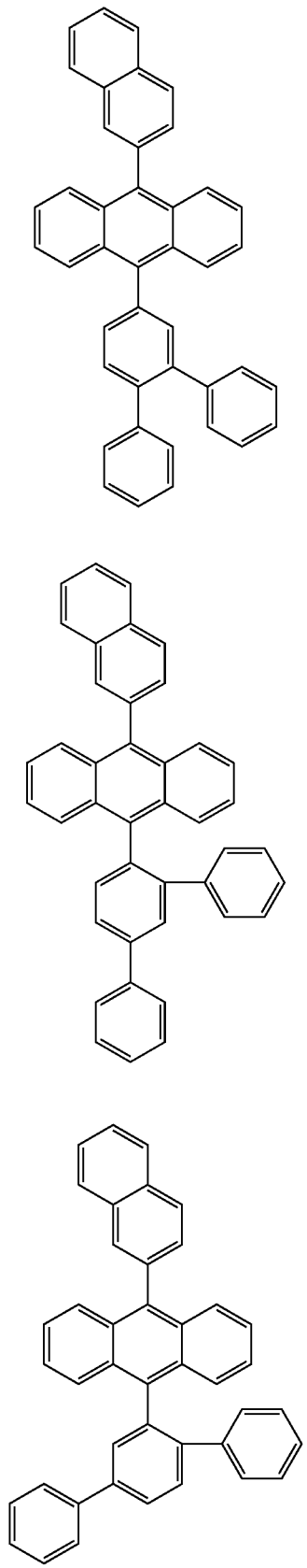
H2-25
H2-26
H2-27
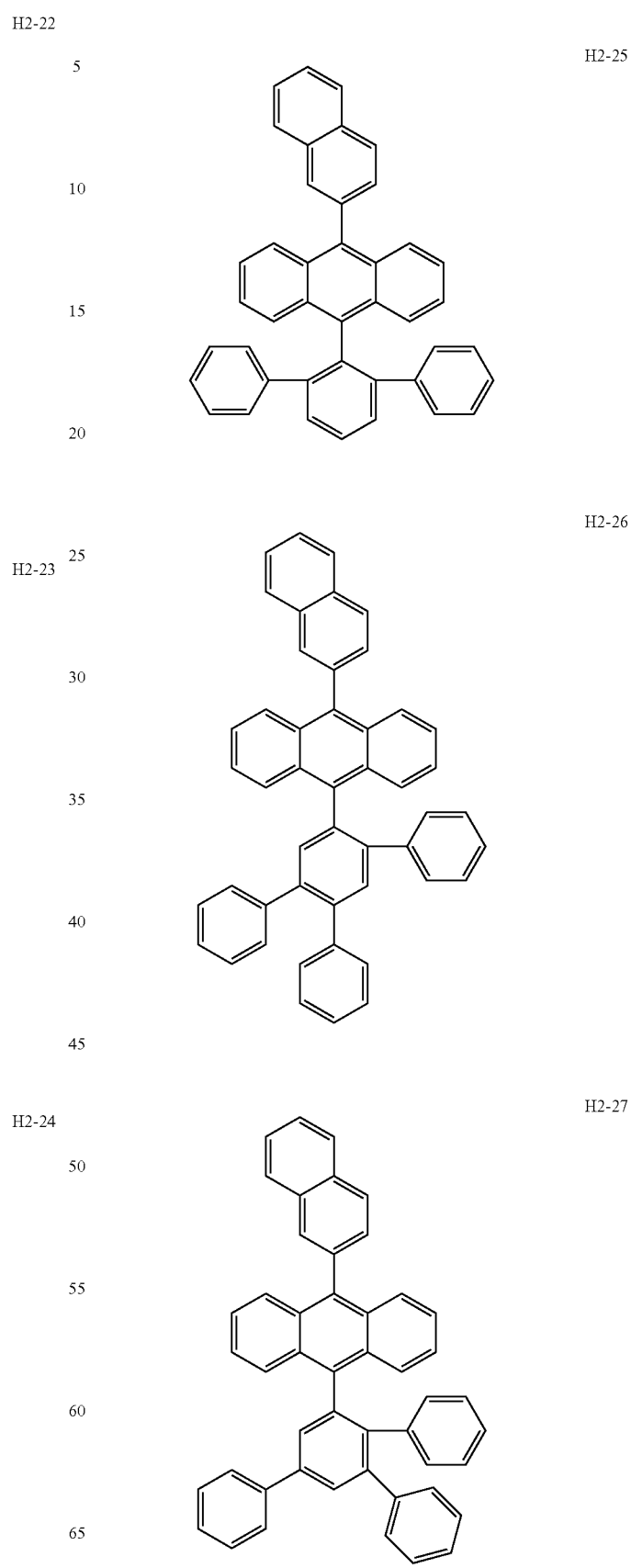

H2-28
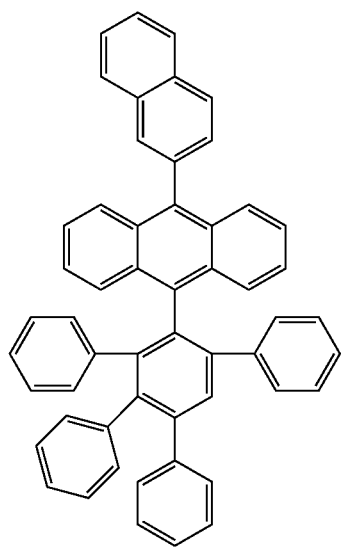
H2-30
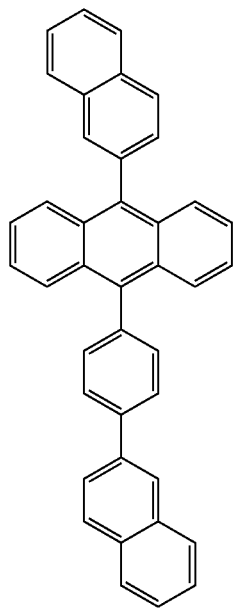
H2-29
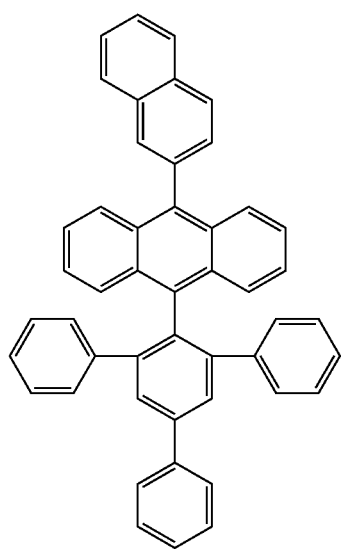
H2-31
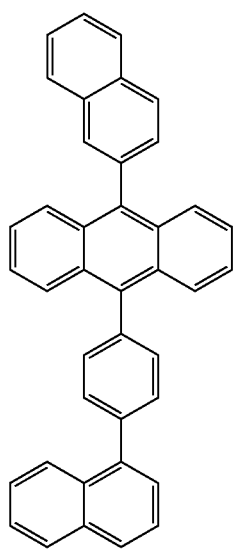

H2-32
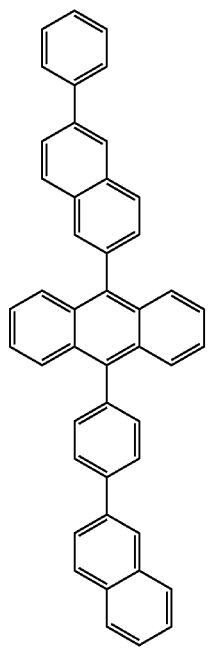
H2-34
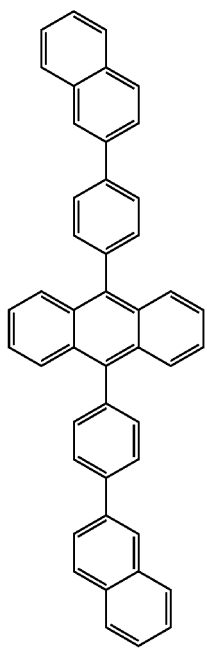
H2-33
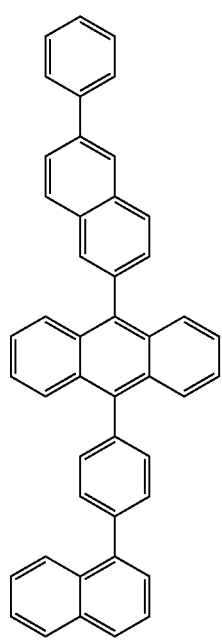
H2-35
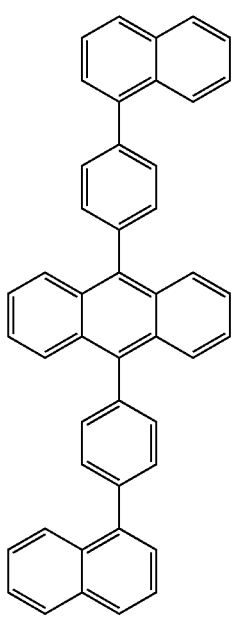

H2-36
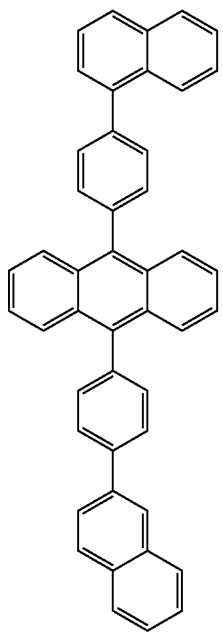
H2-37
H2-38
H2-39
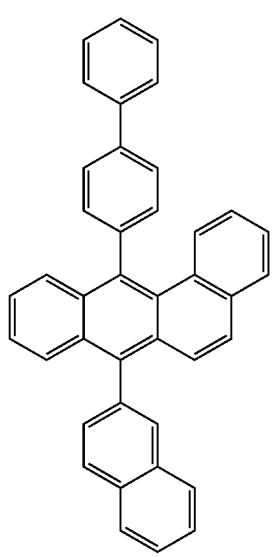
H2-40
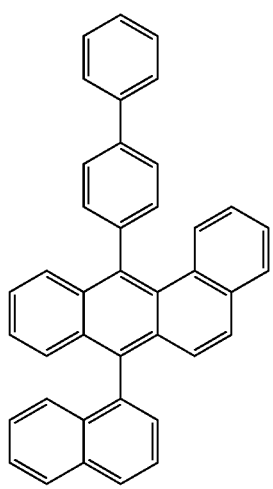
H2-41
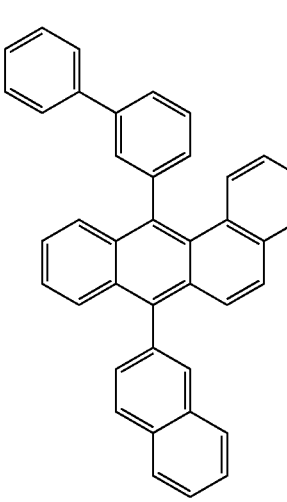

H2-42
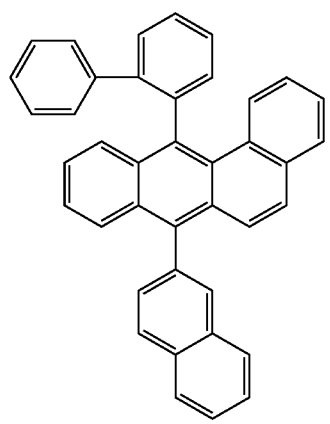
H2-43
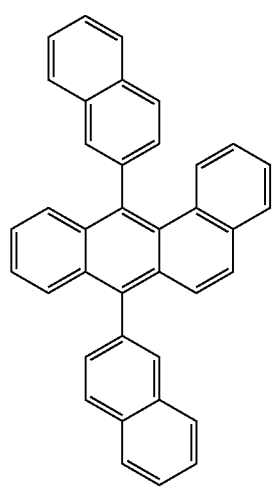
H2-44
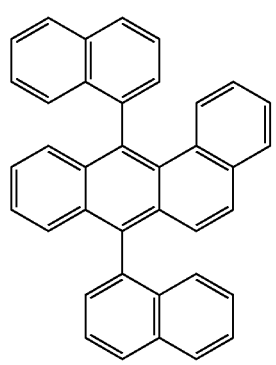
H2-45
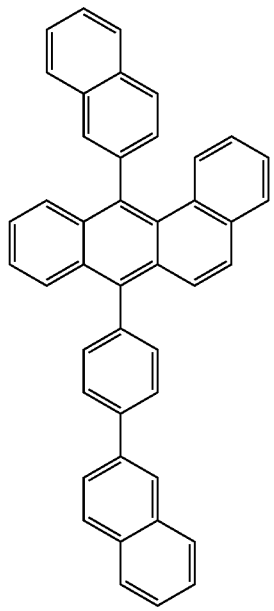
H2-46
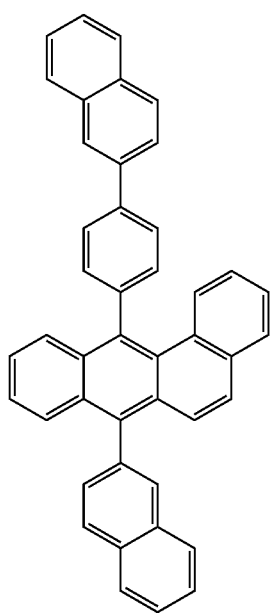

H2-47
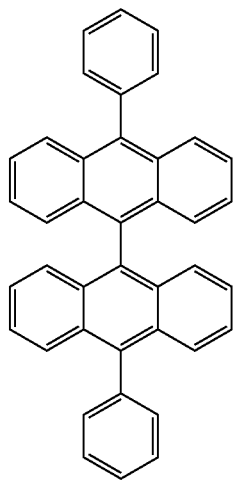
H2-48
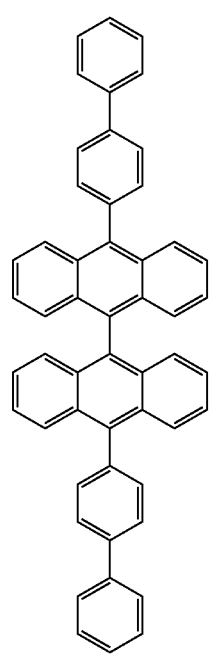
H2-49
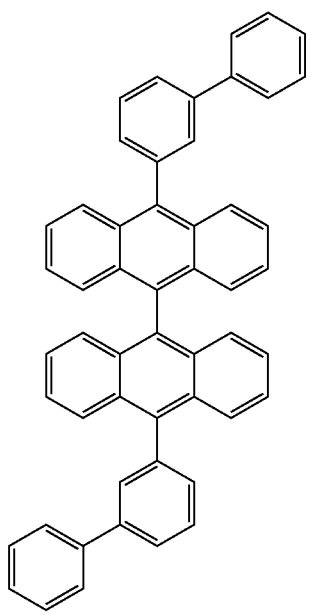
H2-50
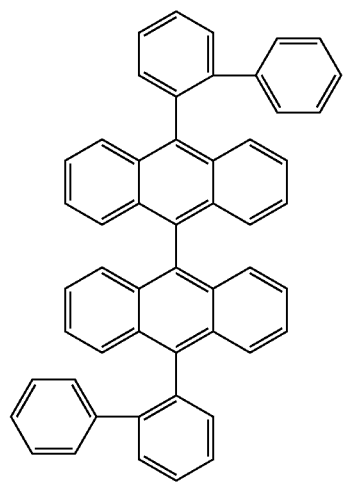

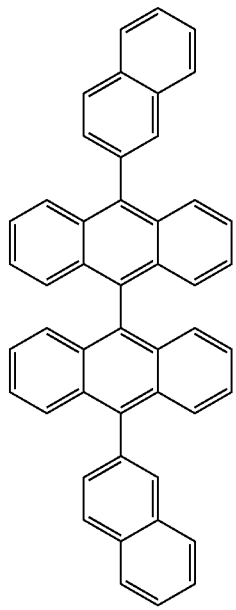
H2-51
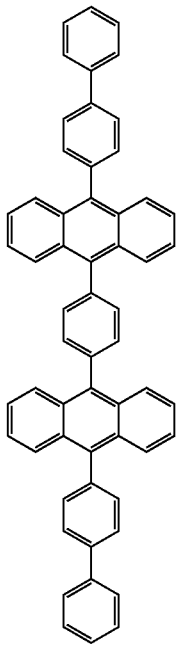
H2-53
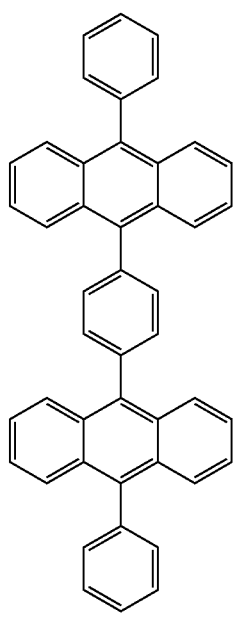
H2-52
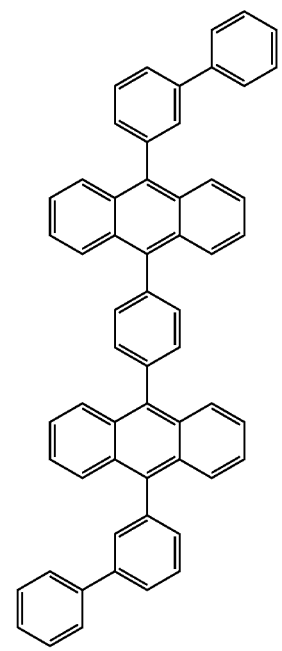
H2-54

-continued

H2-55

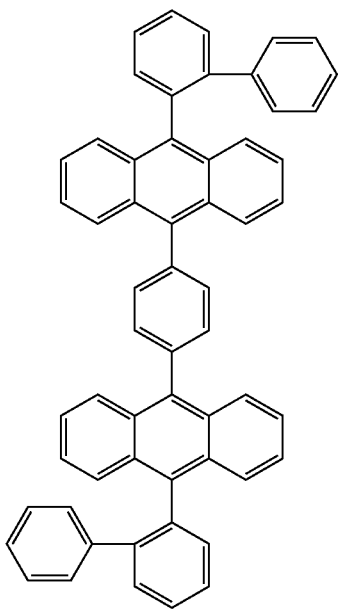

H2-56

In such a light-emitting layer 6, containing a light-emitting material and a host material, the amount of the light-emitting material (doping level) is preferably in the range of 0.01 wt % to 10 wt %, more preferably 0.1 wt % to 5 wt %. The light emission efficiency is optimized when the light-emitting material content falls within such a range.

The average thickness of the light-emitting layer 6 is not limited. It is preferably on the order of 1 nm to 60 nm, more preferably on the order of 3 nm to 50 nm.

Electron Transport Layer

The electron transport layer 7 receives the electrons injected from the cathode 9 via the electron injection layer 8 and transmits them to the light-emitting layer 6.

Examples of materials that can be used to make the electron transport layer 7 (electron transport materials) include phenanthroline derivatives such as 2,9-dimethyl-4,7-diphenyl-1,10-phenanthroline (BCP), quinoline derivatives such as organometallic complexes coordinated by 8-quinolinol or its derivative ligands, e.g., tris(8-quinolinolato)aluminum ($Alq_3$), azaindolizine derivatives, oxadiazole derivatives, perylene derivatives, pyridine derivatives, pyrimidine derivatives, quinoxaline derivatives, diphenylquinone derivatives, and nitro-substituted fluorene derivatives. One or a combination of two or more of such materials can be used.

Preferably, the electron transport material used in the electron transport layer 7 is an azaindolizine derivative, more preferably an azaindolizine-based compound having an azaindolizine skeleton and an anthracene skeleton in the molecule (hereinafter also simply referred to as an azaindolizine).

Compounds having an azaindolizine skeleton and an anthracene skeleton in the molecule, when used as the electron transport material in the electron transport layer 7, which borders the light-emitting layer 6, allow efficient transport of electrons from the electron transport layer 7 to the light-emitting layer 6, thereby imparting excellent light emission efficiency to the light-emitting element 1.

The efficient electron transport from the electron transport layer 7 to the light-emitting layer 6 lowers the driving voltage of the light-emitting element 1. This allows the light-emitting element 1 to operate for a longer period of time.

Furthermore, compounds having an azaindolizine skeleton and an anthracene skeleton in the molecule are inert (highly resistant) to electrons and holes. This also contributes to an extended life of the light-emitting element 1.

It is preferred that the electron transport material (azaindolizine) used in the electron transport layer 7 contains one or two azaindolizine skeletons and one or two anthracene skeletons per molecule. This imparts excellent electron transport and electron injection properties to the electron transport layer 7.

Specific examples of preferred azaindolizines for use in the electron transport layer 7 include compounds ETL-A1 to ETL-A24, compounds ETL-B1 to ETL-B12, and compounds ETL-C1 to ETL-C20.

ETL-A1

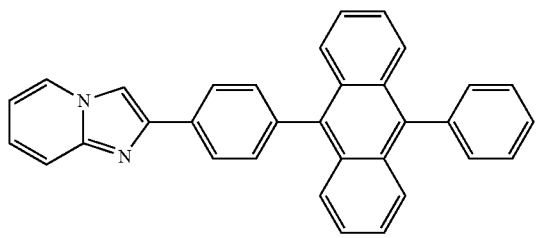

ETL-A2

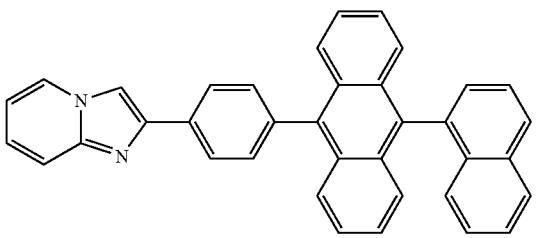

-continued
ETL-A3
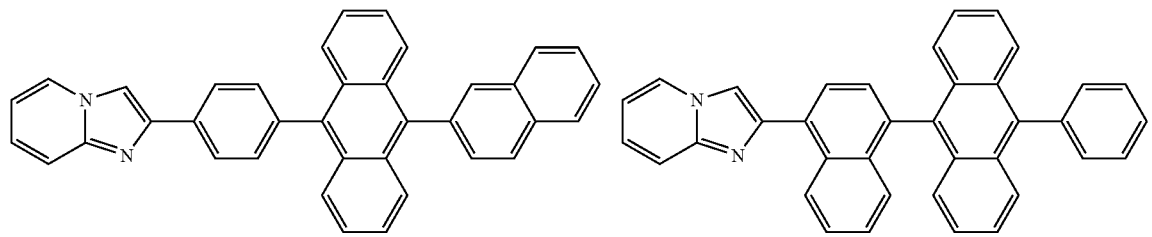
ETL-A4
ETL-A5
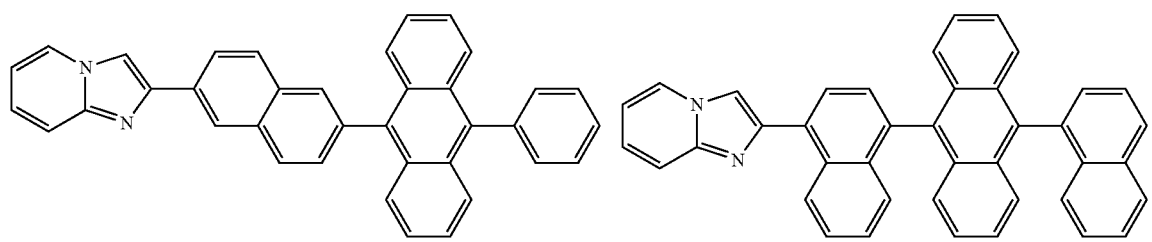
ETL-A6
ETL-A7
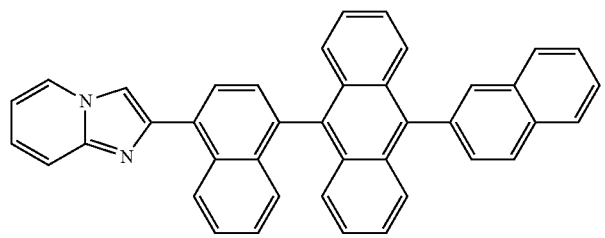
ETL-A8
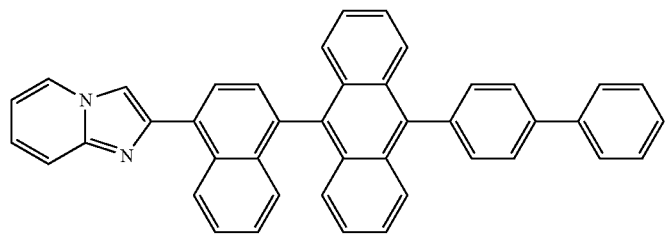
ETL-A9
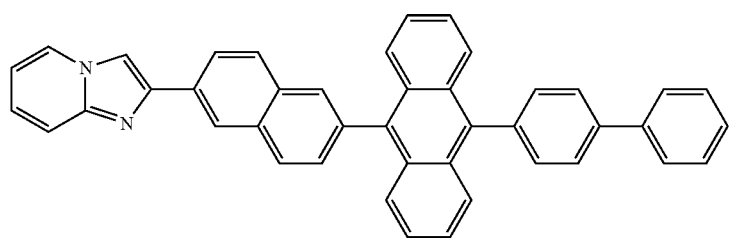
ETL-A10
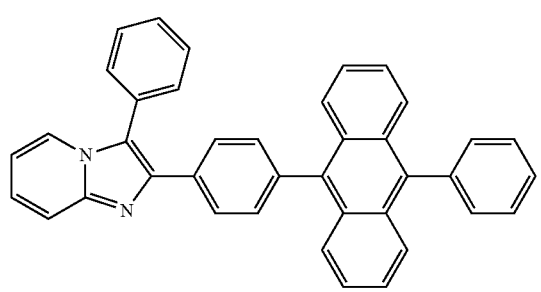
ETL-A11
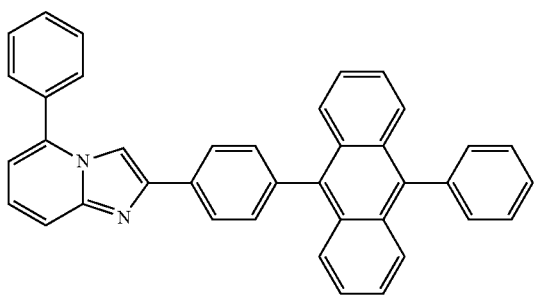

-continued
ETL-A12
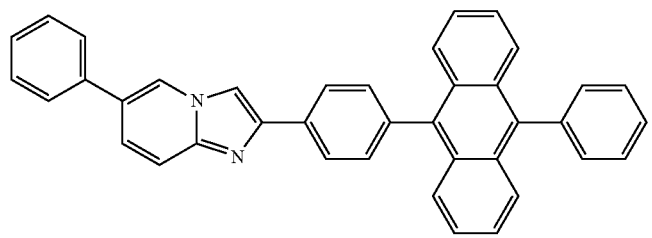
ETL-A13
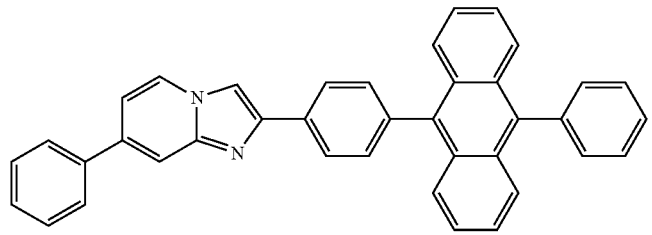
ETL-A14
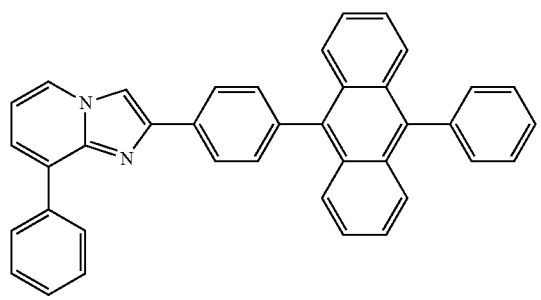
ETL-A15
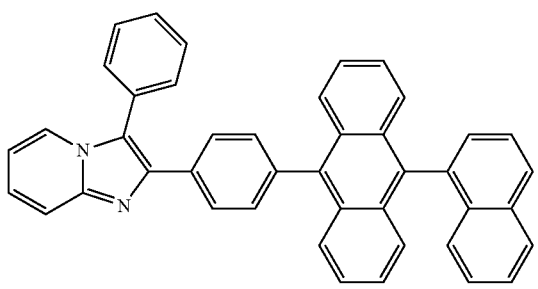
ETL-A16
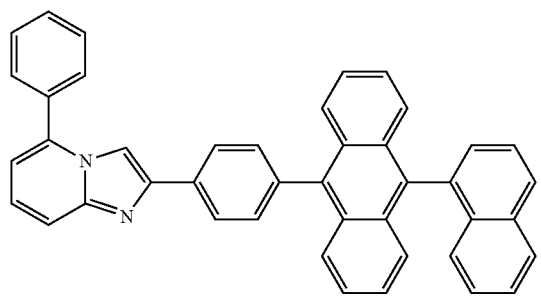
ETL-A17
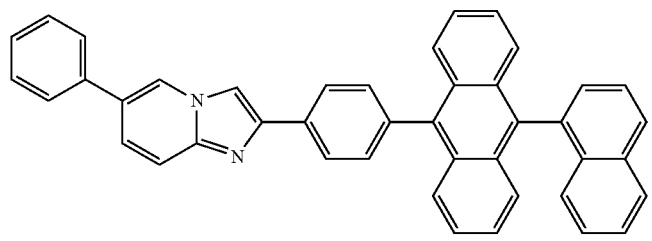
ETL-A18
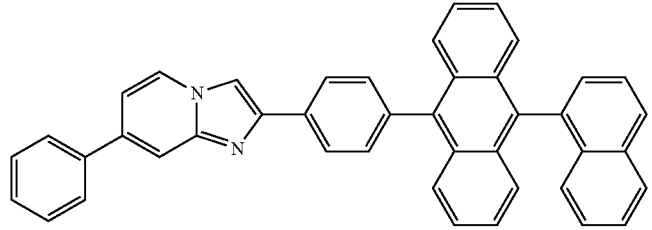

-continued
ETL-A19
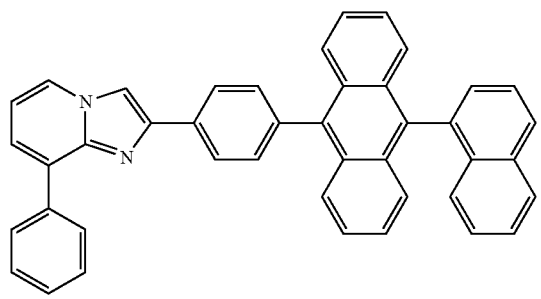
ETL-A20
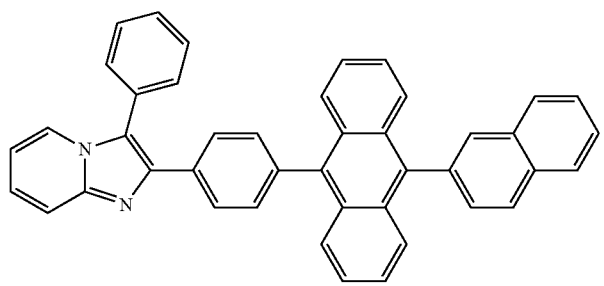
ETL-21
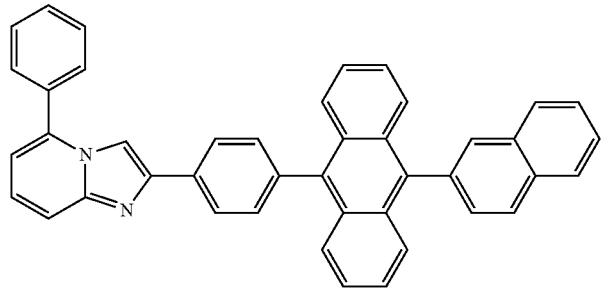
ETL-A22
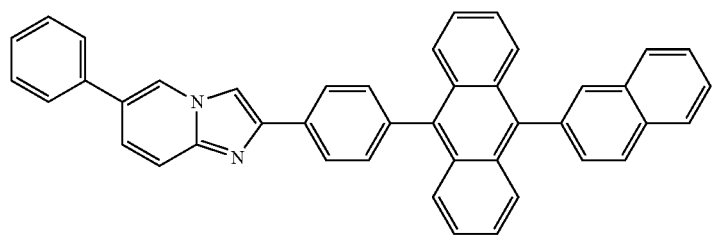
ETL-A23
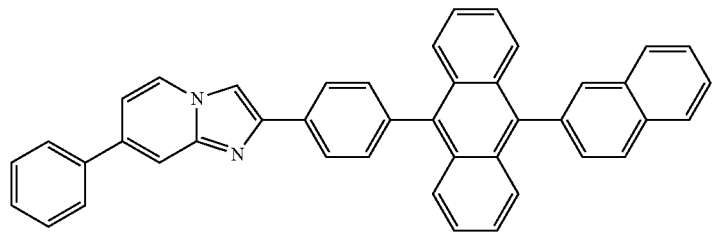
ETL-A24
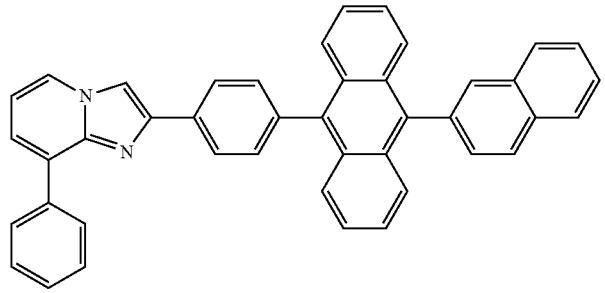
ETL-B1
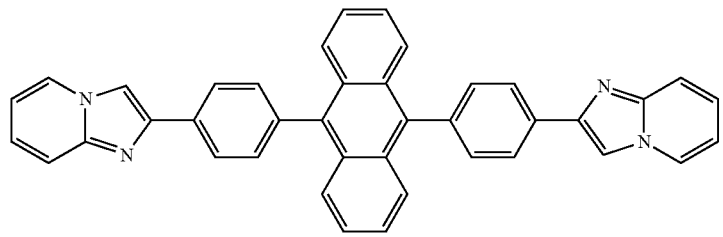

ETL-B2
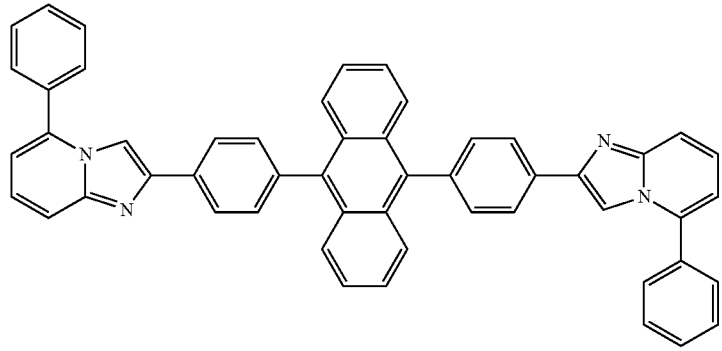
ETL-B3
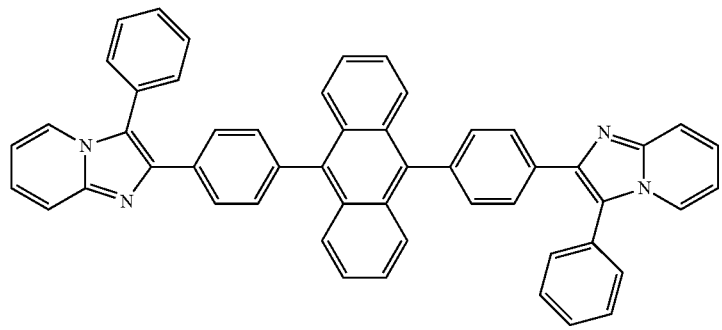
ETL-B4
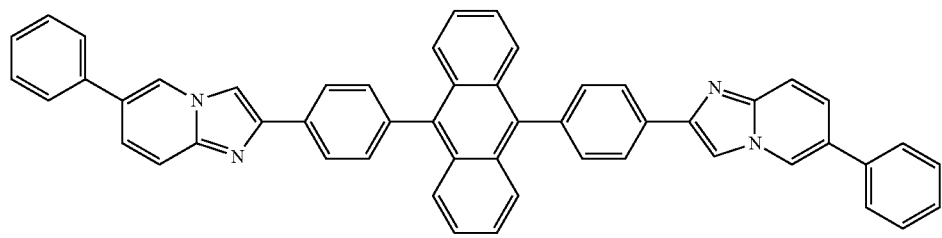
ETL-B5
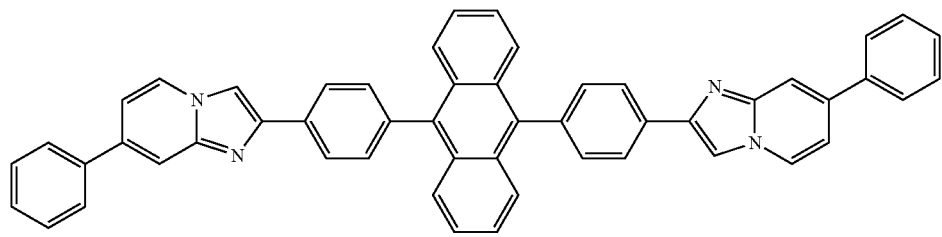
ETL-B6
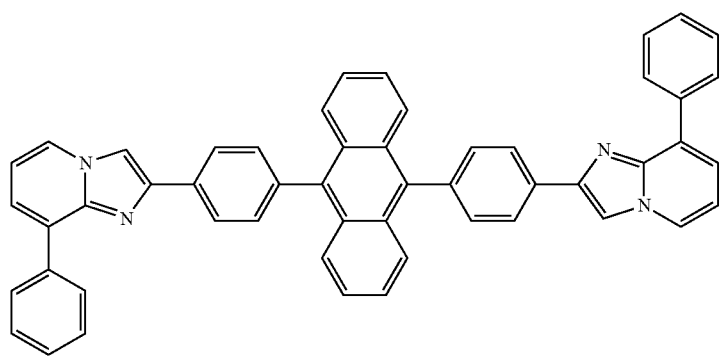

-continued
ETL-B7
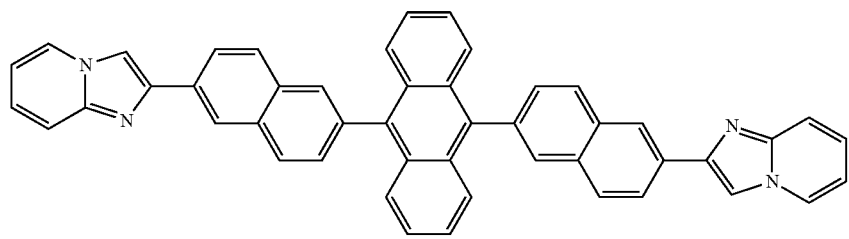
ETL-B8
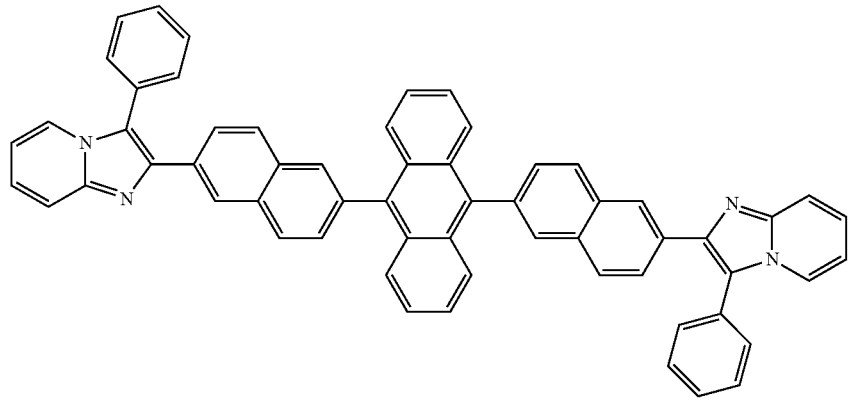
ETL-B9
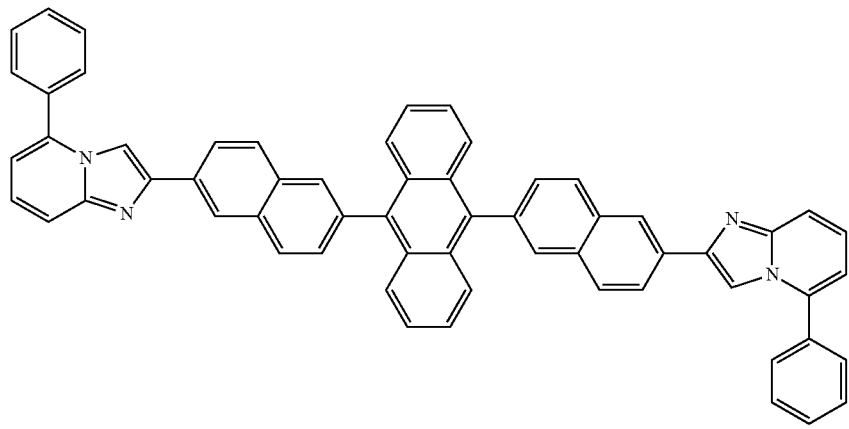
ETL-B10
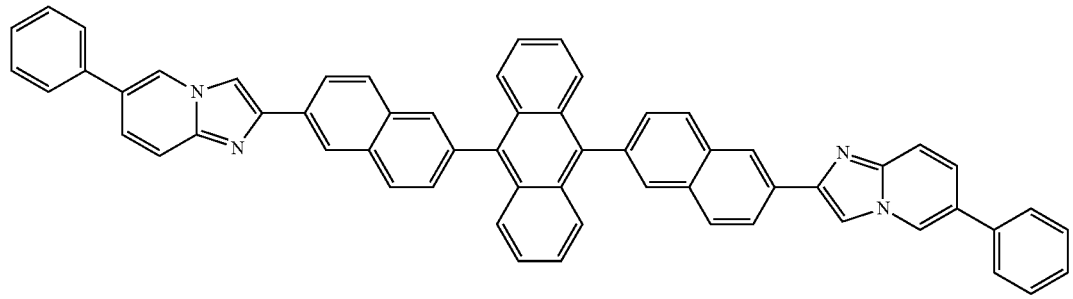
ETL-B11
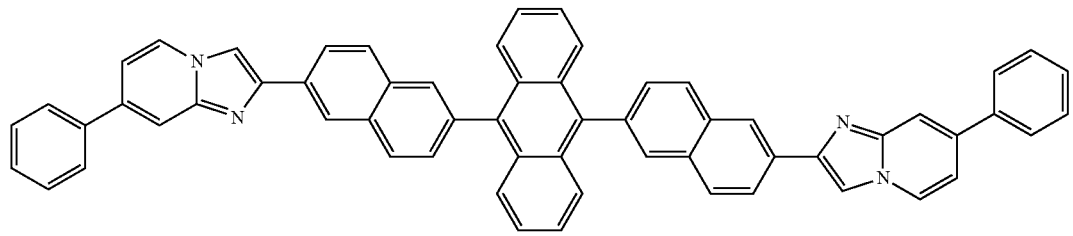

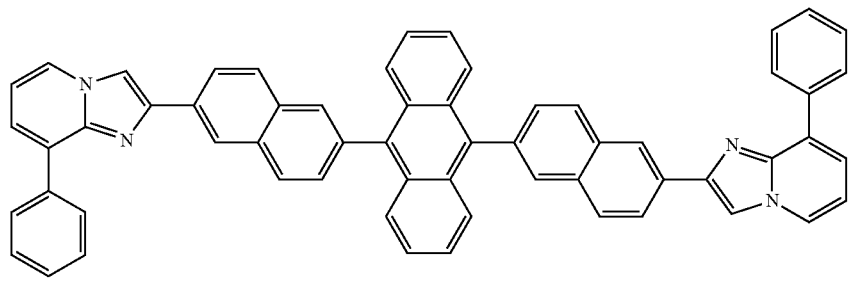
ETL-B12
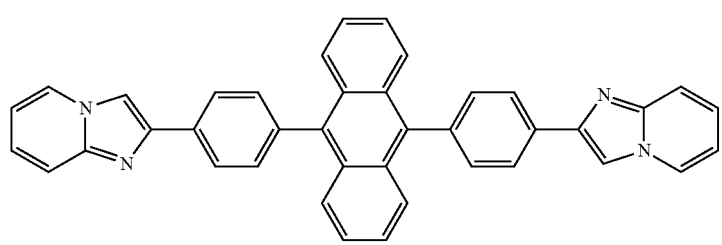
ETL-C1
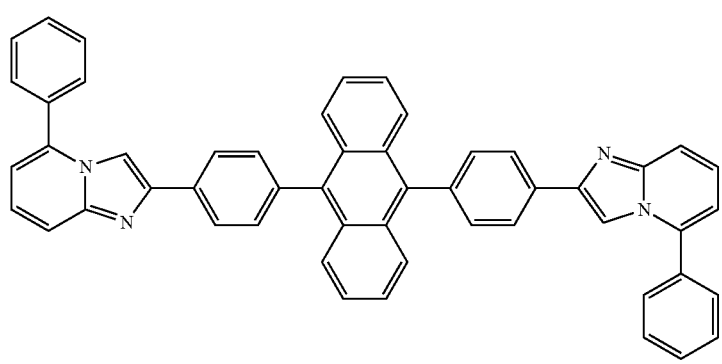
ETL-C2
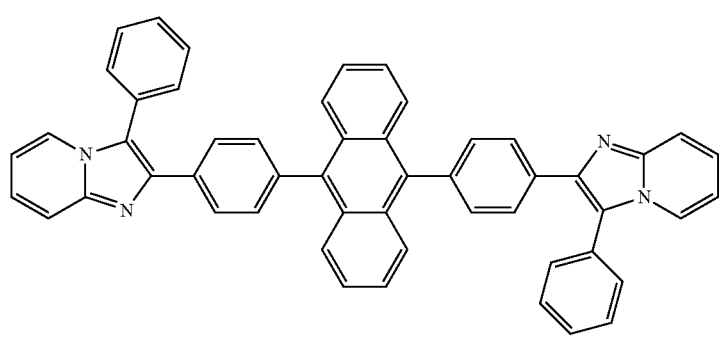
ETL-C3
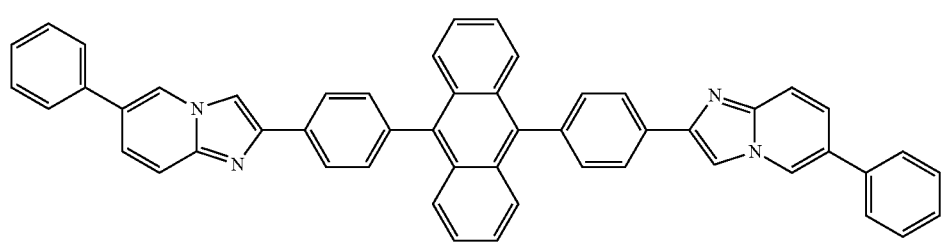
ETL-C4

-continued
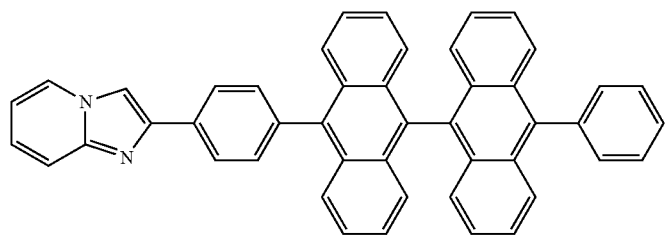
ETL-C5
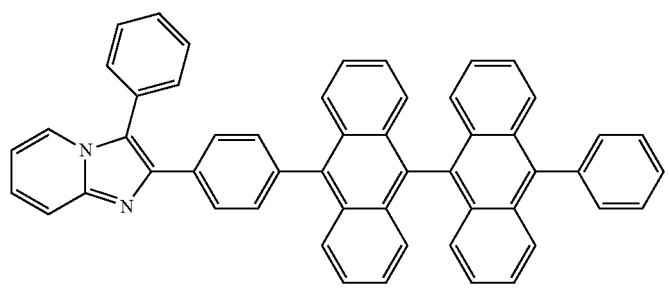
ETL-C6
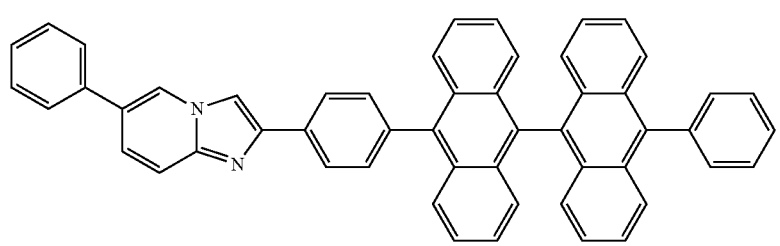
ETL-C7
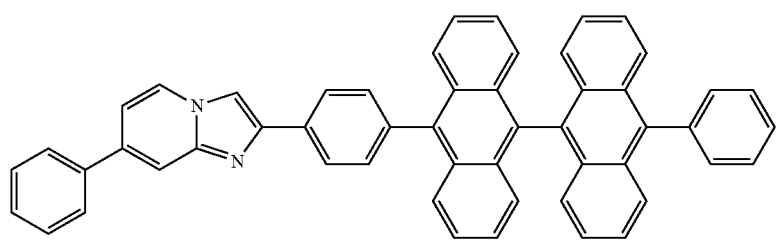
ETL-C8
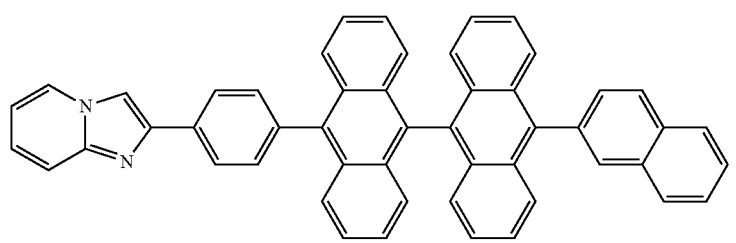
ETL-C9
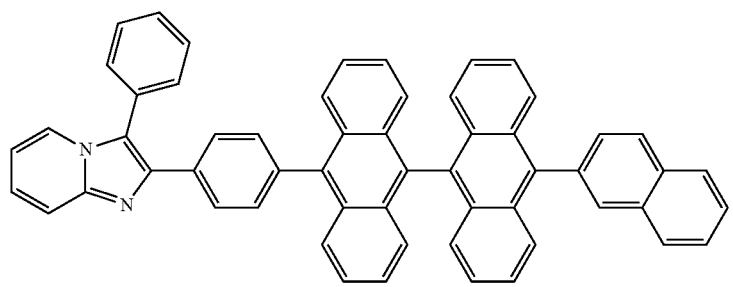
ETL-C10

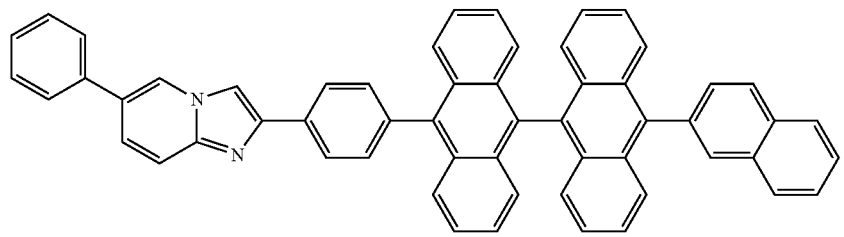
ETL-C11
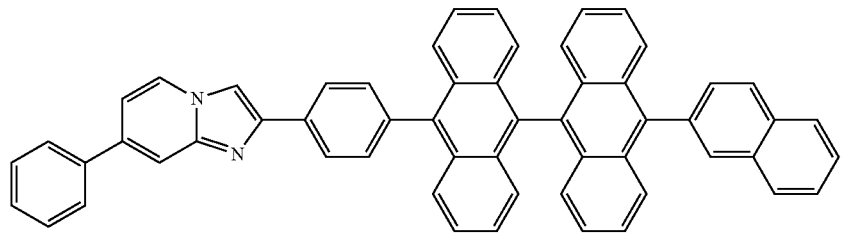
ETL-C12
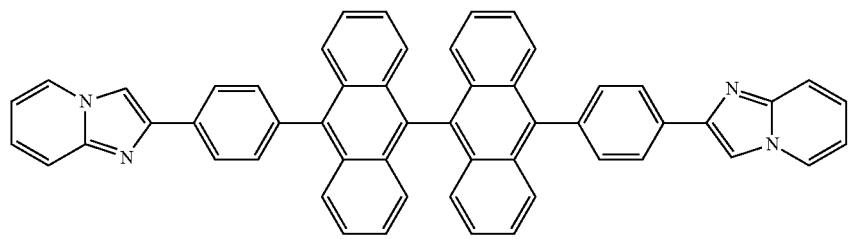
ETL-C13
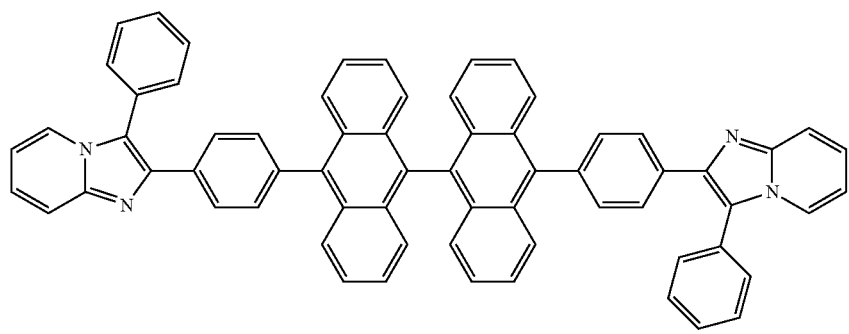
ETL-C14
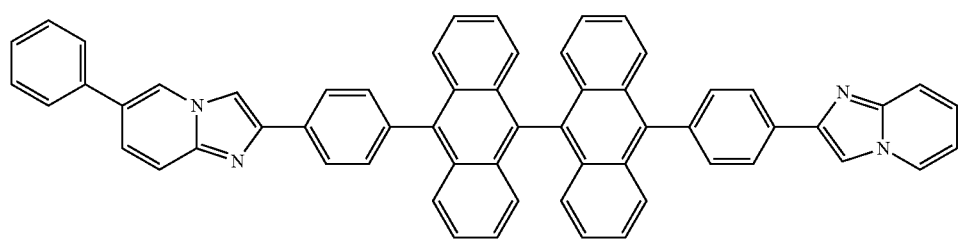
ETL-C15
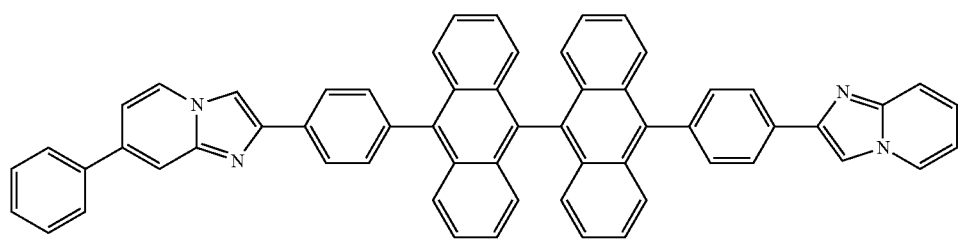
ETL-C16

-continued

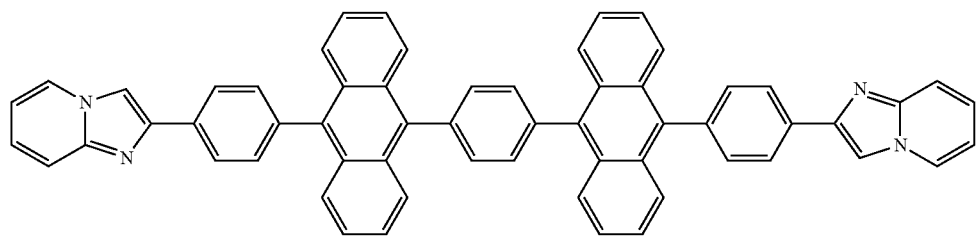
ETL-C17

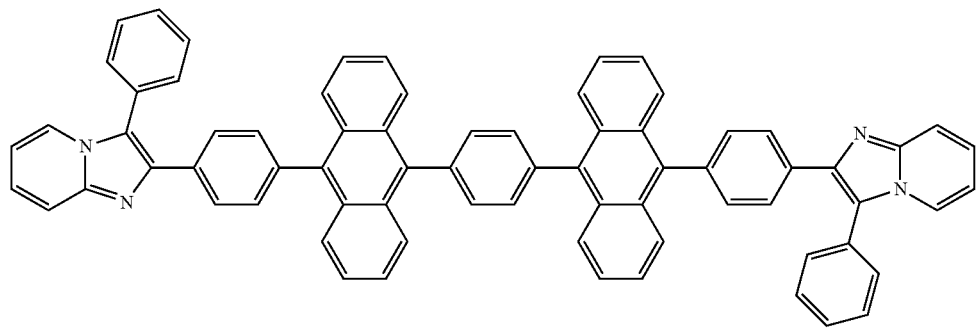
ETL-C18

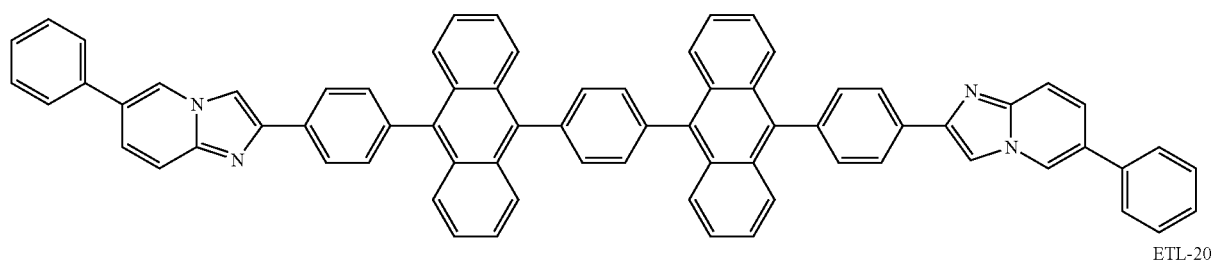
ETL-19

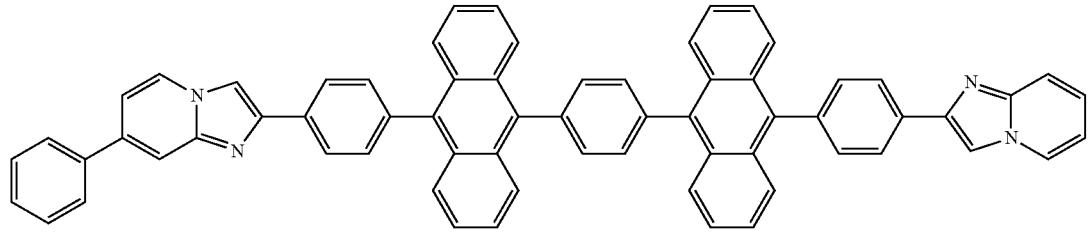
ETL-20

Such azaindolizines have excellent electron transport and electron injection properties and thus are effective in improving the light emission efficiency of the light-emitting element 1.

A possible explanation for the excellent electron transport and electron injection properties of such azaindolizines is as follows.

Azaindolizines of these types, which have an azaindolizine skeleton and an anthracene skeleton in the molecule, have an electron cloud spreading throughout the molecule because the entire molecule is a π-conjugated system.

The azaindolizine skeleton moiety of such an azaindolizine accepts electrons and transmits them to the anthracene skeleton moiety. On the other hand, the anthracene skeleton moiety of the azaindolizine receives electrons from the azaindolizine skeleton moiety and transfers them to the layer located next to the anode 3 side of the electron transport layer 7, namely the light-emitting layer 6.

A more detailed description is as follows. The azaindolizine skeleton moiety of the azaindolizine has two nitrogen atoms. One of these nitrogen atoms (the one located closer to the anthracene skeleton moiety) has $sp^2$ hybridized orbitals, and the other (the nitrogen atom located more distant from the anthracene skeleton moiety) has $sp^3$ hybridized orbitals. The nitrogen atom having $sp^2$ hybridized orbitals is a constituent of the molecular conjugated system of the azaindolizine and also serves as an electron acceptor site because it has a greater electronegativity and attracts electrons more strongly than carbon atoms. The other nitrogen atom, which has $sp^3$ hybridized orbitals, is not included in the ordinary conjugated system. However, this nitrogen atom has a lone electron pair and thus sends these electrons out toward the molecular conjugated system of the azaindolizine.

The anthracene skeleton moiety of the azaindolizine is electrically neutral and can easily receive electrons from the azaindolizine skeleton moiety. This anthracene skeleton moiety, which has an extensive orbital overlap with the materials used in the light-emitting layer 6, in particular, the host material (an acene-based material), can also easily transfer electrons to the host material in the light-emitting layer 6.

As mentioned above, this azaindolizine has excellent electron transport and electron injection properties. These excellent properties result in a lowered driving voltage of the light-emitting element 1.

Furthermore, the azaindolizine skeleton moiety remains stable even when the nitrogen atom having $sp^2$ hybridized orbitals is reduced or when the nitrogen atom having $sp^3$ hybridized orbitals is oxidized. This moiety thus makes the azaindolizine inert to electrons and holes, thereby extending the life of the light-emitting element 1.

When two or more of electron transport materials such as those listed above are used in combination, the electron transport layer 7 may be made of a composite material containing two or more electron transport materials or be a laminate having some layers made of different electron transport materials.

When the electron transport layer 7 is a laminate of two or more layers, it is preferred that the electron transport layer 7 has a first electron transport layer that contains an azaindolizine, described above, as a first electron transport material, and a second electron transport layer that is interposed between the first electron transport layer and the light-emitting layer 6, bordering both of these layers, and contains a second electron transport material different from the first one. This also makes the light-emitting element 1 able to operate for a longer period of time.

Examples of materials that can be used as the second electron transport material in this arrangement include Alq, tetracene-based materials, and anthracene-based materials. The average thickness of the second electron transport layer is not limited. It is preferably on the order of 5 nm to 20 nm, for example. This allows the second electron transport layer to form a hybrid layer with a portion of the light-emitting layer 6 or the first electron transport layer which ensures good transport of electrons from the electron transport layer 7 to the light-emitting layer 6, in addition to extending the life of the light-emitting element 1.

The average thickness of the electron transport layer 7 is not limited. It is preferably on the order of 1.0 nm to 200 nm, more preferably on the order of 10 nm to 100 nm.

Electron Injection Layer

The electron injection layer 8 improves the efficiency of the injection of electrons from the cathode 9.

Examples of materials that can be used to make the electron injection layer 8 (electron injection materials) include a range of insulating or semiconductor inorganic materials.

Examples of appropriate inorganic insulating materials include alkali metal chalcogenides (oxides, sulfides, selenides, and tellurides), alkaline-earth metal chalcogenides, alkali metal halides, and alkaline-earth metal halides. One or a combination of two or more of such materials can be used. The electron injection layer 8 has its electron injection properties enhanced when mainly composed of one or more of such materials. In particular, alkali metal compounds (e.g., alkali metal chalcogenides and alkali metal halides) have a very low work function and thus allow the light-emitting element 1 to emit very bright light when used to make the electron transport layer 8.

Examples of appropriate alkali metal chalcogenides include $Li_2O$, LiO, $Na_2S$, $Na_2Se$, and NaO.

Examples of appropriate alkaline-earth metal chalcogenides include CaO, BaO, SrO, BeO, BaS, MgO, and CaSe.

Examples of appropriate alkali metal halides include CsF, LiF, NaF, KF, LiCl, KCl, and NaCl.

Examples of appropriate alkaline-earth metal halides include $CaF_2$, $BaF_2$, $SrF_2$, $MgF_2$, and $BeF_2$.

As for inorganic semiconductor materials, examples of appropriate ones include oxides, nitrides, oxynitrides, and other similar compounds containing at least one of the following elements: Li, Na, Ba, Ca, Sr, Yb, Al, Ga, In, Cd, Mg, Si, Ta, Sb, and Zn. One or a combination of two or more of such materials can be used.

When the cathode 9 is made of Al, Ag, or MgAg, Li-containing materials such as lithium oxides or lithium halides are preferred.

The average thickness of the electron injection layer 8 is not limited. It is preferably on the order of 0.1 nm to 1000 nm, more preferably on the order of 0.2 nm to 100 nm, even more preferably on the order of 0.2 nm to 50 nm.

The electron injection layer 8 may be omitted, depending on the composition, thickness, and other characteristics of the cathode 9 and the electron transport layer 7.

Sealing Member

The sealing member 10 covers the anode 3, the laminate 14, and the cathode 9 and hermetically seals them to shut out oxygen and water. The sealing member 10 has several effects such as making the light-emitting element 1 more reliable and more resistant to alteration and deterioration (improved durability).

Examples of materials that can be used to make the sealing member 10 include metals such as Al, Au, Cr, Nb, Ta, and Ti, alloys of such metals, silicon oxides, and a range of resin materials. When the sealing member 10 contains a conductive material, it is preferred that an insulating film is interposed between the sealing member 10 and the anode 3, the laminate 14, and the cathode 9 as needed for the prevention of short circuits.

The sealing member 10 may be a flat plate facing the substrate 2, provided that the space between them is sealed with a sealing material such as thermosetting resin.

The light-emitting element 1 configured in this way can emit near-infrared light and offers improved efficiency and an extended service life owing to the thiadiazole used as a light-emitting material in the light-emitting layer 6.

The following is a typical procedure for producing such a light-emitting element 1.

I. A Substrate 2 is Prepared, and an Anode 3 is Formed on the Substrate 2.

The anode 3 can be formed by various processes including gas-phase processes such as chemical vapor deposition (CVD; e.g., plasma CVD and thermal CVD) and vacuum deposition, liquid-phase processes such as electrolytic plating, thermal spraying processes, sol-gel processes, metal-organic deposition (MOD) processes, and metal foil cladding.

II. A Hole Injection Layer 4 is Formed on the Anode 3.

Examples of preferred processes for the formation of the hole injection layer 4 include gas-phase processes such as CVD, vacuum deposition, and sputtering.

It is also possible to form the hole injection layer 4 by dissolving the hole injection material(s) in a solvent or dispersing in a dispersion medium, applying the obtained hole injection layer base to the anode 3, and drying the applied material (removing the solvent or dispersion medium).

Examples of appropriate methods for applying the hole injection layer base include a range of application methods such as spin coating, roll coating, and ink jet printing. By such application methods, the hole injection layer 4 can be formed relatively easily.

Examples of solvents and dispersing media that can be used to prepare the hole injection layer base include a range of inorganic and organic solvents and mixtures of such solvents.

The drying process can be performed by various methods, including leaving the applied material at atmospheric pressure or a reduced pressure, heating, and spraying with an inert gas.

The top surface of the anode 3 may be treated with oxygen plasma beforehand. This has several effects including making the top surface of the anode 3 lyophilic, removing (washing away) adhesive organic matter from the top surface of the anode 3, and adjusting the work function of the superficial portion of the anode 3.

An example of preferred conditions of oxygen plasma treatment is as follows: plasma power, approximately 100 W to 800 W; oxygen flow rate, approximately 50 mL/min to 100 mL/min; transport speed of the material under treatment (the anode 3), approximately 0.5 mm/sec to 10 mm/sec; temperature of the substrate 2, approximately 70° C. to 90° C.

III. A Hole Transport Layer 5 is Formed on the Hole Injection Layer 4.

Examples of preferred processes for the formation of the hole transport layer 5 include gas-phase processes such as CVD, vacuum deposition, and sputtering.

It is also possible to form the hole transport layer 5 by dissolving the hole transport material(s) in a solvent or dispersing in a dispersion medium, applying the obtained hole transport layer base to the hole injection layer 4, and drying the applied material (removing the solvent or dispersion medium).

IV. A Light-Emitting Layer 6 is Formed on the Hole Transport Layer 5.

Examples of appropriate processes for the formation of the light-emitting layer 6 include gas-phase processes such as vacuum deposition.

V. An Electron Transport Layer 7 is Formed on the Light-Emitting Layer 6.

Examples of preferred processes for the formation of the electron transport layer 7 include gas-phase processes such as vacuum deposition.

It is also possible to form the electron transport layer 7 by dissolving the electron transport material(s) in a solvent or dispersing in a dispersion medium, applying the obtained electron transport layer base to the light-emitting layer 6, and drying the applied material (removing the solvent or dispersion medium).

VI. An Electron Injection Layer 8 is Formed on the Electron Transport Layer 7.

When the electron injection layer 8 is made of inorganic material(s), the electron injection layer 8 can be formed by gas-phase processes such as CVD, vacuum deposition, and sputtering or applying and firing an ink containing inorganic fine particles, for example.

VII. A Cathode 9 is Formed on the Electron Injection Layer 8.

The cathode 9 can be formed by gas-phase processes such as vacuum deposition and sputtering, metal foil cladding, or applying and firing an ink containing metal fine particles, for example.

Through such operations, the light-emitting element 1 is obtained.

Finally, a sealing member 10 is placed to cover the light-emitting element 1 and bonded to the substrate 2.

Light-Emitting Apparatus

The following describes an embodiment of the light-emitting apparatus according to an aspect of the invention.

Figure 2:
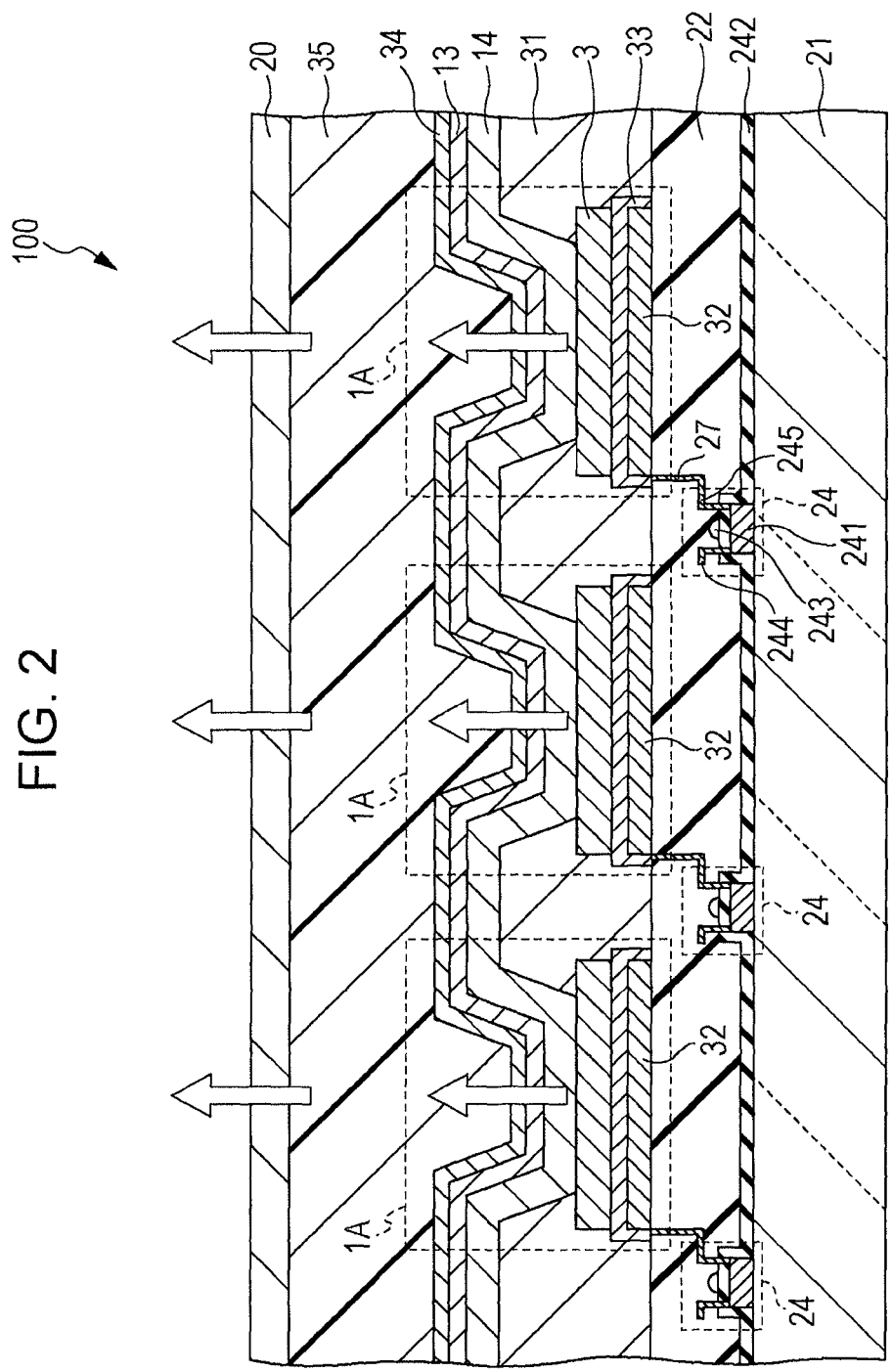
FIG. 2 is a vertical cross-sectional diagram illustrating an embodiment of a display apparatus as a light-emitting apparatus according to an aspect of the invention.

FIG. 2 is a vertical cross-sectional diagram illustrating an embodiment of a display apparatus as a light-emitting apparatus according to an aspect of the invention.

The display apparatus 100 illustrated in FIG. 2 has a substrate 21, light-emitting elements 1A, and driving transistors 24 for driving the individual light-emitting elements 1A. The display apparatus 100 is a top-emission display panel.

The driving transistors 24 are on the substrate 21, and these driving transistors 24 are covered with a planarizing layer 22 made of an insulating material.

Each of the driving transistors 24 has a semiconductor layer 241 made of silicon, a gate insulating layer 242 formed on the semiconductor layer 241, and a gate electrode 243, a source electrode 244, and a drain electrode 245 formed on the gate insulating layer 242.

On the planarizing layer 22 the light-emitting elements 1A are formed corresponding to the individual driving transistors 24.

Each of the light-emitting elements 1A contains a reflection film 32, a corrosion protection film 33, an anode 3, a laminate (an organic EL light-emitting portion) 14, a cathode 13, and a cathode coating 34 stacked in this order on the planarizing layer 22.

In this embodiment, the anode 3 of each light-emitting element 1A serves as a pixel electrode and is electrically coupled to the drain electrode 245 of the corresponding driving transistor 24 via a conductive portion (lead wire) 27. The cathode 13 is a common electrode shared by the light-emitting elements 1A.

The light-emitting elements 1A in FIG. 2 emit near-infrared light.

The individual light-emitting elements 1A are separated by partitions 31. An epoxy layer 35 made of epoxy resin covers these light-emitting elements 1A.

On the epoxy layer 35 there is a sealing substrate 20 covering all other components.

Such a display apparatus 100 can be used as, for example, a near-infrared display for military and other purposes.

Such a display apparatus 100 can emit near-infrared light, and has excellent reliability because of the high efficiency and long life of the light-emitting elements 1A.

Authentication Apparatus

The following describes an embodiment of the authentication apparatus according to an aspect of the invention.

Figure 3:
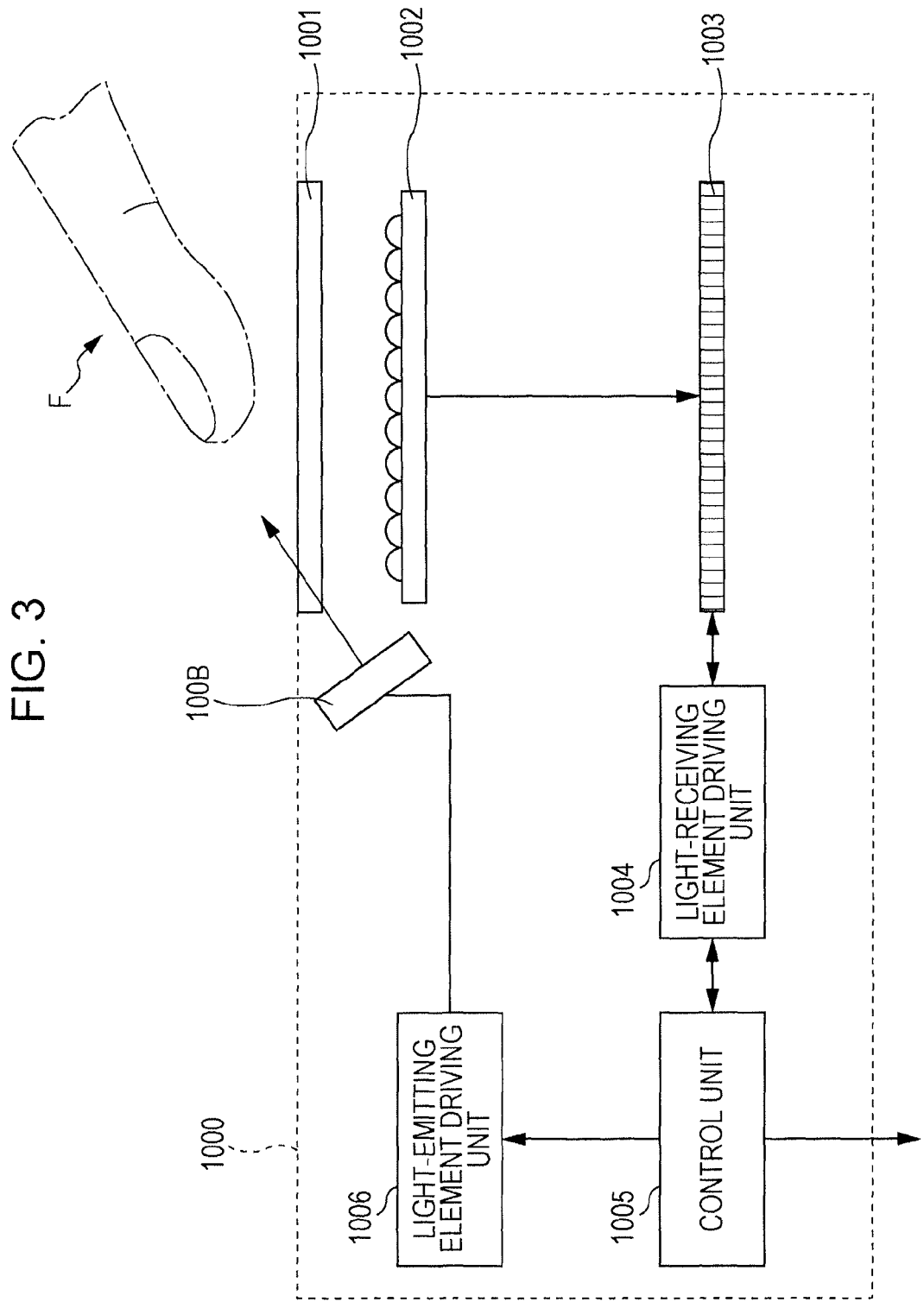
FIG. 3 illustrates an embodiment of the authentication apparatus according to an aspect of the invention.

FIG. 3 illustrates an embodiment of the authentication apparatus according to an aspect of the invention.

The authentication apparatus 1000 illustrated in FIG. 3 is a biometric authentication apparatus which verifies individuals on the basis of their biological information extracted from their body part F (in this embodiment, a fingertip).

The authentication apparatus 1000 has a light source 100B, a coverslip 1001, a microlens array 1002, a light-receiving element panel 1003, a light-emitting element driving unit 1006, a light-receiving element driving unit 1004, and a control unit 1005.

The light source 100B has light-emitting elements 1, described above, and emits near-infrared light toward the subject, i.e., the body part F. In a typical configuration, the light-emitting elements 1 of the light source 100B are arranged along the edge of the coverslip 1001.

The coverslip 1001 is a component that the body part F touches or approaches.

The microlens array 1002 is located on the opposite side of the coverslip 1001 to the side where the body part F touches or approaches. The microlens array 1002 is composed of microlenses arranged in a matrix.

The light-receiving element panel 1003 is located on the opposite side of the microlens array 1002 to the side where the coverslip 1001 is. The light-receiving element panel 1003 is composed of light-receiving elements arranged in a matrix corresponding to the microlenses on the microlens array 1002. Examples of appropriate light-receiving elements for use in the light-receiving element panel 1003 include CCD (charge-coupled device) and CMOS image sensors.

The light-emitting element driving unit 1006 is a driving circuit for the light source 100B.

The light-receiving element driving unit 1004 is a driving circuit for the light-receiving element panel 1003.

The control unit 1005, which is an MPU or the like, controls the operation of the light-emitting element driving unit 1006 and the light-receiving element driving unit 1004.

The control unit 1005 also compares light detection signals coming from the light-receiving element panel 1003 with the biometric information stored in advance and verifies the identity of the body part F.

A typical process for this is as follows. First, the control unit 1005 generates an image pattern (e.g., a vein pattern) on the basis of light detection signals coming from the light-receiving element panel 1003. Then the control unit 1005 compares the image pattern with another, which carries biometric information and is stored in advance, and verifies the identity of the body part F (e.g., authenticates the individual with his/her vein) on the basis of the comparison results.

Such an authentication apparatus 1000 allows biometric authentication using near-infrared light, and has excellent reliability because of the high efficiency and long life of the light-emitting elements 1.

Furthermore, such an authentication apparatus 1000 can be incorporated into various electronic devices.

Electronic Device

Figure 4:
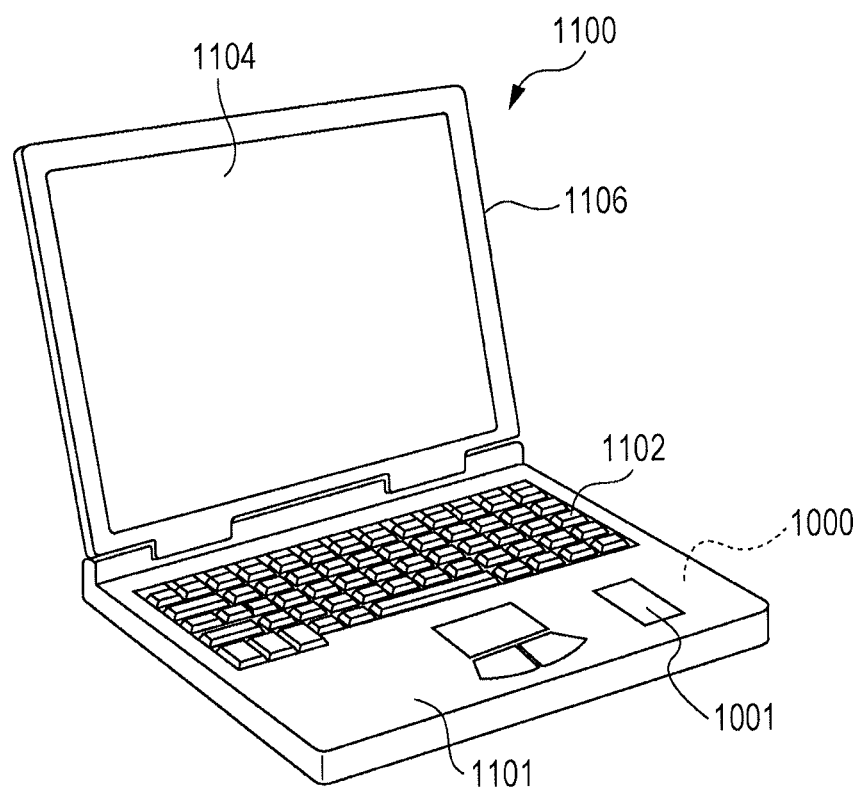
FIG. 4 is a perspective diagram illustrating the configuration of a mobile (or notebook) PC as an electronic device according to an aspect of the invention.

FIG. 4 is a perspective diagram illustrating the configuration of a mobile (or notebook) PC as an electronic device according to an aspect of the invention.

In this drawing, a PC 1100 has a body 1101 provided with a keyboard 1102 and also has a display unit 1106 provided with a display portion 1104. The display unit 1106 is attached to the body 1101 via a hinge structure and can swing open and shut.

The PC 1100 incorporates an authentication apparatus 1000, described above, in the body 1101.

Such a PC 1100 has excellent reliability because of the high efficiency and long life of the light-emitting elements 1 used therein.

Applications of the electronic device according to an aspect of the invention are not limited to PCs of the type illustrated in FIG. 4 (mobile PCs) and include the following: mobile phones, digital still cameras, televisions, video cameras, video recorders with a viewfinder or a direct-view monitor, laptop PCs, automotive navigation systems, pagers, electronic organizers (with or without a communication function), electronic dictionaries, calculators, electronic game consoles, word processors, workstations, videophones, CCTV monitors, electronic binoculars, POS terminals, touch-screen devices (e.g., ATMs and ticket machines), medical devices (e.g., electronic clinical thermometers, manometers, glucose meters, pulsometers, sphygmographs, ECG monitors, ultrasonic diagnostic systems, and endoscopic monitors), fishfinders, a range of measuring instruments, gauges (e.g., those for automobiles, airplanes, and ships), flight simulators, many other kinds of monitors, and projection display apparatuses such as projectors.

The illustrated embodiments of the thiadiazole, the compound for light-emitting elements, the light-emitting element, the light-emitting apparatus, the authentication apparatus, and the electronic device according to aspects of the invention should not be construed as limiting the scope of the invention.

For example, the light-emitting element and the light-emitting apparatus according to aspects of the invention can be used as illumination light sources.

It is also possible that the light-emitting element has a visible-light-emitting layer between the anode and the cathode in addition to the light-emitting layer containing the thiadiazole according to an aspect of the invention.

Furthermore, the purpose of use of the thiadiazole according to an aspect of the invention is not limited to the light-emitting material described in the foregoing embodiments; the thiadiazole according to an aspect of the invention can also be used in other applications. For example, the thiadiazole according to an aspect of the invention may be used in a layer between the anode and the cathode to trap carriers and convert them into heat (infrared radiation). This selectively inhibits or prevents the electrons (carriers) left unused in the light-emitting layer from moving toward the hole transport layer side and altering or damaging the materials of the hole transport layer and the hole injection layer. As a result, the life of the light-emitting element is extended.

EXAMPLES

The following describes some specific examples of the invention.

1. Preparation of a Thiadiazole

1-1. Synthesis Example A1, Synthesis of Compound D1-2

Synthesis Step A1-1

First, 1500 mL of fuming nitric acid was put into a 5-L flask and cooled. To this flask, 1500 mL of sulfuric acid was added in several portions so that the temperature was maintained at 10° C. to 50° C. Then 150 g of compound (a), raw material dibromobenzothiadiazole, was added in small amounts over 1 hour. The temperature of the solution was maintained at 5° C. or less during this operation. After all of compound (a) was added, the reaction was allowed to

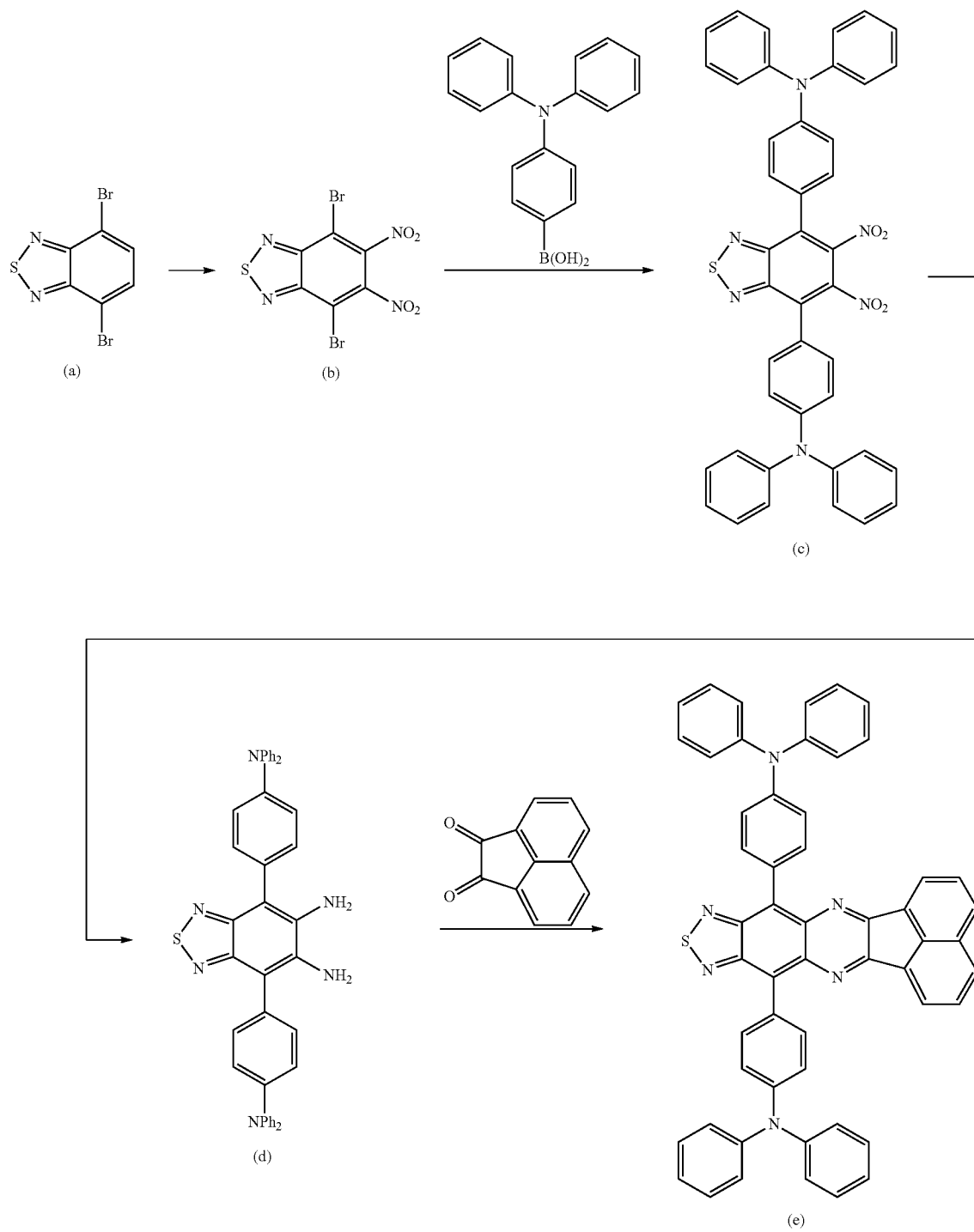

proceed at room temperature (25° C.) for 20 hours. After the completion of the reaction, the reaction solution was poured into 3 kg of ice and stirred overnight. The solution was filtered, and the residue was washed with methanol and heptane.

The residue was then dissolved in 200 mL of toluene by heating. The solution was allowed to cool to room temperature and filtered. The residue was washed with a small amount of toluene and dried under reduced pressure.

In this way, 60 g of compound (b) (4,7-dibromo-5,6-dinitro-benzo[1,2,5]thiadiazole) was obtained with an HPLC purity of 95%.

Synthesis Step A1-2

In an Ar atmosphere, 30 g of the obtained dibromide (b), 23 g of triphenylamine boronic acid, 2500 mL of toluene, and a 2 M aqueous solution of cesium carbonate (152 g in 234 mL of distilled water) were put into a 5-L flask, and the reaction was allowed to proceed at 90° C. overnight. After the completion of the reaction, the solution was filtered and separated, and the isolated layer was concentrated. The resulting crude product, which weighed 52 g, was separated using a silica gel column (5 kg of $SiO_2$) and a red-purple solid was obtained.

In this way, 6 g of compound (c) (5,6-dinitro-4,7-diphenyl-benzo[1,2,5]thiadiazole) was obtained with an HPLC purity of 96%.

The triphenylamine boronic acid was synthesized by the following procedure. In an Ar atmosphere, 246 g of 4-bromotriphenylamine (a commercially available product) and 1500 mL of anhydrous tetrahydrofuran were put into a 5-L flask, and 570 mL of a 1.6 M n-BuLi solution in hexane was added dropwise at −60° C. over 3 hours. Thirty minutes later, 429 g of triisopropyl borate was added dropwise over 1 hour. Then the reaction was allowed to proceed overnight with no temperature control. After the completion of the reaction, 2 L of water was added dropwise, and the obtained solution was subjected to extraction and separation with 2 L of toluene. The organic layer was concentrated, the residue was recrystallized, and the crystals were collected by filtration and dried. In this way, the intended boronic acid was obtained as a white solid weighing 160 g. The HPLC purity of the boronic acid was 99%.

Synthesis Step A1-3

In an Ar atmosphere, the obtained dinitride (c), 6 g, was put into a 1-L flask with 7 g of reduced iron and 600 mL of acetic acid, the reaction was allowed to proceed at 80° C. for 4 hours, and the solution was allowed to cool to room temperature. After the completion of the reaction, the reaction solution was poured into 1.5 L of ion-exchanged water, and 1.5 L of ethyl acetate was added. Since a precipitate immediately appeared, 1 L of tetrahydrofuran and 300 g of sodium chloride were added, and the obtained solution was subjected to extraction and separation. The aqueous layer was subjected to another round of extraction with 1 L of tetrahydrofuran. The dry residue after evaporation was washed with small amounts of water and methanol and an orange solid was obtained.

In this way, 7 g of compound (d) (4,7-diphenyl-benzo[1,2,5]thiadiazole-5,6-diamine) was obtained with an HPLC purity of 80%.

Synthesis Step A1-4

In an Ar atmosphere, 4.5 g of the obtained diamine (d), 1.9 g of acenaphthoquinone, and 300 mL of acetic acid as solvent were put into a 1-L flask, and the reaction was allowed to proceed at 80° C. for 2 hours. After the completion of the reaction, the solution was allowed to cool to room temperature and poured into 1 L of ion-exchanged water. The resulting crystals were collected by filtration and washed with water, yielding a dark green solid weighing 7 g. This dark green solid was purified using a silica gel column (1 kg of $SiO_2$).

In this way, 4.5 g of compound (e) (acenaphtho-2-thia-1,3,5,8-tetraaza-cyclopenta[b]naphthalene, compound D1-2) was obtained with an HPLC purity of 99%. The obtained compound (e) was analyzed by mass spectrometry and found to have an $M^+$ of 799.

The obtained compound (e) was then purified by sublimation at a set temperature of 350° C. The HPLC purity of the sublimation-purified compound (e) was 99%.

1-2. Synthesis Example A2, Synthesis of Compound D1-4

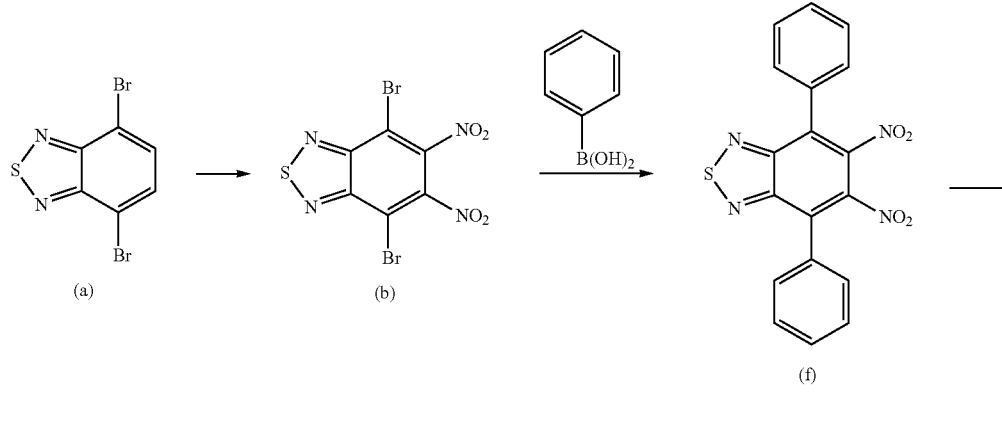

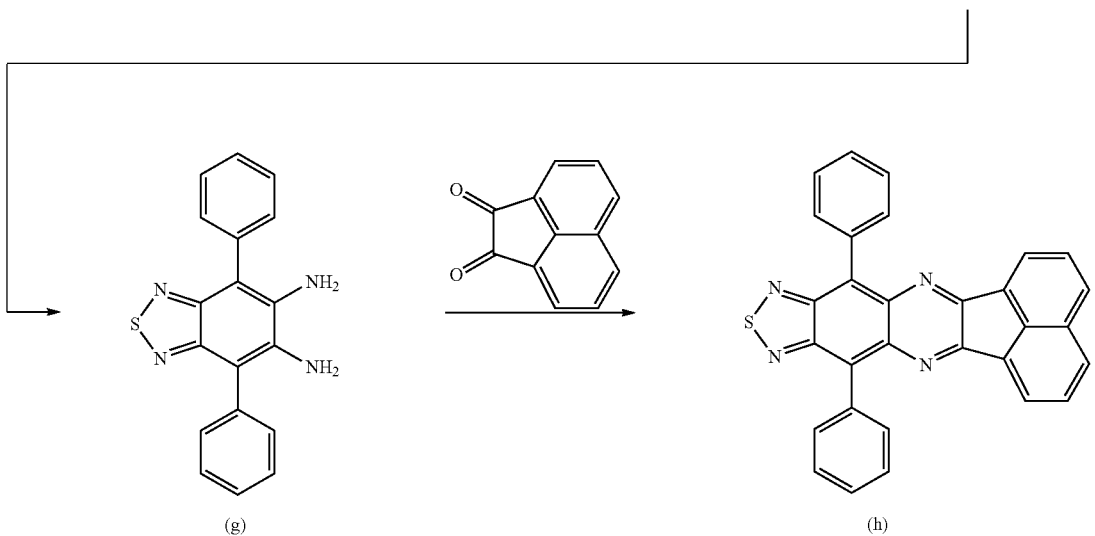

(g)    (h)

The same synthesis steps as in Synthesis Example A1 were repeated except the triphenylamine boronic acid used in Synthesis Step A1-2 in Synthesis Example A1 was replaced with phenylboronic acid. In this way, compound (h), i.e., compound D1-4, was obtained.

More specifically, the same procedure as Synthesis Step A1-2 in Synthesis Example A1 was repeated using phenylboronic acid (a commercially available product) instead of the triphenylamine boronic acid and compound (f) was obtained.

The same procedure as Synthesis Step A1-3 in Synthesis Example A1 was then repeated with the obtained compound (f) and compound (g) was obtained.

Then the same procedure as Synthesis Step A1-4 in Synthesis Example A1 was repeated with the obtained compound (g) and compound (h), i.e., compound D1-4, was obtained.

1-3. Synthesis Example A3, Synthesis of Compound D1-5

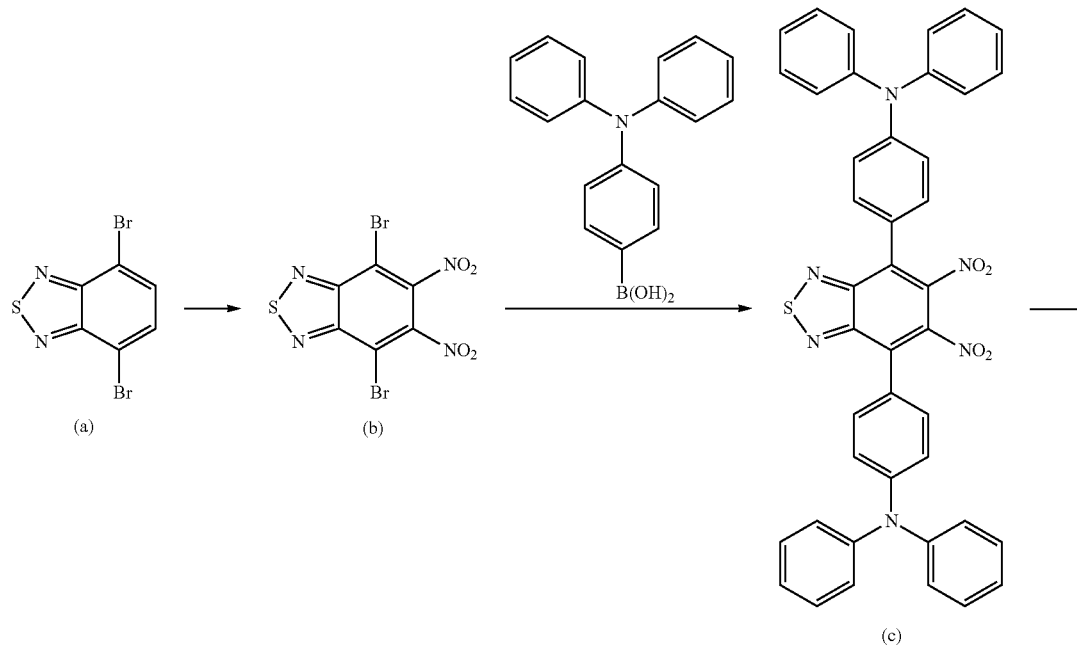

(a)    (b)    (c)

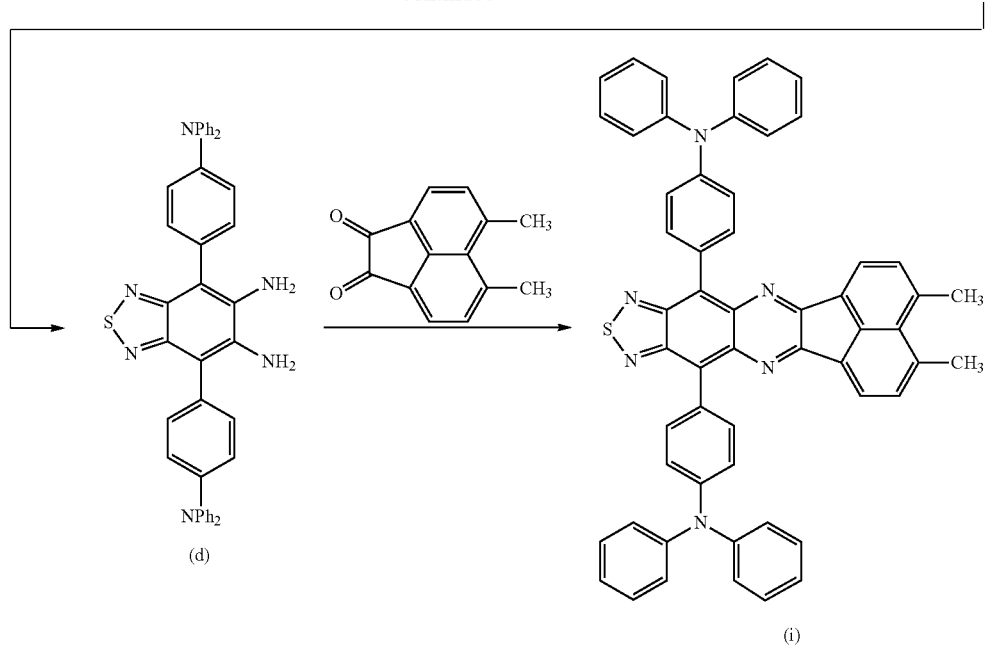
The same synthesis steps as in Synthesis Example A1 were repeated except acenaphthoquinone used in Synthesis Step A1-4 in Synthesis Example A1 was replaced with 5,6-dimethylacenaphthoquinone. In this way, compound (i), i.e., compound D1-5, was obtained.
1-4. Synthesis Example A4, Synthesis of Compound D1-8
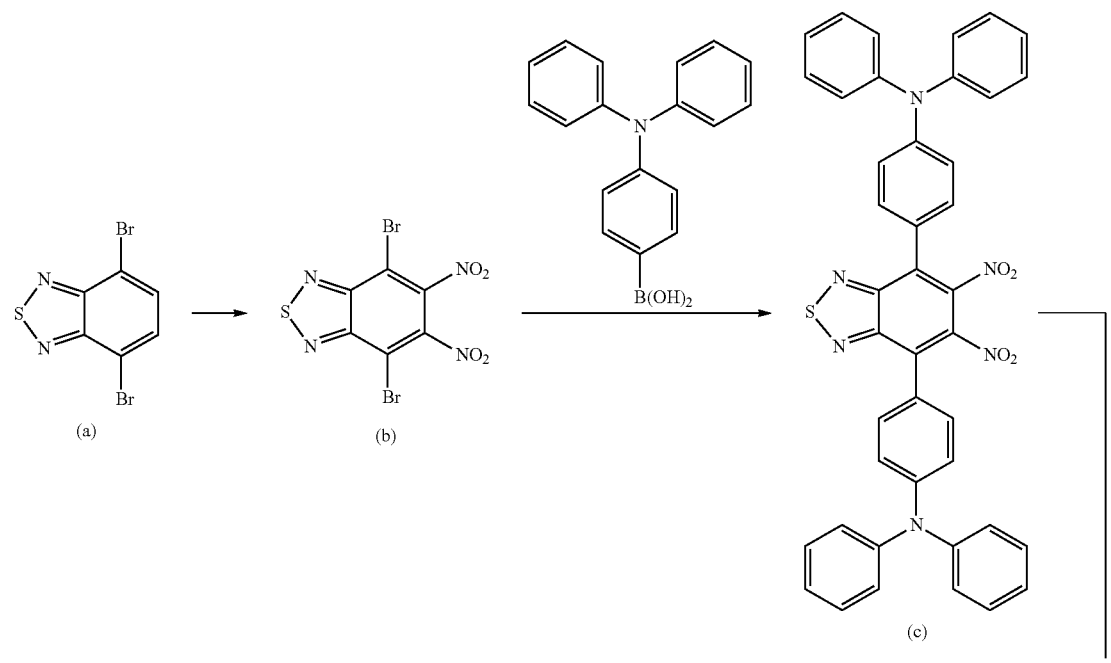

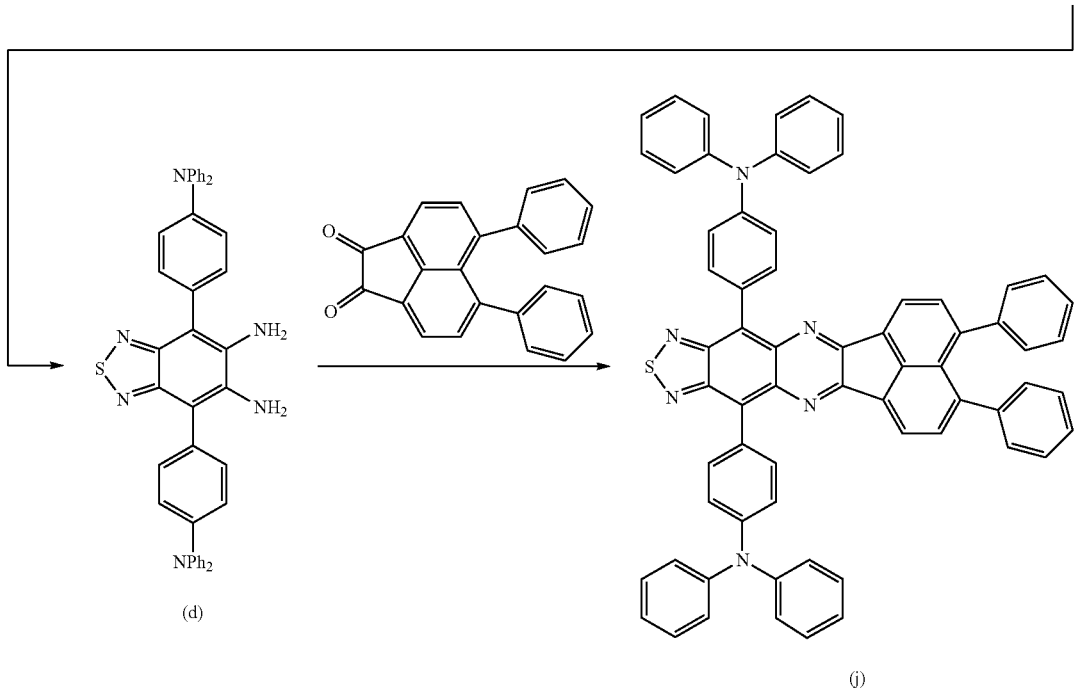
(d) → (j)
The same synthesis steps as in Synthesis Example A1 were repeated except acenaphthoquinone used in Synthesis Step A1-4 in Synthesis Example A1 was replaced with 5,6-diphenylacenaphthoquinone. In this way, compound (j), i.e., compound D1-8, was obtained.
1-5. Synthesis Example A5, Synthesis of Compound D2-1
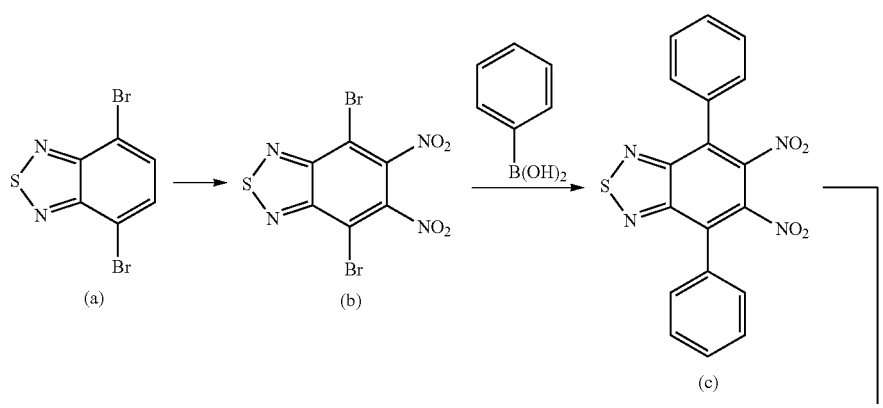
(a) → (b) → (c)

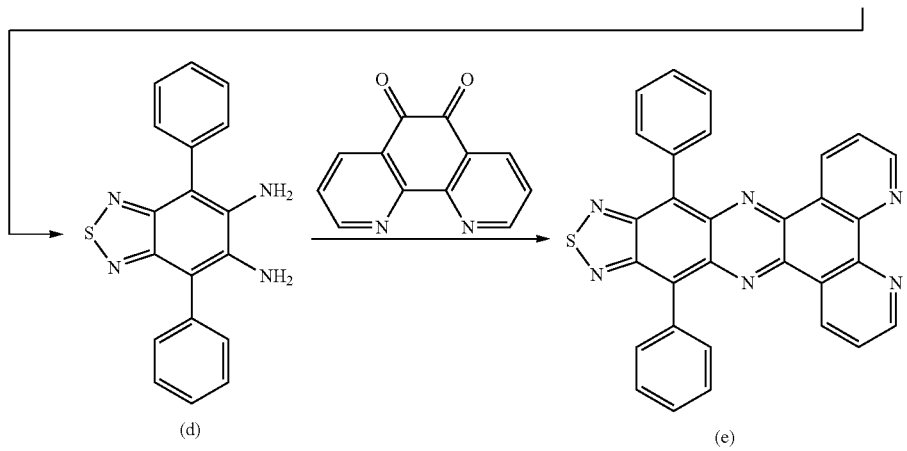

Synthesis Step A5-1

First, 1500 mL of fuming nitric acid was put into a 5-L flask and cooled. To this flask, 1500 mL of sulfuric acid was added in several portions so that the temperature was maintained at 10° C. to 50° C. Then 150 g of compound (a), raw material dibromobenzothiadiazole, was added in small amounts over 1 hour. The temperature of the solution was maintained at 5° C. or less during this operation. After all of compound (a) was added, the reaction was allowed to proceed at room temperature (25° C.) for 20 hours. After the completion of the reaction, the reaction solution was poured into 3 kg of ice and stirred overnight. The solution was filtered, and the residue was washed with methanol and heptane.

The residue was then dissolved in 200 mL of toluene by heating. The solution was allowed to cool to room temperature and filtered. The residue was washed with a small amount of toluene and dried under reduced pressure.

In this way, 60 g of compound (b) (4,7-dibromo-5,6-dinitro-benzo[1,2,5]thiadiazole) was obtained with an HPLC purity of 95%.

Synthesis Step A5-2

In an Ar atmosphere, 30 g of the obtained dibromide (b), 23 g of phenylboronic acid (a commercially available product), 2500 mL of toluene, and a 2 M aqueous solution of cesium carbonate (152 g in 234 mL of distilled water) were put into a 5-L flask, and the reaction was allowed to proceed at 90° C. overnight. After the completion of the reaction, the solution was filtered and separated, and the isolated layer was concentrated. The resulting crude product, which weighed 52 g, was separated using a silica gel column (5 kg of SiO$_2$) and a red-purple solid was obtained.

In this way, 6 g of compound (c) (5,6-dinitro-4,7-diphenyl-benzo[1,2,5]thiadiazole) was obtained with an HPLC purity of 96%.

Synthesis Step A5-3

In an Ar atmosphere, the obtained dinitride (c), 6 g, was put into a 1-L flask with 7 g of reduced iron and 600 mL of acetic acid, the reaction was allowed to proceed at 80° C. for 4 hours, and the solution was allowed to cool to room temperature. After the completion of the reaction, the reaction solution was poured into 1.5 L of ion-exchanged water, and 1.5 L of ethyl acetate was added. Since a precipitate immediately appeared, 1 L of tetrahydrofuran and 300 g of sodium chloride were added, and the obtained solution was subjected to extraction and separation. The aqueous layer was subjected to another round of extraction with 1 L of tetrahydrofuran. The dry residue after evaporation was washed with small amounts of water and methanol and an orange solid was obtained.

In this way, 7 g of compound (d) (4,7-diphenyl-benzo[1,2,5]thiadiazole-5,6-diamine) was obtained with an HPLC purity of 80%.

Synthesis Step A5-4

In an Ar atmosphere, 4.5 g of the obtained diamine (d), 2.97 g of 1,10-phenanthroline-5,6-dione, and 300 mL of acetic acid as solvent were put into a 1-L flask, and the reaction was allowed to proceed at 80° C. for 2 hours. After the completion of the reaction, the solution was allowed to cool to room temperature and poured into 1 L of ion-exchanged water. The resulting crystals were collected by filtration and washed with water, yielding a dark green solid weighing 7.1 g. This dark green solid was purified using a silica gel column (1 kg of SiO$_2$).

In this way, 4.4 g of compound (e) (compound D2-1) was obtained with an HPLC purity of 99%. The obtained compound (e) was analyzed by mass spectrometry and found to have an M$^+$ of 492.

The obtained compound (e) was then purified by sublimation at a set temperature of 340° C. The HPLC purity of the sublimation-purified compound (e) was 99%.

1-6. Synthesis Example A6, Synthesis of Compound D2-2

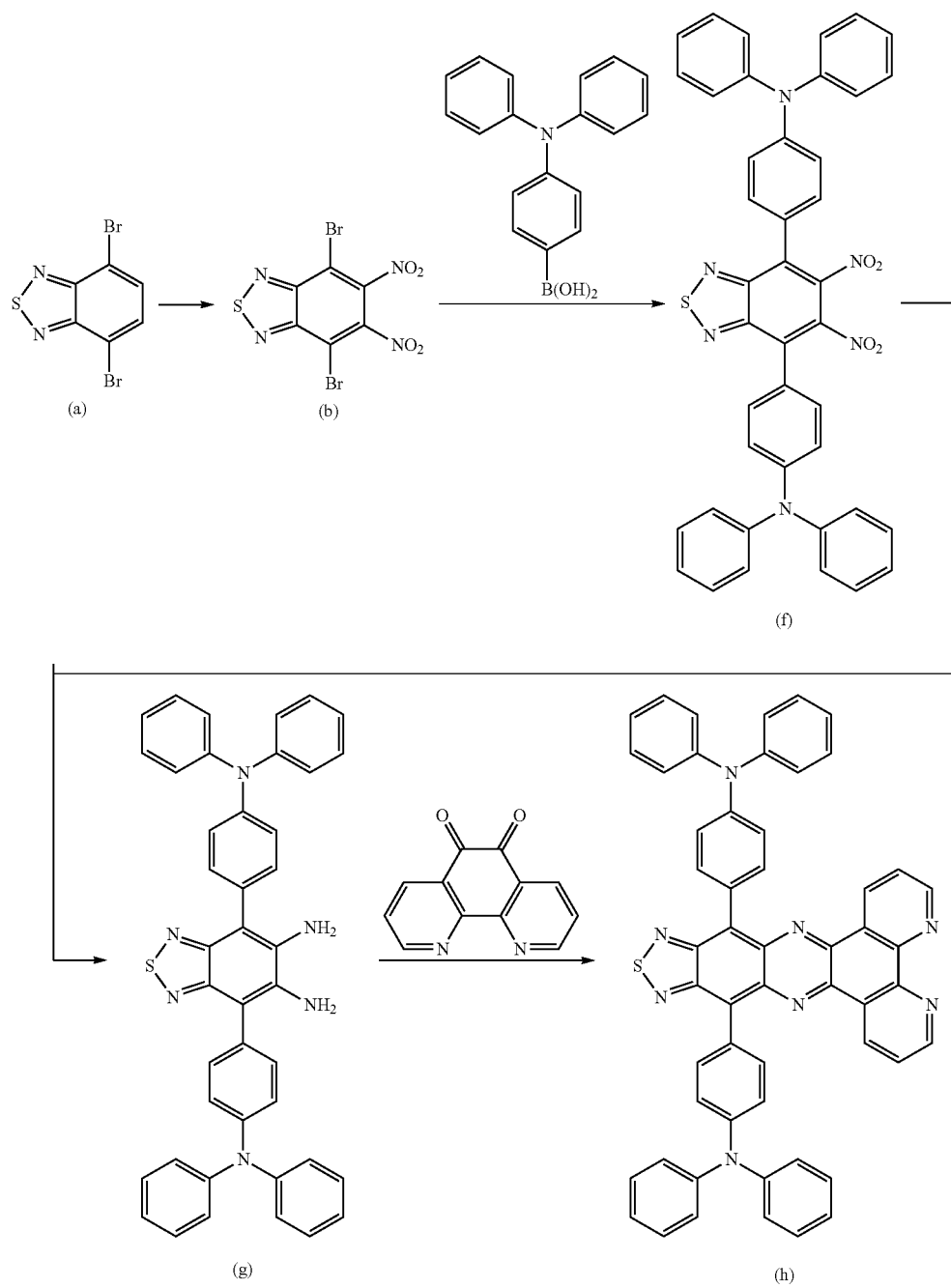

The same synthesis steps as in Synthesis Example A5 were repeated except phenylboronic acid used in Synthesis Step A5-2 in Synthesis Example A5 was replaced with a triphenylamine boronic acid. In this way, compound (h), i.e., compound D2-2, was obtained.

The triphenylamine boronic acid was synthesized by the following procedure. In an Ar atmosphere, 246 g of 4-bromotriphenylamine (a commercially available product) and 1500 mL of anhydrous tetrahydrofuran were put into a 5-L flask, and 570 mL of a 1.6 M n-BuLi solution in hexane was added dropwise at −60° C. over 3 hours. Thirty minutes later, 429 g of triisopropyl borate was added dropwise over 1 hour. Then the reaction was allowed to proceed overnight with no temperature control. After the completion of the reaction, 2 L of water was added dropwise, and the obtained solution was subjected to extraction and separation with 2 L of toluene. The organic layer was concentrated, the residue was recrystallized, and the crystals were collected by filtration and dried. In this way, the intended boronic acid was obtained as a white solid weighing 160 g.

The HPLC purity of the obtained boronic acid was 99%.

Then the same procedure as Synthesis Step A5-2 in Synthesis Example A5 was repeated with the obtained boronic acid and compound (f) was obtained.

The same procedure as Synthesis Step A5-3 in Synthesis Example A5 was then repeated with the obtained compound (f) and compound (g) was obtained.

Then the same procedure as Synthesis Step A5-4 in Synthesis Example A5 was repeated with the obtained compound (g) and compound (h), i.e., compound D2-2, was obtained.

In this way, compound (h) (compound D2-2) was obtained as a deep navy blue solid weighing 3.2 g with an HPLC purity of 99%. The obtained compound (h) was analyzed by mass spectrometry and found to have an M$^+$ of 826.

The obtained compound (h) was then purified by sublimation at a set temperature of 360° C. The HPLC purity of the sublimation-purified compound (h) was 99%.

1-7. Synthesis Example A7, Synthesis of Compound D2-3

Separately, in an Ar atmosphere, 30 g of the dibromide (b) and 33 g of diphenylamine (a commercially available product) were put into a 5-L flask and dissolved in 2500 mL of toluene, and the solution was warmed to 100° C. The Pd catalyst and 20 g of t-BuOK were added, and the solution was heated to reflux for 3 hours.

After the reaction was complete and the solution cooled to room temperature, 100 mL of water was added, and the solution was stirred for approximately 1 hour. The solution was then transferred to a separatory funnel and washed with water by separation. The organic layer was collected and dried. The obtained solid was separated using a silica gel column (5 kg of SiO$_2$) and a purple solid was obtained.

In this way, 10 g of compound (i) (5,6-dinitro-N,N,N',N'-tetraphenyl-benzo[1,2,5]thiadiazole) was obtained with an HPLC purity of 96%.

Then the same procedure as Synthesis Step A5-3 in Synthesis Example A5 was repeated with the obtained compound (i) and compound (j) was obtained.

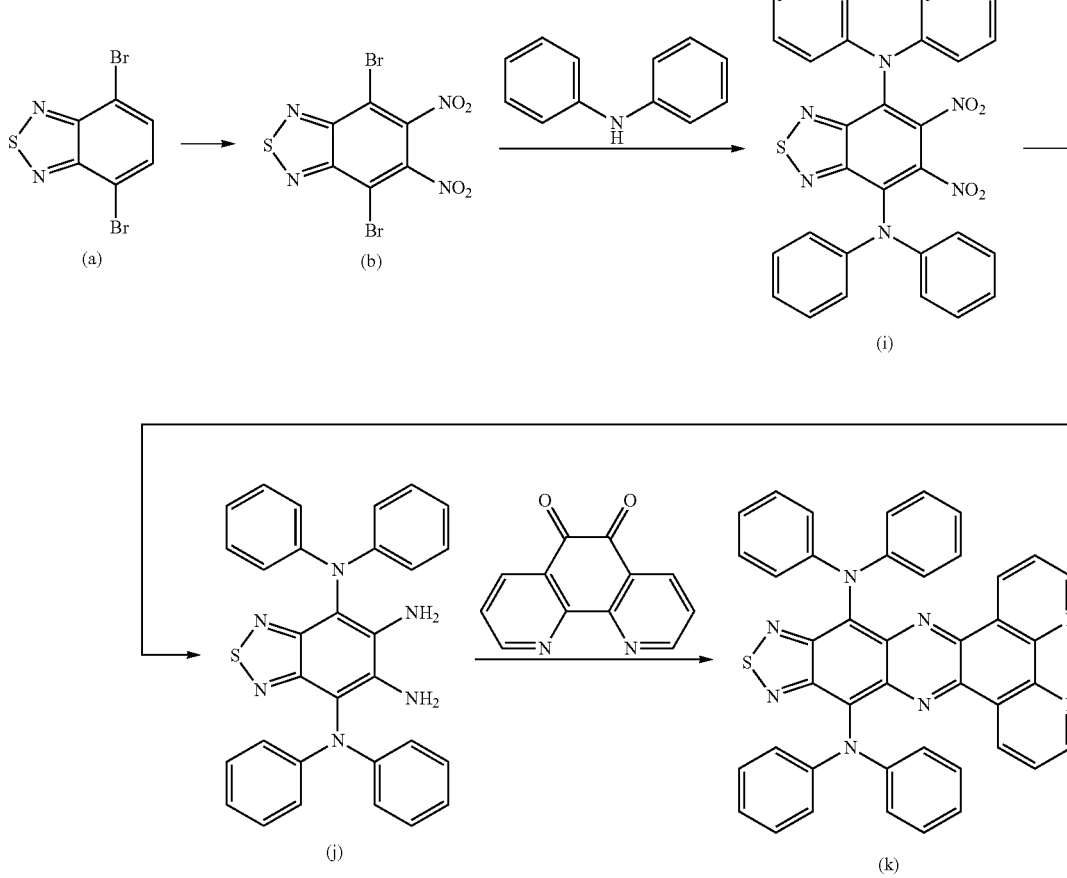

The same synthesis steps as in Synthesis Example A5 were repeated except phenylboronic acid used in Synthesis Step A5-2 in Synthesis Example A5 was replaced with diphenylamine. In this way, compound (k), i.e., compound D2-3, was obtained.

In this synthesis process, diphenylamine was used as follows. In an Ar atmosphere, 11 g of tetrakis(triphenyl) Pd (0) was put into a 300-mL flask and dissolved in 100 mL of toluene, and the solution was warmed to 100° C. After 8 g of tri-t-butylphosphine was added, the reaction was allowed to proceed for 30 minutes. The obtained product was used as catalyst (Pd catalyst).

The same procedure as Synthesis Step A5-4 in Synthesis Example A5 was then repeated with the obtained compound (j) and compound (k), i.e., compound D2-3, was obtained.

In this way, compound (k) (compound D2-3) was obtained as a deep navy blue solid weighing 3.2 g with an HPLC purity of 99%. The obtained compound (k) was analyzed by mass spectrometry and found to have an M$^+$ of 674.

The obtained compound (k) was then purified by sublimation at a set temperature of 360° C. The HPLC purity of the sublimation-purified compound (k) was 99%.

1-8. Synthesis Example A8, Synthesis of Compound D3-1

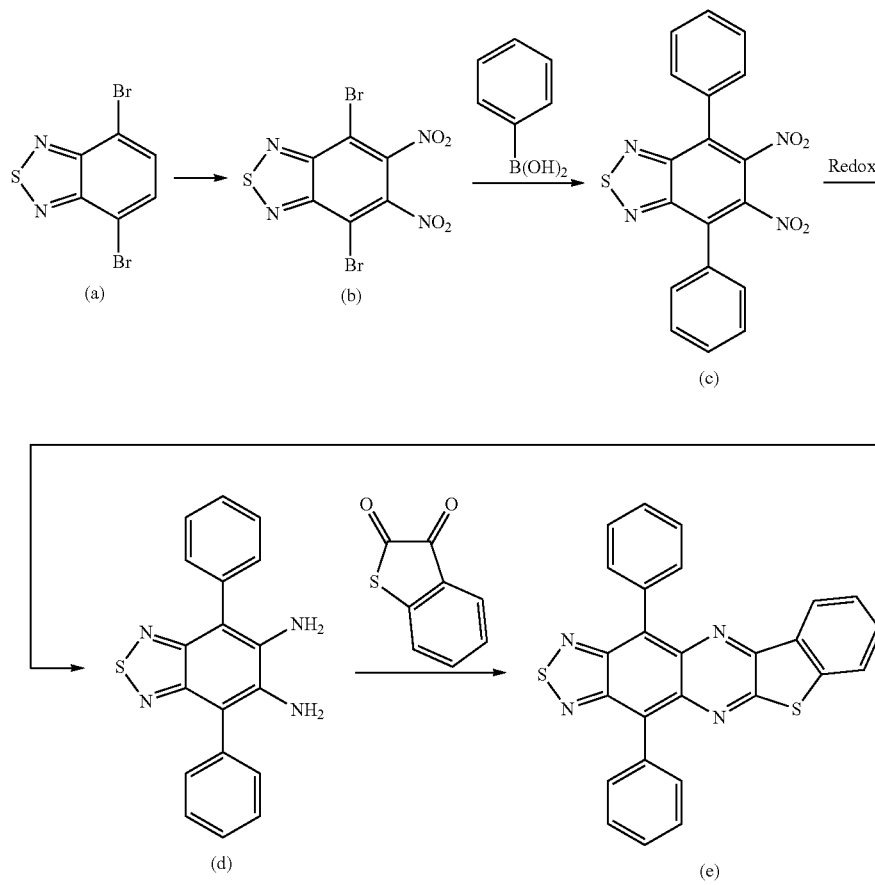

Synthesis Step A8-1

First, 1500 mL of fuming nitric acid was put into a 5-L flask and cooled. To this flask, 1500 mL of sulfuric acid was added in several portions so that the temperature was maintained at 10° C. to 50° C. Then 150 g of compound (a), raw material dibromobenzothiadiazole, was added in small amounts over 1 hour. The temperature of the solution was maintained at, 5° C. or less during this operation. After all of compound (a) was added, the reaction was allowed to proceed at room temperature (25° C.) for 20 hours. After the completion of the reaction, the reaction solution was poured into 3 kg of ice and stirred overnight. The solution was filtered, and the residue was washed with methanol and heptane.

The residue was then dissolved in 200 mL of toluene by heating. The solution was allowed to cool to room temperature and filtered. The residue was washed with a small amount of toluene and dried under reduced pressure.

In this way, 60 g of compound (b) (4,7-dibromo-5,6-dinitro-benzo[1,2,5]thiadiazole) was obtained with an HPLC purity of 95%.

Synthesis Step A8-2

In an Ar atmosphere, 30 g of the obtained dibromide (b), 23 g of phenylboronic acid (a commercially available product), 2500 mL of toluene, and a 2 M aqueous solution of cesium carbonate (152 g in 234 mL of distilled water) were put into a 5-L flask, and the reaction was allowed to proceed at 90° C. overnight. After the completion of the reaction, the solution was filtered and separated, and the isolated layer was concentrated. The resulting crude product, which weighed 52 g, was separated using a silica gel column (5 kg of $SiO_2$) and a red-purple solid was obtained.

In this way, 6 g of compound (c) (5,6-dinitro-4,7-diphenyl-benzo[1,2,5]thiadiazole) was obtained with an HPLC purity of 96%.

Synthesis Step A8-3

In an Ar atmosphere, the obtained dinitride (c), 6 g, was put into a 1-L flask with 7 g of reduced iron and 600 mL of acetic acid, the reaction was allowed to proceed at 80° C. for 4 hours, and the solution was allowed to cool to room temperature. After the completion of the reaction, the reaction solution was poured into 1.5 L of ion-exchanged water, and 1.5 L of ethyl acetate was added. Since a precipitate immediately appeared, 1 L of tetrahydrofuran and 300 g of sodium chloride were added, and the obtained solution was subjected to extraction and separation. The aqueous layer was subjected to another round of extraction with 1 L of tetrahydrofuran. The dry residue after evaporation was washed with small amounts of water and methanol and an orange solid was obtained.

In this way, 7 g of compound (d) (4,7-diphenyl-benzo[1,2,5]thiadiazole-5,6-diamine) was obtained with an HPLC purity of 80%.

Synthesis Step A8-4

In an Ar atmosphere, 4.5 g of the obtained diamine (d), 2.32 g of benzo[b]thiophene-2,3-dione, and 300 mL of acetic acid as solvent were put into a 1-L flask, and the reaction was allowed to proceed at 80° C. for 2 hours. After the completion of the reaction, the solution was allowed to cool to room temperature and poured into 1 L of ion-exchanged water. The resulting crystals were collected by filtration and washed with water, yielding a dark green solid weighing 6.5 g. This dark green solid was purified using a silica gel column (1 kg of SiO$_2$).

In this way, 4.0 g of compound (e) (compound D3-1) was obtained with an HPLC purity of 99%. The obtained compound (e) was analyzed by mass spectrometry and found to have an M$^+$ of 446.

The obtained compound (e) was then purified by sublimation at a set temperature of 340° C. The HPLC purity of the sublimation-purified compound (e) was 99%.

1-9. Synthesis Example A9, Synthesis of Compound D3-2

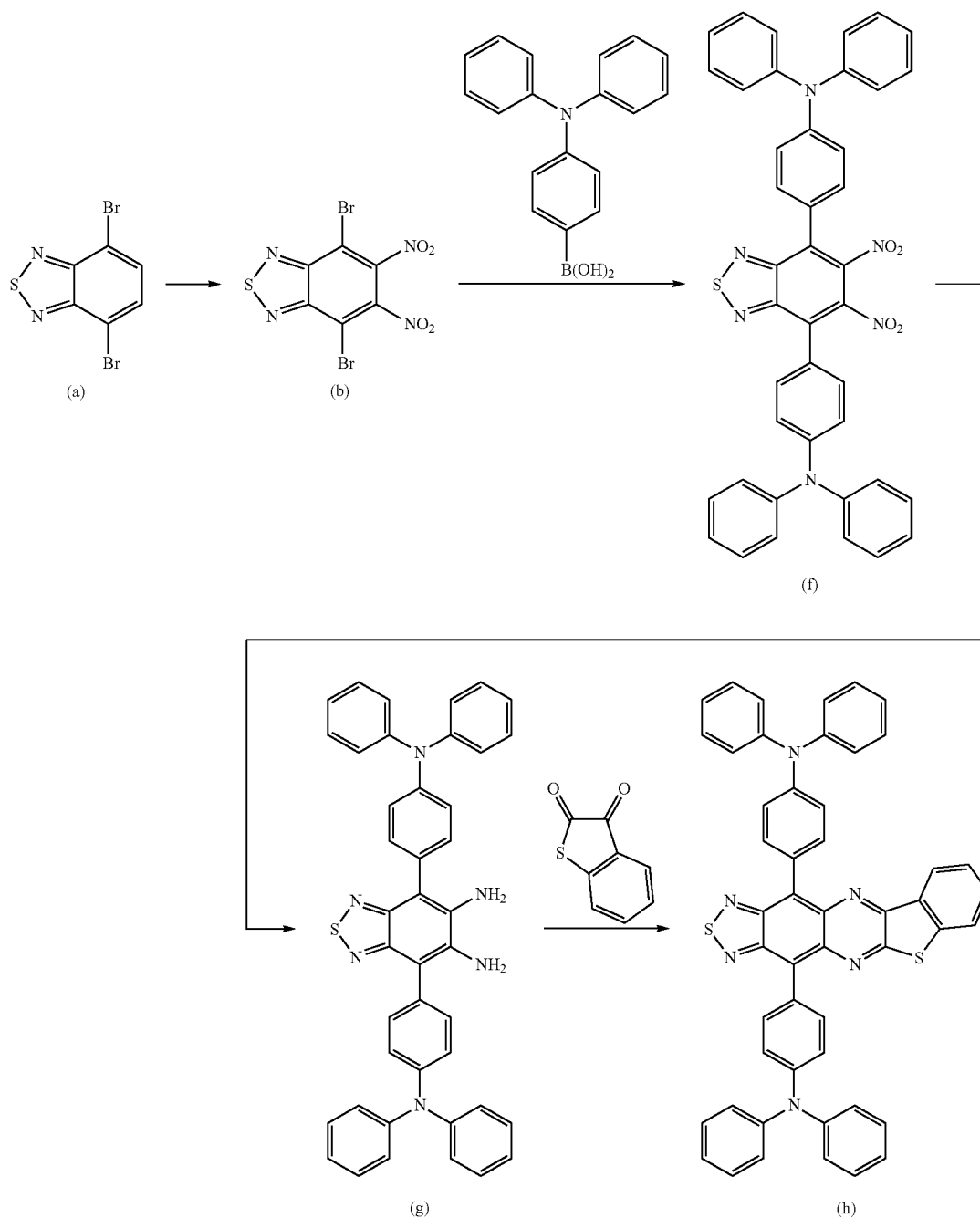

The same synthesis steps as in Synthesis Example A8 were repeated except phenylboronic acid used in Synthesis Step A8-2 in Synthesis Example A8 was replaced with a triphenylamine boronic acid. In this way, compound (h), i.e., compound D3-2, was obtained.

The triphenylamine boronic acid was synthesized by the following procedure. In an Ar atmosphere, 246 g of 4-bromotriphenylamine (a commercially available product) and 1500 mL of anhydrous tetrahydrofuran were put into a 5-L flask, and 570 mL of a 1.6 M n-BuLi solution in hexane was added dropwise at −60° C. over 3 hours. Thirty minutes later, 429 g of triisopropyl borate was added dropwise over In this way, compound (h) (compound D3-2) was obtained as a deep navy blue solid weighing 2.9 g with an HPLC purity of 99%. The obtained compound (h) was analyzed by mass spectrometry and found to have an $M^+$ of 780.

The obtained compound (h) was then purified by sublimation at a set temperature of 360° C. The HPLC purity of the sublimation-purified compound (h) was 99%.

1-10. Synthesis Example A10, Synthesis of Compound D3-3

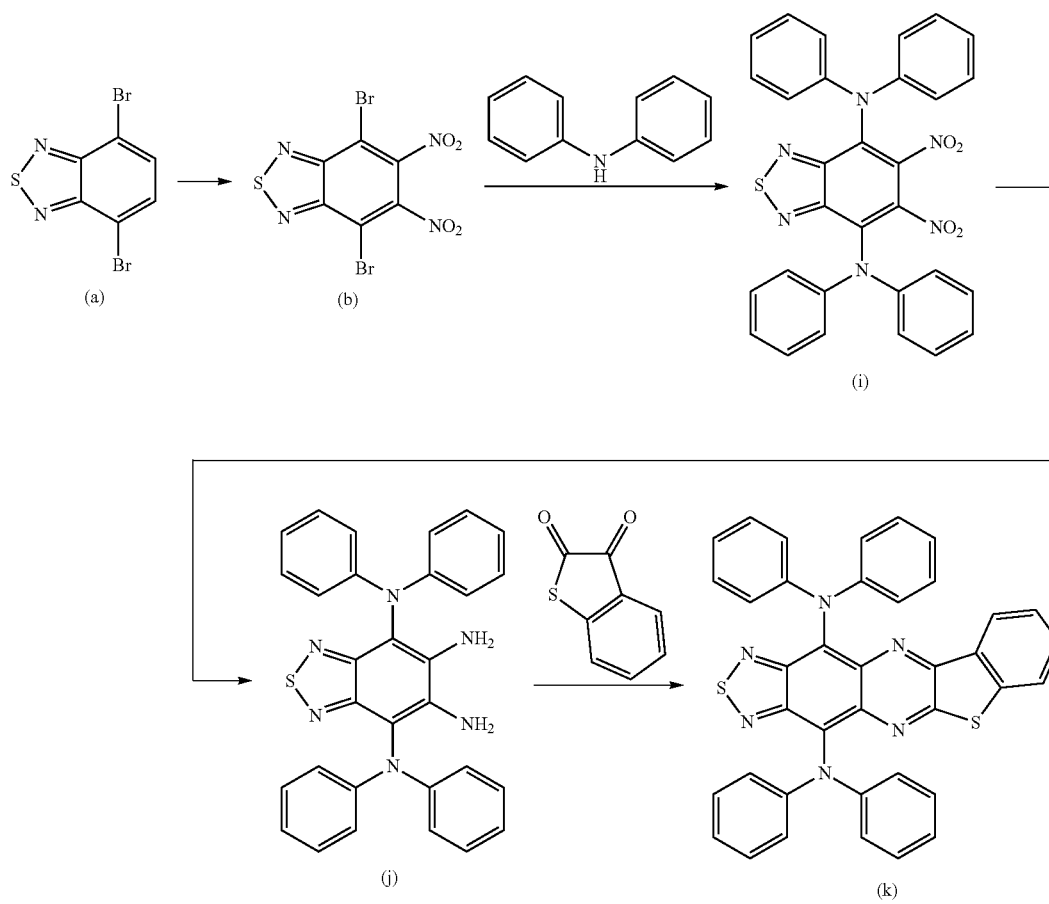

1 hour. Then the reaction was allowed to proceed overnight with no temperature control. After the completion of the reaction, 2 L of water was added dropwise, and the obtained solution was subjected to extraction and separation with 2 L of toluene. The organic layer was concentrated, the residue was recrystallized, and the crystals were collected by filtration and dried. In this way, the intended boronic acid was obtained as a white solid weighing 160 g.

The HPLC purity of the obtained boronic acid was 99%.

Then the same procedure as Synthesis Step A8-2 in Synthesis Example A8 was repeated with the obtained boronic acid and compound (f) was obtained.

The same procedure as Synthesis Step A8-3 in Synthesis Example A8 was then repeated with the obtained compound (f) and compound (g) was obtained.

Then the same procedure as Synthesis Step A8-4 in Synthesis Example A8 was repeated with the obtained compound (g) and compound (h), i.e., compound D3-2, was obtained.

The same synthesis steps as in Synthesis Example A8 were repeated except phenylboronic acid used in Synthesis Step A8-2 in Synthesis Example A8 was replaced with diphenylamine. In this way, compound (k), i.e., compound D3-3, was obtained.

In this synthesis process, diphenylamine was used as follows. In an Ar atmosphere, 11 g of tetrakis(triphenyl) Pd (0) was put into a 300-mL flask and dissolved in 100 mL of toluene, and the solution was warmed to 100° C. After 8 g of tri-t-butylphosphine was added, the reaction was allowed to proceed for 30 minutes. The obtained product was used as catalyst (Pd catalyst).

Separately, in an Ar atmosphere, 30 g of the dibromide (b) and 33 g of diphenylamine (a commercially available product) were put into a 5-L flask and dissolved in 2500 mL of toluene, and the solution was warmed to 100° C. The Pd catalyst and 20 g of t-BuOK were added, and the solution was heated to reflux for 3 hours.

After the reaction was complete and the solution cooled to room temperature, 100 mL of water was added, and the solution was stirred for approximately 1 hour. The solution was then transferred to a separatory funnel, combined with an additional amount of water, and separated. The organic layer was collected and dried. The obtained solid was separated using a silica gel column (5 kg of SiO$_2$) and a purple solid was obtained.

In this way, 10 g of compound (i) (5,6-dinitro-N,N,N',N'-tetraphenyl-benzo[1,2,5]thiadiazole) was obtained with an HPLC purity of 96%.

Then the same procedure as Synthesis Step A8-3 in Synthesis Example A8 was repeated with the obtained compound (i) and compound (j) was obtained.

The same procedure as Synthesis Step A8-4 in Synthesis Example A8 was then repeated with the obtained compound (j) and compound (k), i.e., compound D3-3, was obtained.

In this way, compound (k) (compound D3-3) was obtained as a deep navy blue solid weighing 2.9 g with an HPLC purity of 99%. The obtained compound (k) was analyzed by mass spectrometry and found to have an M$^+$ of 628.

The obtained compound (k) was then purified by sublimation at a set temperature of 360° C. The HPLC purity of the sublimation-purified compound (k) was 99%.

2. Preparation of a Host Material (A Tetracene-Based Material)

Synthesis Example B1, Synthesis of Compound H1-2

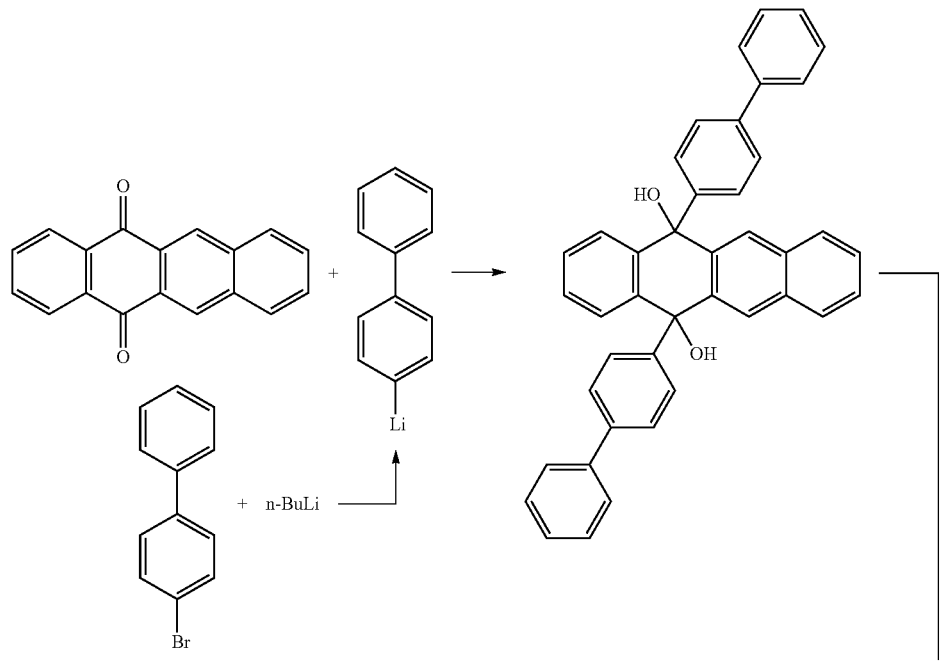

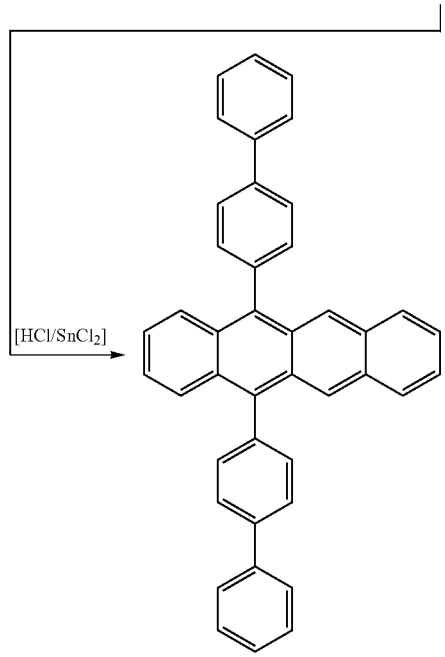

Synthesis Step B1-1

In an Ar atmosphere, 6 g of 4-bromobiphenyl and 50 mL of dry diethyl ether were put into a 300-mL flask. Then 14.5 mL of a 1.6 M n-BuLi solution in hexane was added dropwise at room temperature, and the reaction was allowed to proceed for 30 minutes.

Separately, in an Ar atmosphere, 2.7 g of 5,12-naphthacenequinone and 100 mL of dry toluene were put into a 500-mL flask. The lithium biphenyl solution prepared in the previous step was added dropwise, and the reaction was allowed to proceed for 3 hours. After the completion of the reaction, 20 mL of distilled water was added. The obtained solution was stirred for 30 minutes and poured into methanol, and the resulting solid was isolated by filtration. The obtained solid was purified using silica gel (500 g of $SiO_2$).

In this way, a white solid weighing 4.5 g (5,12-bis (biphenyl-4-yl)-5,12-dihydronaphthacene-5,12-diol) was obtained.

Synthesis Step B1-2

The diol obtained in Synthesis Step B1-1, 4.5 g, and 300 mL of acetic acid were put into a 1000-mL flask. A solution of 5 g of tin chloride (II) (anhydrous) in 5 g of hydrochloric acid (35%) was added, and the mixed solution was stirred for 30 minutes. The solution was then transferred to a separatory funnel, toluene was added, the obtained solution was washed with distilled water by separation, and the residue was dried. The obtained solid was purified using silica gel (500 g of $SiO_2$) and a yellow solid weighing 4 g (compound H1-2) was obtained.

Synthesis Example B2, Synthesis of Compound H1-5

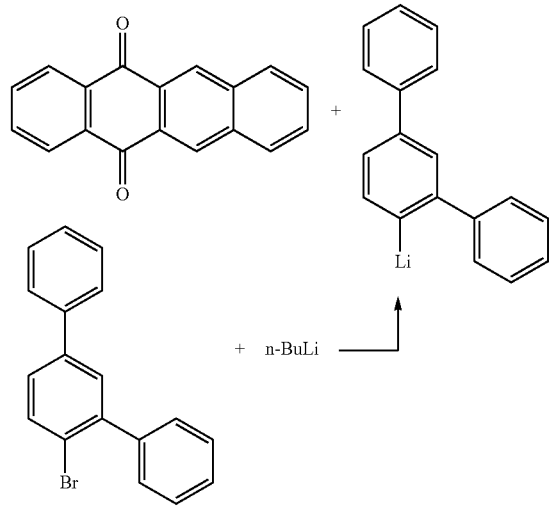
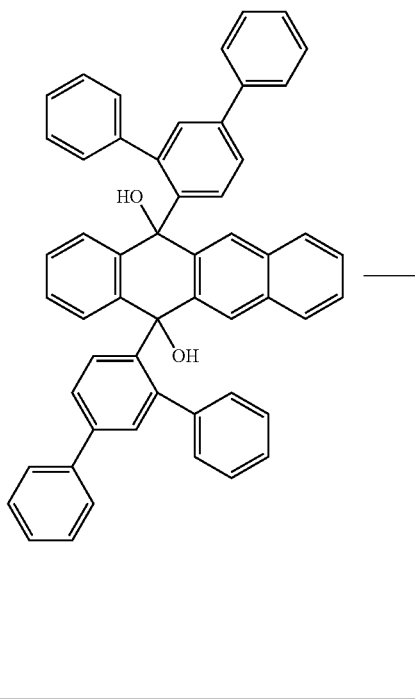
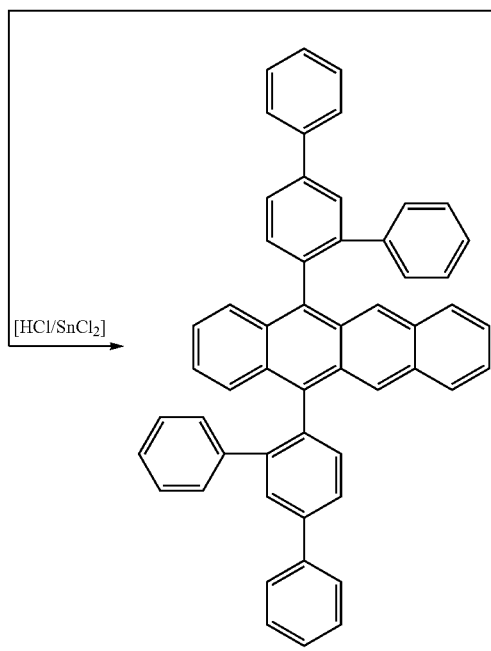

Synthesis Step B2-1

In an Ar atmosphere, 6 g of 4'-bromo-[1,1',3',1"]terphenyl and 50 mL of dry diethyl ether were put into a 300-mL flask. Then 14.5 mL of a 1.6 M n-BuLi solution in hexane was added dropwise at room temperature, and the reaction was allowed to proceed for 30 minutes.

Separately, in an Ar atmosphere, 2 g of 5,12-naphthacenequinone and 100 mL of dry toluene were put into a 500-mL flask. The lithium terphenyl solution prepared in the previous step was added dropwise, and the reaction was allowed to proceed for 3 hours. After the completion of the reaction, 20 mL of distilled water was added. The obtained solution was stirred for 30 minutes and poured into methanol, and the resulting solid was isolated by filtration. The obtained solid was purified using silica gel (500 g of $SiO_2$).

In this way, a white solid weighing 5 g (5,12-bis([1,1',3',1"]terphenyl-4'-yl)-5,12-dihydronaphthacene-5,12-diol) was obtained.

Synthesis Step B2-2

The diol obtained in Synthesis Step B2-1, 5 g, and 300 mL of acetic acid were put into a 1000-mL flask. A solution of 5 g of tin chloride (II) (anhydrous) in 5 g of hydrochloric acid (35%) was added, and the mixed solution was stirred for 30 minutes. The solution was then transferred to a separatory funnel, toluene was added, the obtained solution was washed with distilled water by separation, and the residue was dried. The obtained solid was purified using silica gel (500 g of $SiO_2$) and a yellow solid weighing 4.5 g (compound H1-5) was obtained.

Synthesis Example B3, Synthesis of Compound H1-13

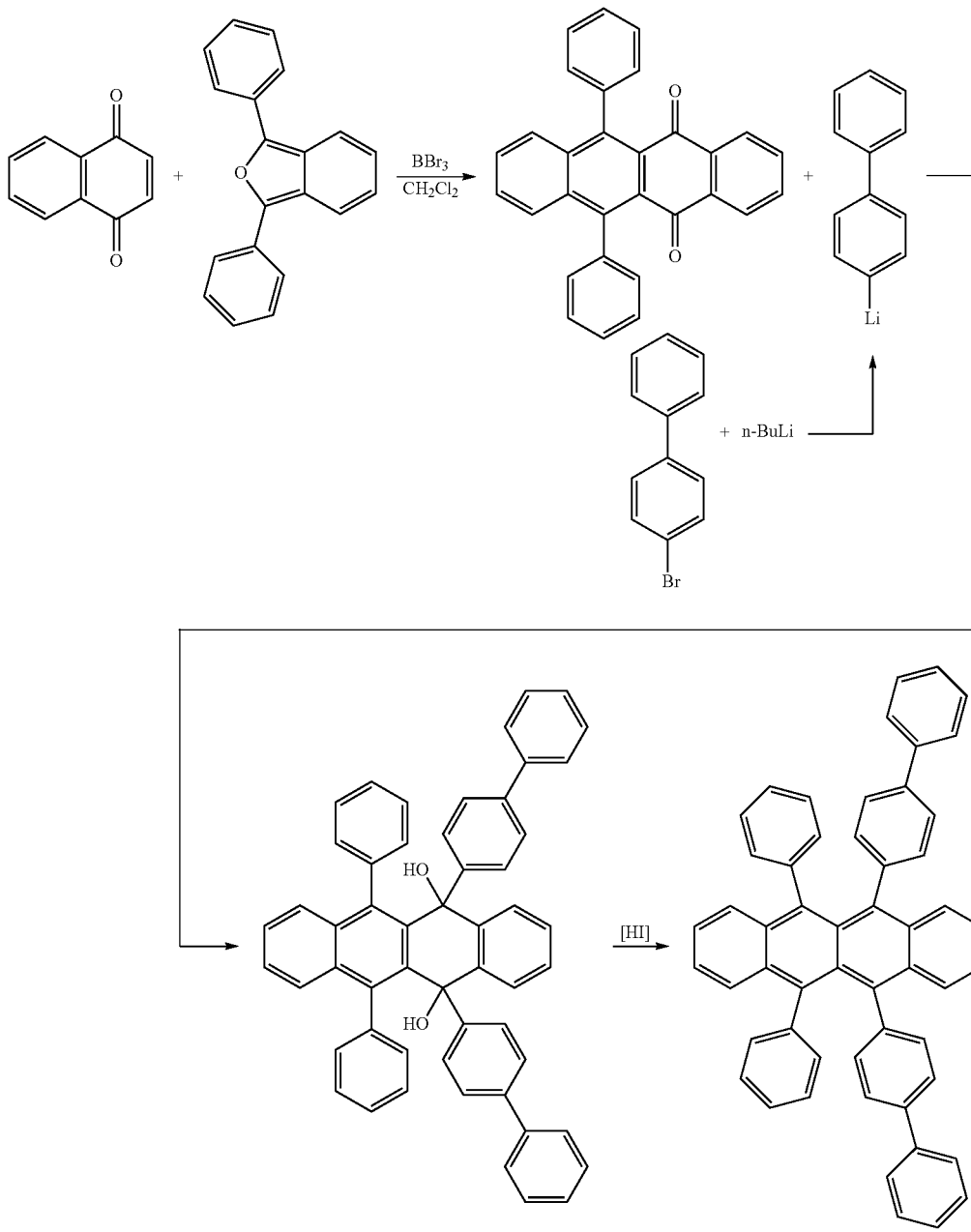

Synthesis Step B3-1

First, 100 mL of dichloromethane, 5.2 g of naphthoquinone, and 10 g of 1,3-diphenylisobenzofuran were put into a 500-mL flask, and the mixture was stirred for 1 hour. Then 33 mL of a commercially available boron tribromide (a 1 mol/L solution in dichloromethane) was added over 10 minutes and yellow needle crystals weighing 7.1 g (6,11-diphenyl-5,12-naphthacenequinone) were obtained.

Synthesis Step B3-2

In an Ar atmosphere, 6 g of 4-bromobiphenyl and 80 mL of dry diethyl ether were put into a 200-mL flask. Then 16 mL of a 1.6 M n-BuLi solution in hexane was added dropwise at room temperature, and the reaction was allowed to proceed for 30 minutes.

Separately, in an Ar atmosphere, 4.2 g of the quinone obtained in Synthesis Step B3-1 and 100 mL of dry toluene were put into a 500-mL flask. The lithium biphenyl solution prepared in the previous step was added dropwise, and the reaction was allowed to proceed for 3 hours. After the completion of the reaction, 20 mL of distilled water was added. The obtained solution was stirred for 30 minutes and poured into methanol, and the resulting solid was isolated by filtration. The obtained solid was purified using silica gel (500 g of $SiO_2$).

In this way, a white solid weighing 5.5 g (5,12-bis (biphenyl-4-yl)-6,11-diphenyl-5,12-dihydronaphthacene-5,12-diol) was obtained.

Synthesis Step B3-3

Five grams of the diol obtained in Synthesis Step B3-2 and 200 mL of tetrahydrofuran were put into a 500-mL flask. Then 10 g of hydroiodic acid (a 55% aqueous solution) was added, and the mixed solution was stirred for 2 hours under protection from light. The solution was then transferred to a separatory funnel, toluene was added, the obtained solution was washed with distilled water by separation, and the residue was dried. The obtained solid was purified using silica gel (500 g of $SiO_2$) and a red solid weighing 3 g (compound H1-13) was obtained.

3. Preparation of a Host Material (An Anthracene-Based Material)

Synthesis Example C1, Synthesis of Compound H2-30

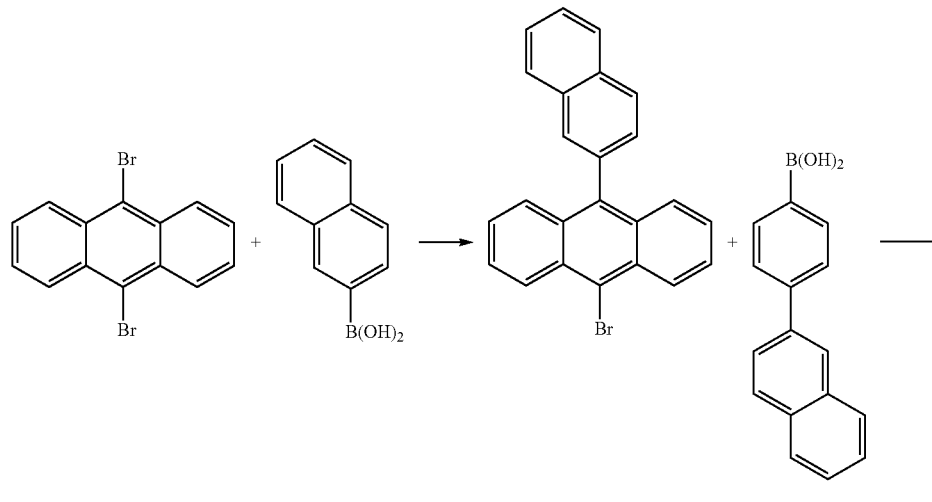

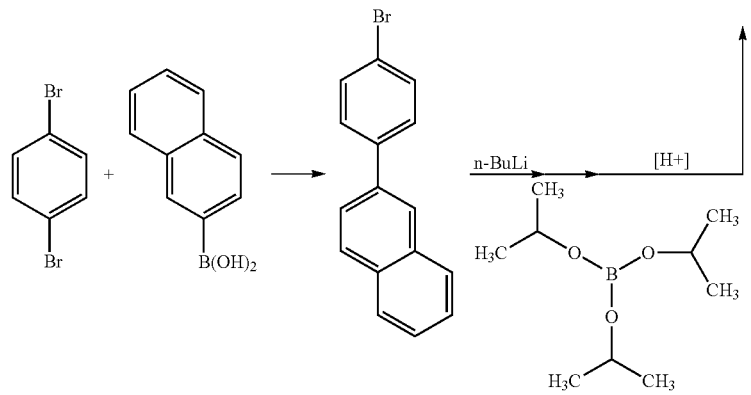

-continued

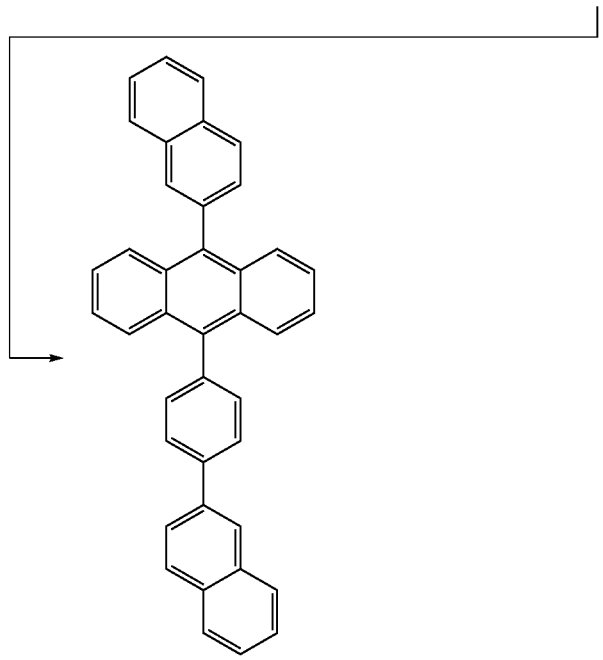

Synthesis Step C1-1

First, 2.1 g of a commercially available 2-naphthalene boronic acid and 5 g of 9,10-dibromoanthracene were dissolved in 50 mL of dimethoxyethane, and the obtained solution was heated to 80° C. To the heated solution 50 mL of distilled water and 10 g of sodium carbonate were added. Then 0.4 g of tetrakis(triphenylphosphine)palladium (0) was added.

Three hours later, the solution was put into a separatory funnel and subjected to extraction with toluene, and the extract was purified using silica gel (500 g of $SiO_2$).

In this way, pale yellowish-white crystals weighing 3 g (9-bromo-10-naphthalen-2-yl-anthracene) were obtained.

Synthesis Step C1-2

In an Ar atmosphere, 10.5 g of a commercially available 2-naphthalene boronic acid and 17.5 g of 1,4-dibromobenzene were dissolved in 250 mL of dimethoxyethane in a 500-mL flask, and the obtained solution was heated to 80° C. To the heated solution 250 mL of distilled water and 30 g of sodium carbonate were added. Then 2 g of tetrakis(triphenylphosphine)palladium (0) was added.

Three hours later, the solution was put into a separatory funnel and subjected to extraction with toluene, and the extract was purified using silica gel (500 g of $SiO_2$).

In this way, white crystals weighing 10 g (2-(4-bromophenyl)-naphthalene) were obtained.

Synthesis Step C1-3

In an Ar atmosphere, the 2-(4-bromophenyl)-naphthalene crystals obtained in Synthesis Step C1-2, 10 g, and 500 mL of anhydrous tetrahydrofuran were put into a 1-L flask, and 22 mL of a 1.6 M n-BuLi solution in hexane was added dropwise at −60° C. over 30 minutes. Thirty minutes later, 7 g of triisopropyl borate was added dropwise, and the reaction was allowed to proceed overnight with no temperature control. After the completion of the reaction, 100 mL of water was added dropwise, and the obtained solution was subjected to extraction and separation with 2 L of toluene. The organic layer was concentrated, the residue was recrystallized, and the crystals were collected by filtration and dried. In this way, a phenylboronic acid derivative was obtained as a white solid weighing 5 g.

Synthesis Step C1-4

In an Ar atmosphere, the 9-bromo-10-naphthalen-2-yl-anthracene crystals obtained in Synthesis Step C1-1, 3 g, and 3 g of the boronic acid obtained in Synthesis Step C1-3 were dissolved in 200 mL of dimethoxyethane in a 500-mL flask, and the obtained solution was heated to 80° C. To the heated solution 250 mL of distilled water and 10 g of sodium carbonate were added. Then 0.5 g of tetrakis(triphenylphosphine)palladium (0) was added.

Three hours later, the solution was put into a separatory funnel and subjected to extraction with toluene, and the extract was purified by silica gel chromatography.

In this way, a pale yellowish-white solid weighing 3 g (compound H2-30) was obtained.

Synthesis Example C2, Synthesis of Compound H2-47

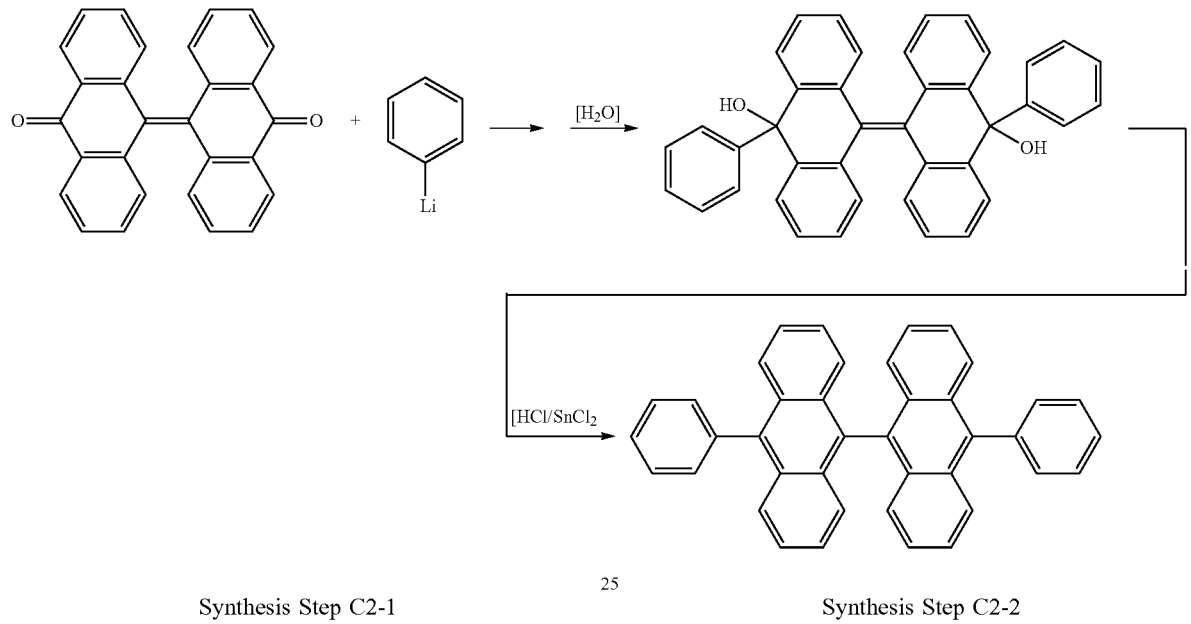

Synthesis Step C2-1

In an Ar atmosphere, 5 g of bianthrone and 150 mL of dry diethyl ether were put into a 300-mL flask. Then 5.5 mL of a commercially available phenyllithium reagent (a 19% solution in butyl ether) was added, and the obtained mixture was stirred at room temperature for 3 hours. After 10 mL of water was added, the solution was transferred to a separatory funnel, the desired substance was extracted into toluene, the extract was dried, and the residue was purified by separation using silica gel (500 g of SiO$_2$).

In this way, the intended compound (10,10'-diphenyl-10H,10'H-[9,9']bianthracenylidene-10,10'-diol) was obtained as a white solid weighing 5 g.

Synthesis Step C2-2

The diol obtained in Synthesis Step C2-1, 5 g, and 300 mL of acetic acid were put into a 500-mL flask. A solution of 5 g of tin chloride (II) (anhydrous) in 5 g of hydrochloric acid (35%) was added, and the mixed solution was stirred for 30 minutes. The solution was then transferred to a separatory funnel, toluene was added, the obtained solution was washed with distilled water by separation, and the residue was dried. The obtained solid was purified using silica gel (500 g of SiO$_2$), and a yellowish-white solid weighing 5.5 g (compound H2-47) was obtained.

Synthesis Example C3, Synthesis of Compound H2-52

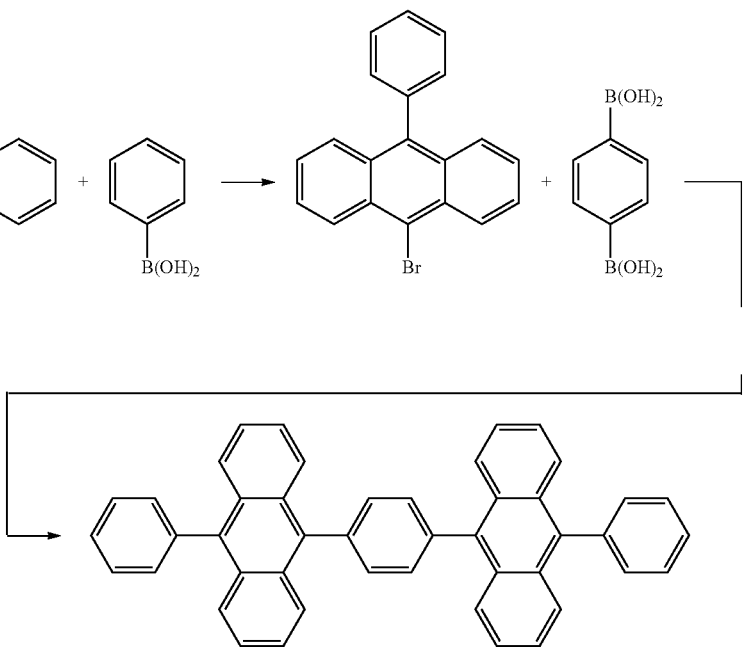

Synthesis Step C3-1

First, 2.2 g of a commercially available phenylboronic acid and 6 g of 9,10-dibromoanthracene were dissolved in 100 mL of dimethoxyethane, and the obtained solution was heated to 80° C. To the heated solution 50 mL of distilled water and 10 g of sodium carbonate were added. Then 0.5 g of tetrakis(triphenylphosphine)palladium (0) was added.

Three hours later, the solution was put into a reparatory funnel and subjected to extraction with toluene, and the extract was purified using silica gel (500 g of $SiO_2$).

In this way, yellowish-white crystals weighing 4 g (9-bromo-10-phenylanthracene) were obtained.

Synthesis Step C3-2

In an Ar atmosphere, the 9-bromo-10-phenylanthracene crystals obtained in Synthesis Step C3-1, 4 g, and 0.8 g of a commercially available phenylenediboronic acid were dissolved in 200 mL of dimethoxyethane in a 500-mL flask, and the obtained solution was heated to 80° C. To the heated solution 250 mL of distilled water and 10 g of sodium carbonate were added. Then 0.5 g of tetrakis(triphenylphosphine)palladium (0) was added.

Three hours later, the solution was put into a separatory funnel and subjected to extraction with toluene, and the extract was purified by silica gel chromatography.

In this way, a pale yellowish-white solid weighing 2 g (compound H2-52) was obtained.

4. Preparation of an Electron Transport Material (an Azaindolizine)

Synthesis Example E1, Synthesis of Compound ETL-A3

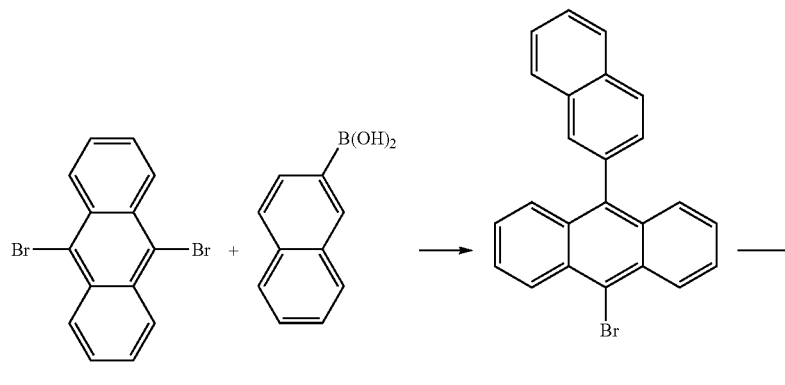

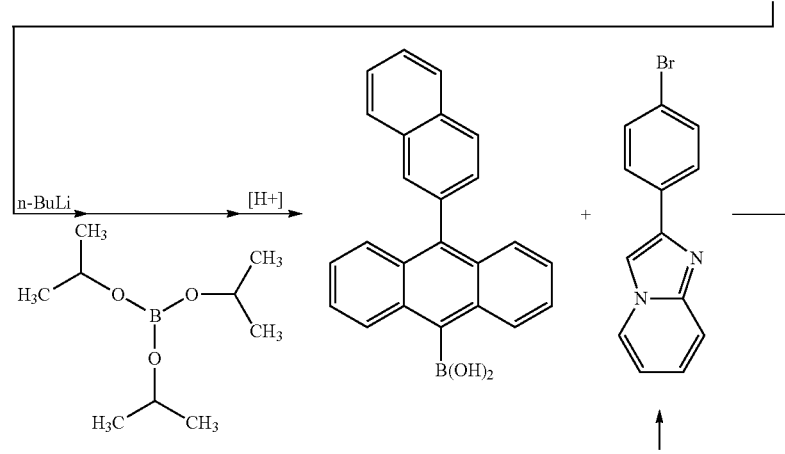

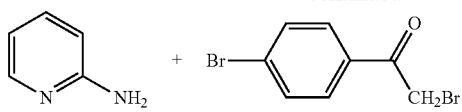

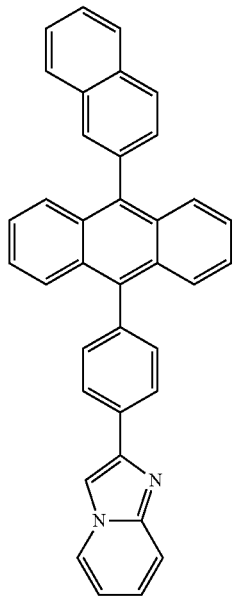

Synthesis Step E1-1

First, 2.1 g of a commercially available 2-naphthaleneboronic acid and 5 g of 9,10-dibromoanthracene were dissolved in 50 mL of dimethoxyethane, and the obtained solution was heated to 80° C. To the heated solution 50 mL of distilled water and 10 g of sodium carbonate were added. Then 0.4 g of tetrakis(triphenylphosphine)palladium (0) was added.

Three hours later, the solution was put into a separatory funnel and subjected to extraction with toluene, and the extract was purified using silica gel (500 g of $SiO_2$).

In this way, pale yellowish-white crystals weighing 3 g (9-bromo-10-naphthalen-2-yl-anthracene) were obtained.

Synthesis Step E1-2

In an Ar atmosphere, the 9-bromo-10-naphthalen-2-yl-anthracene crystals obtained in Synthesis Step E1-1, 3 g, and 500 mL of anhydrous tetrahydrofuran were put into a 1-L flask, and 6 mL of a 1.6 M n-BuLi solution in hexane was added dropwise at −60° C. over 10 minutes. Thirty minutes later, 1.5 g of triisopropyl borate was added dropwise, and the reaction was allowed to proceed for 3 hours with no temperature control. After the completion of the reaction, 50 mL of distilled water was added dropwise, and the obtained solution was subjected to extraction and separation with 1 L of toluene. The organic layer was concentrated, the residue was recrystallized, and the crystals were collected by filtration and dried. In this way, the intended substance (a boronic acid) was obtained as a white solid weighing 2 g.

Synthesis Step E1-3

In an Ar atmosphere, 3.4 g of 2-aminopyridine was put into a 300-mL flask and dissolved by adding 40 mL of ethanol and 40 mL of acetone. After 10 g of 4-bromophenacyl bromide was added, the solution was heated to reflux. Three hours later, heating was stopped and the mixture was allowed to cool to room temperature. The solvent was removed under reduced pressure, and the residue was heated and dissolved in 1 L of methanol. Insoluble impurities were filtered out, and the filtrate was concentrated. The resulting precipitate was collected.

In this way, the intended compound (2-(4-bromophenyl)-imidazo[1,2-a]pyridine) was obtained as a white solid weighing 8 g.

Synthesis Step E1-4

In an Ar atmosphere, the boronic acid obtained in Synthesis Step E1-2, 2 g, and 1.7 g of the imidazopyridine derivative obtained in Synthesis Step E1-3 were dissolved in 200 mL of dimethoxyethane in a 500-mL flask, and the obtained solution was heated to 80° C. To the heated solution 250 mL of distilled water and 10 g of sodium carbonate were added. Then 0.5 g of tetrakis(triphenylphosphine)palladium (0) was added.

Three hours later, the solution was put into a separatory funnel and subjected to extraction with toluene, and the extract was purified using silica gel (500 g of $SiO_2$).

In this way, a white solid weighing 2 g (compound ETL-A3) was obtained.

5. Preparation of a Light-Emitting Element

Example 1-1

I. A transparent glass substrate having an average thickness of 0.5 mm was prepared. An ITO electrode (the anode) having an average thickness of 100 nm was then formed on the substrate by sputtering.

The substrate was immersed in acetone and then in 2-propanol, cleaned by sonication, and subjected to oxygen plasma treatment and argon plasma treatment. Prior to each round of plasma treatment, the substrate was warmed to a temperature of 70° C. to 90° C. The conditions were common to both treatments and were as follows: plasma power, 100 W; gas flow rate, 20 sccm; treatment duration, 5 seconds.

II. A layer of compound HTL-3, an amine-based hole transport material, was formed on the ITO electrode by vacuum deposition as a hole transport layer having an average thickness of 60 nm.

III. A light-emitting layer having an average thickness of 25 nm was formed by depositing a layer of the constituent materials of the light-emitting layer on the hole transport layer by vacuum deposition. The constituent materials of the light-emitting layer were compound D1-2 as light-emitting material (the guest material) and compound H1-2 as host material (a tetracene-based material). The light-emitting material (dopant) content (doping level) of the light-emitting layer was 4.0 wt %.

IV. A layer of compound ETL-A3 was formed on the light-emitting layer by vacuum deposition as an electron transport layer having an average thickness of 90 nm.

V. A layer of lithium fluoride (LiF) was formed on the electron transport layer by vacuum deposition as an electron injection layer having an average thickness of 1 nm.

VI. A layer of Al was formed on the electron injection layer by vacuum deposition as an Al cathode having an average thickness of 100 nm.

VII. A glass cover (the sealing member) was put over the formed layers and fixed and sealed with epoxy resin.

By these operations, a light-emitting element was prepared.

Example 1-2

A light-emitting element was prepared in the same way as in Example 1-1 except that the host material in the light-emitting layer was compound H1-5 (a tetracene-based material).

Example 1-3

A light-emitting element was prepared in the same way as in Example 1-1 except that the host material in the light-emitting layer was compound H1-13 (a tetracene-based material).

Example 1-4

A light-emitting element was prepared in the same way as in Example 1-1 except that the host material in the light-emitting layer was compound H2-30 (an anthracene-based material).

Example 1-5

A light-emitting element was prepared in the same way as in Example 1-1 except that the host material in the light-emitting layer was compound H2-47 (an anthracene-based material).

Example 1-6

A light-emitting element was prepared in the same way as in Example 1-1 except that the host material in the light-emitting layer was compound H2-52 (an anthracene-based material).

Example 1-7

A light-emitting element was prepared in the same way as in Example 1-1 except that the host material in the light-emitting layer was Alq$_3$.

Example 1-8

A light-emitting element was prepared in the same way as in Example 1-1 except that the light-emitting material (dopant) content (doping level) of the light-emitting layer was 1.0 wt %.

Example 1-9

A light-emitting element was prepared in the same way as in Example 1-1 except that the light-emitting material (dopant) content (doping level) of the light-emitting layer was 2.0 wt %.

Example 1-10

A light-emitting element was prepared in the same way as in Example 1-1 except that the light-emitting material (dopant) content (doping level) of the light-emitting layer was 10.0 wt %.

Example 1-11

A light-emitting element was prepared in the same way as in Example 1-1 except that the average thickness of the light-emitting layer was 15 nm and the average thickness of the electron transport layer was 100 nm.

Example 1-12

A light-emitting element was prepared in the same way as in Example 1-1 except that the average thickness of the light-emitting layer was 50 nm and the average thickness of the electron transport layer was 65 nm.

Example 1-13

A light-emitting element was prepared in the same way as in Example 1-1 except that the average thickness of the light-emitting layer was 70 nm and the average thickness of the electron transport layer was 45 nm.

Example 1-14

A light-emitting element was prepared in the same way as in Example 1-1 except that the light-emitting material in the light-emitting layer was compound D1-4.

Example 1-15

A light-emitting element was prepared in the same way as in Example 1-1 except that the light-emitting material in the light-emitting layer was compound D1-5.

Example 1-16

A light-emitting element was prepared in the same way as in Example 1-1 except that the light-emitting material in the light-emitting layer was compound D1-8.

Reference Example 1-1

A light-emitting element was prepared in the same way as in Example 1-1 except that the light-emitting material (dopant) in the light-emitting layer was omitted (the light-emitting layer was composed solely of compound H1-2).

Reference Example 1-2

A light-emitting element was prepared in the same way as in Example 1-1 except that the electron transport layer was made of 2,9-dimethyl-4,7-diphenyl-1,10-phenanthroline (BCP).

Example 2-1

I. A transparent glass substrate having an average thickness of 0.5 mm was prepared. An ITO electrode (the anode) having an average thickness of 100 nm was then formed on the substrate by sputtering.

The substrate was immersed in acetone and then in 2-propanol, cleaned by sonication, and subjected to oxygen plasma treatment and argon plasma treatment. Prior to each round of plasma treatment, the substrate was warmed to a temperature of 70° C. to 90° C. The conditions were common to both treatments and were as follows: plasma power, 100 W; gas flow rate, 20 sccm; treatment duration, 5 seconds.

II. A layer of compound HTL-3, an amine-based hole transport material, was formed on the ITO electrode by vacuum deposition as a hole transport layer having an average thickness of 60 nm.

III. A light-emitting layer having an average thickness of 25 nm was formed by depositing a layer of the constituent materials of the light-emitting layer on the hole transport layer by vacuum deposition. The constituent materials of the light-emitting layer were compound D2-2 as light-emitting material (the guest material) and compound H1-2 as host material (a tetracene-based material). The light-emitting material (dopant) content (doping level) of the light-emitting layer was 4.0 wt %.

IV. A layer of compound ETL-A3 was formed on the light-emitting layer by vacuum deposition as an electron transport layer having an average thickness of 90 nm.

V. A layer of lithium fluoride (LiF) was formed on the electron transport layer by vacuum deposition as an electron injection layer having an average thickness of 1 nm.

VI. A layer of Al was formed on the electron injection layer by vacuum deposition as an Al cathode having an average thickness of 100 nm.

VII. A glass cover (the sealing member) was put over the formed layers and fixed and sealed with epoxy resin.

By these operations, a light-emitting element was prepared.

Example 2-2

A light-emitting element was prepared in the same way as in Example 2-1 except that the host material in the light-emitting layer was compound H1-5 (a tetracene-based material).

Example 2-3

A light-emitting element was prepared in the same way as in Example 2-1 except that the host material in the light-emitting layer was compound H1-13 (a tetracene-based material).

Example 2-4

A light-emitting element was prepared in the same way as in Example 2-1 except that the host material in the light-emitting layer was compound H2-30 (an anthracene-based material).

Example 2-5

A light-emitting element was prepared in the same way as in Example 2-1 except that the host material in the light-emitting layer was compound H2-47 (an anthracene-based material).

Example 2-6

A light-emitting element was prepared in the same way as in Example 2-1 except that the host material in the light-emitting layer was compound H2-52 (an anthracene-based material).

Example 2-7

A light-emitting element was prepared in the same way as in Example 2-1 except that the host material in the light-emitting layer was $Alq_3$.

Example 2-8

A light-emitting element was prepared in the same way as in Example 2-1 except that the light-emitting material (dopant) content (doping level) of the light-emitting layer was 1.0 wt %.

Example 2-9

A light-emitting element was prepared in the same way as in Example 2-1 except that the light-emitting material (dopant) content (doping level) of the light-emitting layer was 2.0 wt %.

Example 2-10

A light-emitting element was prepared in the same way as in Example 2-1 except that the light-emitting material (dopant) content (doping level) of the light-emitting layer was 10.0 wt %.

Example 2-11

A light-emitting element was prepared in the same way as in Example 2-1 except that the average thickness of the light-emitting layer was 15 nm and the average thickness of the electron transport layer was 100 nm.

Example 2-12

A light-emitting element was prepared in the same way as in Example 2-1 except that the average thickness of the light-emitting layer was 50 nm and the average thickness of the electron transport layer was 65 nm.

Example 2-13

A light-emitting element was prepared in the same way as in Example 2-1 except that the average thickness of the light-emitting layer was 70 nm and the average thickness of the electron transport layer was 45 nm.

Example 2-14

A light-emitting element was prepared in the same way as in Example 2-1 except that the light-emitting material in the light-emitting layer was compound D2-1.

Example 2-15

A light-emitting element was prepared in the same way as in Example 2-1 except that the light-emitting material in the light-emitting layer was compound D2-3.

Reference Example 2-1

A light-emitting element was prepared in the same way as in Example 2-1 except that the light-emitting material (dopant) in the light-emitting layer was omitted (the light-emitting layer was composed solely of compound H1-2).

Reference Example 2-2

A light-emitting element was prepared in the same way as in Example 2-1 except that the electron transport layer was made of 2,9-dimethyl-4,7-diphenyl-1,10-phenanthroline (BCP).

Example 3-1

I. A transparent glass substrate having an average thickness of 0.5 mm was prepared. An ITO electrode (the anode) having an average thickness of 100 nm was then formed on the substrate by sputtering.

The substrate was immersed in acetone and then in 2-propanol, cleaned by sonication, and subjected to oxygen plasma treatment and argon plasma treatment. Prior to each round of plasma treatment, the substrate was warmed to a temperature of 70° C. to 90° C. The conditions were common to both treatments and were as follows: plasma power, 100 W; gas flow rate, 20 sccm; treatment duration, 5 seconds.

II. A layer of compound HTL-3, an amine-based hole transport material, was formed on the ITO electrode by vacuum deposition as a hole transport layer having an average thickness of 60 nm.

III. A light-emitting layer having an average thickness of 25 nm was formed by depositing a layer of the constituent materials of the light-emitting layer on the hole transport layer by vacuum deposition. The constituent materials of the light-emitting layer were compound D3-2 as light-emitting material (the guest material) and compound H1-2 as host material (a tetracene-based material). The light-emitting material (dopant) content (doping level) of the light-emitting layer was 4.0 wt %.

IV. A layer of compound ETL-A3 was formed on the light-emitting layer by vacuum deposition as an electron transport layer having an average thickness of 90 nm.

V. A layer of lithium fluoride (LiF) was formed on the electron transport layer by vacuum deposition as an electron injection layer having an average thickness of 1 nm.

VI. A layer of Al was formed on the electron injection layer by vacuum deposition as an Al cathode having an average thickness of 100 nm.

VII. A glass cover (the sealing member) was put over the formed layers and fixed and sealed with epoxy resin.

By these operations, a light-emitting element was prepared.

Example 3-2

A light-emitting element was prepared in the same way as in Example 3-1 except that the host material in the light-emitting layer was compound H1-5 (a tetracene-based material).

Example 3-3

A light-emitting element was prepared in the same way as in Example 3-1 except that the host material in the light-emitting layer was compound H1-13 (a tetracene-based material).

Example 3-4

A light-emitting element was prepared in the same way as in Example 3-1 except that the host material in the light-emitting layer was compound H2-30 (an anthracene-based material).

Example 3-5

A light-emitting element was prepared in the same way as in Example 3-1 except that the host material in the light-emitting layer was compound H2-47 (an anthracene-based material).

Example 3-6

A light-emitting element was prepared in the same way as in Example 3-1 except that the host material in the light-emitting layer was compound H2-52 (an anthracene-based material).

Example 3-7

A light-emitting element was prepared in the same way as in Example 3-1 except that the host material in the light-emitting layer was Alq$_3$.

Example 3-8

A light-emitting element was prepared in the same way as in Example 3-1 except that the light-emitting material (dopant) content (doping level) of the light-emitting layer was 1.0 wt %.

Example 3-9

A light-emitting element was prepared in the same way as in Example 3-1 except that the light-emitting material (dopant) content (doping level) of the light-emitting layer was 2.0 wt %.

Example 3-10

A light-emitting element was prepared in the same way as in Example 3-1 except that the light-emitting material (dopant) content (doping level) of the light-emitting layer was 10.0 wt %.

Example 3-11

A light-emitting element was prepared in the same way as in Example 3-1 except that the average thickness of the light-emitting layer was 15 nm and the average thickness of the electron transport layer was 100 nm.

Example 3-12

A light-emitting element was prepared in the same way as in Example 3-1 except that the average thickness of the light-emitting layer was 50 nm and the average thickness of the electron transport layer was 65 nm.

Example 3-13

A light-emitting element was prepared in the same way as in Example 3-1 except that the average thickness of the light-emitting layer was 70 nm and the average thickness of the electron transport layer was 45 nm.

Example 3-14

A light-emitting element was prepared in the same way as in Example 3-1 except that the light-emitting material in the light-emitting layer was compound D3-1.

Example 3-15

A light-emitting element was prepared in the same way as in Example 3-1 except that the light-emitting material in the light-emitting layer was compound D3-3.

Reference Example 3-1

A light-emitting element was prepared in the same way as in Example 3-1 except that the light-emitting material (dopant) in the light-emitting layer was omitted (the light-emitting layer was composed solely of compound H1-2).

Reference Example 3-2

A light-emitting element was prepared in the same way as in Example 3-1 except that the electron transport layer was made of 2,9-dimethyl-4,7-diphenyl-1,10-phenanthroline (BCP).

6. Testing

The light-emitting elements of Examples and Reference Examples were tested in the following way. A constant electric current of 100 mA/cm$^2$ was applied to the light-emitting element from a constant-current power supply (Keithley 2400, TOYO Corporation), and the peak emission wavelength was measured using a miniature fiber optic spectrometer (PMA-11, Hamamatsu Photonics K.K.). The emission power was measured using an optical power meter (8230 Optical Power Meter, ADC Corporation).

The voltage at the onset of light emission (driving voltage) was also measured.

Furthermore, a constant electric current of 150 mA/cm$^2$ was applied to the light-emitting element, and the time required for the luminance to decrease to 85% of the initial value ($LT_{85}$) was measured.

The test results are summarized in Tables 1, 2, and 3.

TABLE 1

| | Light-emitting layer | | | | Electron transport layer | | Evaluations | | | |
|---|---|---|---|---|---|---|---|---|---|---|
| | Light-emitting material | Host material | Light-emitting material content (wt %) | Average thickness (nm) | Material | Average thickness (nm) | Peak emission wavelength (nm) | Emission power (mW/cm$^2$) | Voltage (V) | $LT_{85}$ (hr) |
| Example 1-1 | D1-2 | H1-2 | 4 | 25 | ETL-A3 | 90 | 845 | 1.6 | 5.0 | >500 |
| Example 1-2 | D1-2 | H1-5 | 4 | 25 | ETL-A3 | 90 | 845 | 1.6 | 4.9 | >500 |
| Example 1-3 | D1-2 | H1-13 | 4 | 25 | ETL-A3 | 90 | 845 | 1.6 | 5.0 | >500 |
| Example 1-4 | D1-2 | H2-30 | 4 | 25 | ETL-A3 | 90 | 845 | 0.7 | 6.9 | >1000 |
| Example 1-5 | D1-2 | H2-47 | 4 | 25 | ETL-A3 | 90 | 845 | 0.8 | 6.9 | >1000 |
| Example 1-6 | D1-2 | H2-52 | 4 | 25 | ETL-A3 | 90 | 845 | 0.7 | 7.0 | >1000 |
| Example 1-7 | D1-2 | Alq$_3$ | 4 | 25 | ETL-A3 | 90 | 855 | 0.5 | 6.5 | >500 |
| Example 1-8 | D1-2 | H1-2 | 1 | 25 | ETL-A3 | 90 | 825 | 1.8 | 4.9 | >200 |
| Example 1-9 | D1-2 | H1-2 | 2 | 25 | ETL-A3 | 90 | 835 | 1.7 | 4.9 | >300 |
| Example 1-10 | D1-2 | H1-2 | 10 | 25 | ETL-A3 | 90 | 855 | 1.2 | 5.2 | >700 |
| Example 1-11 | D1-2 | H1-2 | 4 | 15 | ETL-A3 | 100 | 845 | 1.6 | 4.8 | >500 |
| Example 1-12 | D1-2 | H1-2 | 4 | 50 | ETL-A3 | 65 | 845 | 1.5 | 5.5 | >500 |
| Example 1-13 | D1-2 | H1-2 | 4 | 70 | ETL-A3 | 45 | 845 | 1.5 | 6.0 | >600 |
| Example 1-14 | D1-4 | H1-2 | 4 | 25 | ETL-A3 | 90 | 805 | 1.3 | 4.9 | >500 |
| Example 1-15 | D1-5 | H1-2 | 4 | 25 | ETL-A3 | 90 | 850 | 1.5 | 5.0 | >500 |
| Example 1-16 | D1-8 | H1-2 | 4 | 25 | ETL-A3 | 90 | 855 | 1.4 | 4.9 | >500 |
| Reference Example 1-1 | — | H1-2 | — | 25 | ETL-A3 | 90 | 520 | 1.2 | 4.9 | 100 |
| Reference Example 1-2 | D1-2 | H1-2 | 4 | 25 | BCP | 90 | 845 | 1.6 | 7.3 | 30 |

TABLE 2

| | Light-emitting layer | | | | Electron transport layer | | Evaluations | | | |
|---|---|---|---|---|---|---|---|---|---|---|
| | Light-emitting material | Host material | Light-emitting material content (wt %) | Average thickness (nm) | Material | Average thickness (nm) | Peak emission wavelength (nm) | Emission power (mW/cm$^2$) | Voltage (V) | $LT_{85}$ (hr) |
| Example 2-1 | D2-2 | H1-2 | 4 | 25 | ETL-A3 | 90 | 840 | 1.3 | 5.1 | >500 |
| Example 2-2 | D2-2 | H1-5 | 4 | 25 | ETL-A3 | 90 | 840 | 1.4 | 5.0 | >500 |
| Example 2-3 | D2-2 | H1-13 | 4 | 25 | ETL-A3 | 90 | 840 | 1.5 | 5.2 | >500 |
| Example 2-4 | D2-2 | H2-30 | 4 | 25 | ETL-A3 | 90 | 840 | 0.6 | 6.9 | >1000 |
| Example 2-5 | D2-2 | H2-47 | 4 | 25 | ETL-A3 | 90 | 840 | 0.7 | 6.8 | >1000 |
| Example 2-6 | D2-2 | H2-52 | 4 | 25 | ETL-A3 | 90 | 840 | 0.7 | 6.9 | >1000 |
| Example 2-7 | D2-2 | Alq$_3$ | 4 | 25 | ETL-A3 | 90 | 850 | 0.3 | 6.6 | >500 |
| Example 2-8 | D2-2 | H1-2 | 1 | 25 | ETL-A3 | 90 | 820 | 1.6 | 5.0 | >200 |

TABLE 2-continued

| | Light-emitting layer | | | | Electron transport layer | | Evaluations | | | |
|---|---|---|---|---|---|---|---|---|---|---|
| | Light-emitting material | Host material | Light-emitting material content (wt %) | Average thickness (nm) | Material | Average thickness (nm) | Peak emission wavelength (nm) | Emission power (mW/cm$^2$) | Voltage (V) | LT$_{85}$ (hr) |
| Example 2-9 | D2-2 | H1-2 | 2 | 25 | ETL-A3 | 90 | 830 | 1.4 | 5.0 | >300 |
| Example 2-10 | D2-2 | H1-2 | 10 | 25 | ETL-A3 | 90 | 850 | 1.0 | 5.3 | >600 |
| Example 2-11 | D2-2 | H1-2 | 4 | 15 | ETL-A3 | 100 | 840 | 1.3 | 4.9 | >500 |
| Example 2-12 | D2-2 | H1-2 | 4 | 50 | ETL-A3 | 65 | 840 | 1.3 | 5.4 | >500 |
| Example 2-13 | D2-2 | H1-2 | 4 | 70 | ETL-A3 | 45 | 840 | 1.2 | 5.8 | >500 |
| Example 2-14 | D2-1 | H1-2 | 4 | 25 | ETL-A3 | 90 | 800 | 1.2 | 5.1 | >500 |
| Example 2-15 | D2-3 | H1-2 | 4 | 25 | ETL-A3 | 90 | 870 | 0.6 | 5.1 | >500 |
| Reference Example 2-1 | — | H1-2 | — | 25 | ETL-A3 | 90 | 520 | 1.2 | 4.9 | 100 |
| Reference Example 2-2 | D2-2 | H1-2 | 4 | 25 | BCP | 90 | 840 | 1.3 | 7.2 | 30 |

TABLE 3

| | Light-emitting layer | | | | Electron transport layer | | Evaluations | | | |
|---|---|---|---|---|---|---|---|---|---|---|
| | Light-emitting material | Host material | Light-emitting material content (wt %) | Average thickness (nm) | Material | Average thickness (nm) | Peak emission wavelength (nm) | Emission power (mW/cm$^2$) | Voltage (V) | LT$_{85}$ (hr) |
| Example 3-1 | D3-2 | H1-2 | 4 | 25 | ETL-A3 | 90 | 843 | 1.0 | 5.2 | >500 |
| Example 3-2 | D3-2 | H1-5 | 4 | 25 | ETL-A3 | 90 | 843 | 1.1 | 5.1 | >500 |
| Example 3-3 | D3-2 | H1-13 | 4 | 25 | ETL-A3 | 90 | 843 | 1.2 | 5.2 | >500 |
| Example 3-4 | D3-2 | H2-30 | 4 | 25 | ETL-A3 | 90 | 843 | 0.5 | 7.0 | >1000 |
| Example 3-5 | D3-2 | H2-47 | 4 | 25 | ETL-A3 | 90 | 843 | 0.6 | 6.9 | >1000 |
| Example 3-6 | D3-2 | H2-52 | 4 | 25 | ETL-A3 | 90 | 843 | 0.6 | 7.0 | >1000 |
| Example 3-7 | D3-2 | Alq$_3$ | 4 | 25 | ETL-A3 | 90 | 854 | 0.2 | 6.8 | >500 |
| Example 3-8 | D3-2 | H1-2 | 1 | 25 | ETL-A3 | 90 | 822 | 1.3 | 5.0 | >200 |
| Example 3-9 | D3-2 | H1-2 | 2 | 25 | ETL-A3 | 90 | 833 | 1.1 | 5.1 | >300 |
| Example 3-10 | D3-2 | H1-2 | 10 | 25 | ETL-A3 | 90 | 852 | 0.9 | 5.5 | >600 |
| Example 3-11 | D3-2 | H1-2 | 4 | 15 | ETL-A3 | 100 | 843 | 1.0 | 5.0 | >500 |
| Example 3-12 | D3-2 | H1-2 | 4 | 50 | ETL-A3 | 65 | 843 | 1.0 | 5.4 | >500 |
| Example 3-13 | D3-2 | H1-2 | 4 | 70 | ETL-A3 | 45 | 843 | 0.9 | 5.9 | >500 |
| Example 3-14 | D3-1 | H1-2 | 4 | 25 | ETL-A3 | 90 | 804 | 1.0 | 5.1 | >500 |
| Example 3-15 | D3-3 | H1-2 | 4 | 25 | ETL-A3 | 90 | 873 | 0.5 | 5.1 | >500 |
| Reference Example 3-1 | — | H1-2 | — | 25 | ETL-A3 | 90 | 520 | 1.2 | 4.9 | 100 |
| Reference Example 3-2 | D3-2 | H1-2 | 4 | 25 | BCP | 90 | 843 | 1.0 | 7.3 | 30 |

As is clear from Tables 1 to 3, the light-emitting elements of Examples emitted near-infrared light and were relatively intense in terms of emission power. Furthermore, the light-emitting elements of Examples operated at a relatively low voltage. These results indicate that the light-emitting elements of Examples were of excellent light emission efficiency.

Moreover, the light-emitting elements of Examples were longer-lived than those of Reference Examples.

The entire disclosure of Japan Patent application No. 2012-230596, No. 2012-230598 and No. 2012-230599, filed Oct. 18, 2012 are expressly incorporated by reference herein.

What is claimed is:

1. A thiadiazole comprising a basic skeleton represented by any of formulae (1), (2), and (3) in a molecule

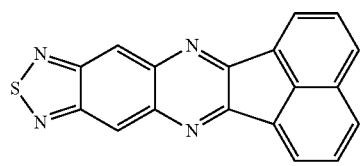
(1)

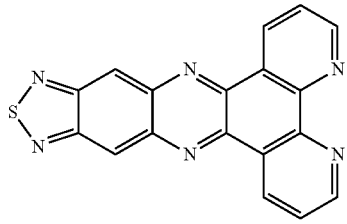
(2)

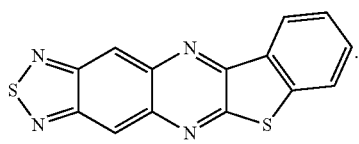
(3)

2. The thiadiazole according to claim 1, wherein:
the thiadiazole is a compound represented by formula (4) when containing the basic skeleton represented by formula (1) in the molecule;
the thiadiazole is a compound represented by formula (5) when containing the basic skeleton represented by formula (2) in the molecule; and the thiadiazole is a compound represented by formula (6) when containing the basic skeleton represented by formula (3) in the molecule:

(4)
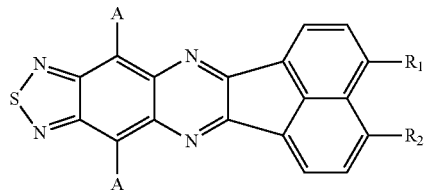

(5)
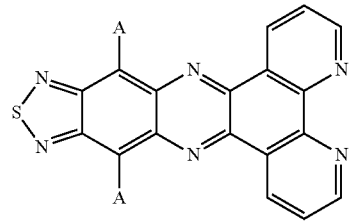

(6)
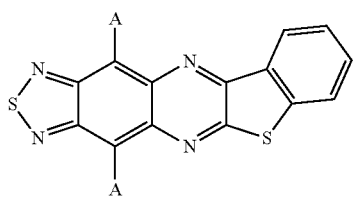

where each A independently represents a hydrogen atom, an alkyl group, or a substituted or unsubstituted aryl group, aryl amino group, or triarylamine, each of $R_1$ and $R_2$ independently represents a hydrogen atom, an alkyl group, or a substituted or unsubstituted aryl group, and $R_1$ and $R_2$ may be the same or different.

3. The thiadiazole according to claim 2, wherein:

the compound represented by formula (4) is a compound represented by any of formulae (7), (8), and (9);

the compound represented by formula (5) is a compound represented by any of formulae (10), (11), and (12); and the compound represented by formula (6) is a compound represented by any of formulae (13), (14), and (15):

(7)
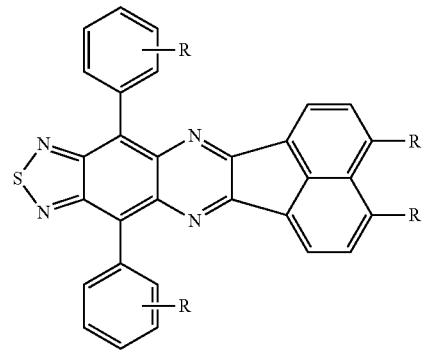

(8)
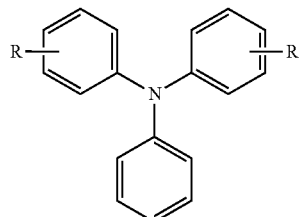
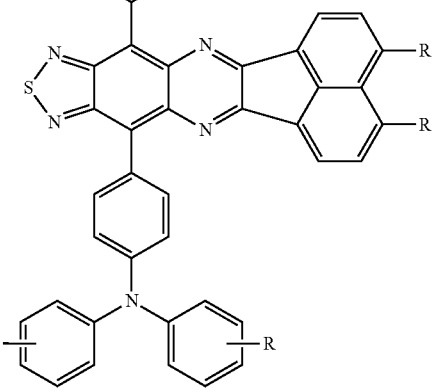

(9)
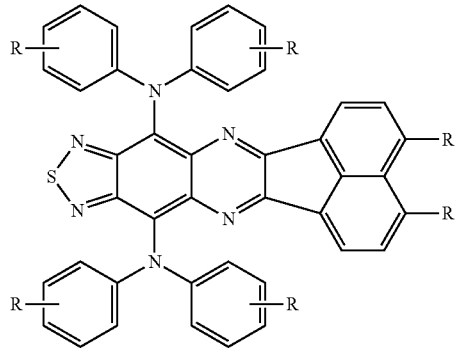

(10)
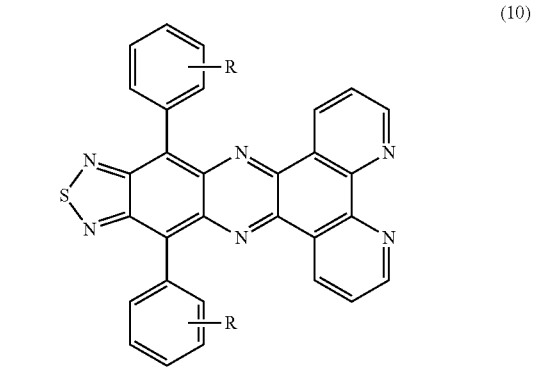

(11)
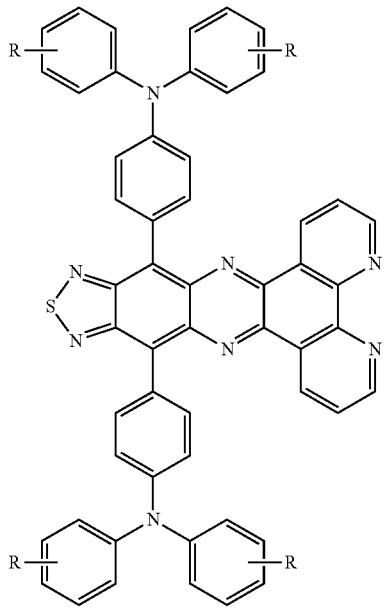

(12)
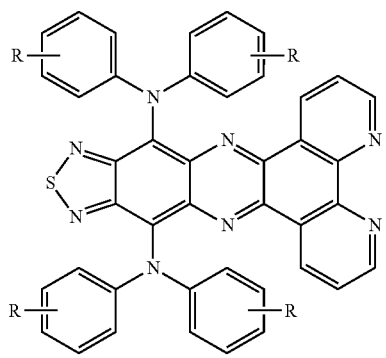

(13)
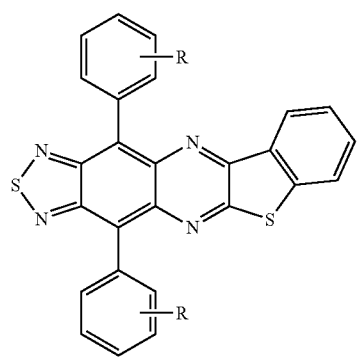

(14)
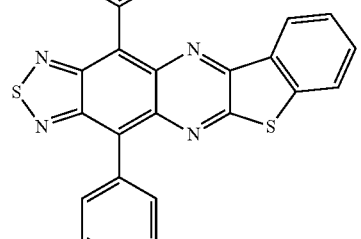

(15)
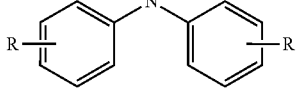
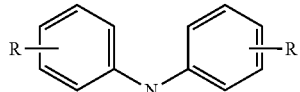
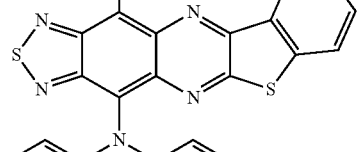
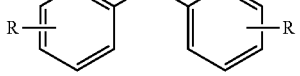

where each R independently represents a hydrogen atom, an alkyl group, or a substituted or unsubstituted aryl group, and there may be a ring formed by a carbon linkage between two adjacent R's.

4. A compound for light-emitting elements comprising the thiadiazole according to claim 1.

5. A light-emitting element comprising:
an anode;
a cathode; and
a layer between the anode and the cathode, the layer containing the thiadiazole according to claim 1.

6. The light-emitting element according to claim 5, wherein the layer contains the thiadiazole as a guest material and also contains a host material for the guest material.

7. The light-emitting element according to claim 6, wherein the host material is a compound represented by formula IRH-1:

IRH-1
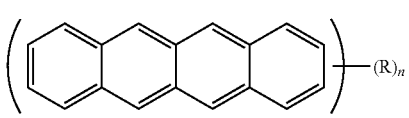

where n represents a natural number of 1 to 12, and each R is independently a hydrogen atom, an alkyl group, or a substituted or unsubstituted aryl or aryl amino group.

8. The light-emitting element according to claim 6, wherein the host material is a compound represented by formula IRH-2:

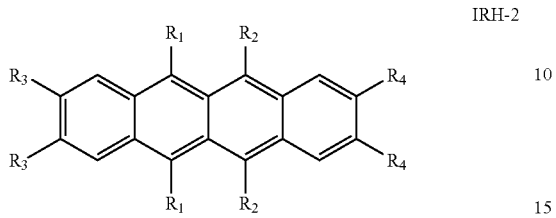

IRH-2 where each of $R_1$ to $R_4$ independently represents a hydrogen atom, an alkyl group, or a substituted or unsubstituted aryl or aryl amino group, with some or all of $R_1$ to $R_4$ being the same or all of $R_1$ to $R_4$ being different.

9. The light-emitting element according to claim 6, wherein the host material is a compound represented by formula IRH-3:

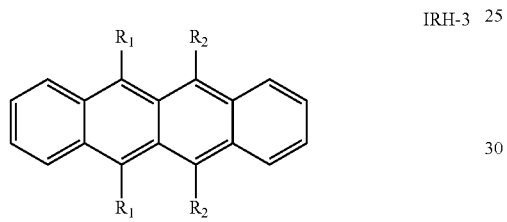

IRH-3 where each of $R_1$ and $R_2$ independently represents a hydrogen atom, an alkyl group, or a substituted or unsubstituted aryl or aryl amino group, and $R_1$ and $R_2$ may be the same or different.

10. The light-emitting element according to claim 6, wherein the host material is a compound represented by formula IRH-4:

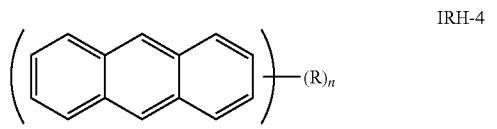

IRH-4 where n represents a natural number of 1 to 10, and each R independently represents a hydrogen atom, an alkyl group, or a substituted or unsubstituted aryl or aryl amino group.

11. The light-emitting element according to claim 6, wherein the host material is a compound represented by formula IRH-5:

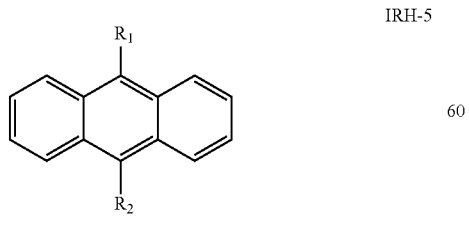

IRH-5 where each of $R_1$ and $R_2$ independently represents a hydrogen atom, an alkyl group, or a substituted or unsubstituted aryl or aryl amino group, and $R_1$ and $R_2$ may be the same or different.

12. The light-emitting element according to claim 6, wherein the host material is a compound represented by formula IRH-6:

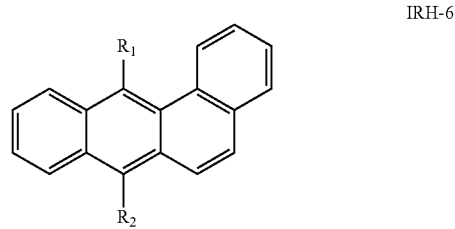

IRH-6 where each of $R_1$ and $R_2$ independently represents a hydrogen atom, an alkyl group, or a substituted or unsubstituted aryl or aryl amino group, and $R_1$ and $R_2$ may be the same or different.

13. The light-emitting element according to claim 6, wherein the host material is a compound represented by formula IRH-7:

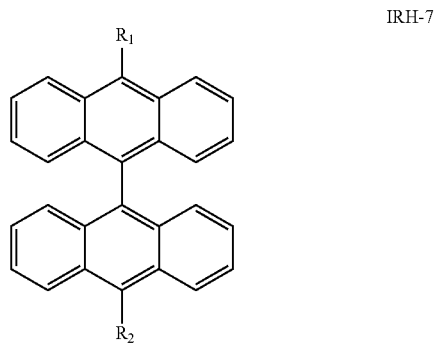

IRH-7 where each of $R_1$ and $R_2$ independently represents a hydrogen atom, an alkyl group, or a substituted or unsubstituted aryl or aryl amino group, and $R_1$ and $R_2$ may be the same or different.

14. The light-emitting element according to claim 6, wherein the host material is a compound represented by formula IRH-8:

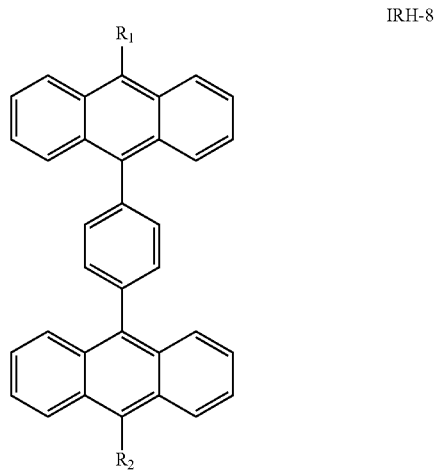

IRH-8 where each of $R_1$ and $R_2$ independently represents a hydrogen atom, an alkyl group, or a substituted or unsubstituted aryl or aryl amino group, and $R_1$ and $R_2$ may be the same or different.

15. The light-emitting element according to claim 5, wherein the host material is composed of carbon and hydrogen atoms.

16. The light-emitting element according to claim 5, wherein:
   the thiadiazole is used as a light-emitting material; and
   the layer is a light-emitting layer which emits light when electric current flows between the anode and the cathode.

17. A light-emitting apparatus comprising the light-emitting element according to claim 5.

18. An authentication apparatus comprising the light-emitting element according to claim 5.

19. An electronic device comprising the light-emitting element according to claim 5.

* * * * *